US008685415B2

(12) United States Patent
Callewaert et al.

(10) Patent No.: US 8,685,415 B2
(45) Date of Patent: Apr. 1, 2014

(54) MYCOBACTERIUM MUTANTS FOR VACCINES WITH IMPROVED PROTECTIVE EFFICACY

(75) Inventors: Nico Callewaert, Nevele (BE); Anjana Batni, Gent (BE); Nele Festjens, Kluisbergen (BE); Christiane Huygen, Ukkel (BE)

(73) Assignees: VIB VZM, Ghent (BE); Universiteit Gent, Ghent (BE); Wetenschappelijk Instituut Volksgezondheid, Brussels (BE)

( * ) Notice: Subject to any disclaimer, the term of this patent is extended or adjusted under 35 U.S.C. 154(b) by 0 days.

(21) Appl. No.: 13/387,096

(22) PCT Filed: Jul. 28, 2010

(86) PCT No.: PCT/EP2010/060986

§ 371 (c)(1), (2), (4) Date: Jan. 25, 2012

(87) PCT Pub. No.: WO2011/012662

PCT Pub. Date: Feb. 3, 2011

(65) Prior Publication Data

US 2012/0128720 A1 May 24, 2012

Related U.S. Application Data

(60) Provisional application No. 61/229,062, filed on Jul. 28, 2009.

(51) Int. Cl.

| | |
|---|---|
| ***A61K 39/04*** | (2006.01) |
| ***A61K 49/00*** | (2006.01) |
| ***A61K 48/00*** | (2006.01) |

(52) U.S. Cl.

USPC ....... 424/248.1; 536/23.1; 536/23.7; 424/9.1; 424/9.2; 424/93.1; 424/93.2; 424/93.4; 424/234.1

(58) Field of Classification Search

USPC ............. 424/9.1, 9.2, 93.1, 93.2, 93.4, 234.1, 424/248.1; 536/23.1, 23.7

See application file for complete search history.

(56) References Cited

U.S. PATENT DOCUMENTS

2006/0172301 A1* 8/2006 Liu et al. ........................... 435/6

FOREIGN PATENT DOCUMENTS

| | | |
|---|---|---|
| WO | WO 2006/078164 | 7/2006 |
| WO | WO 2007/084353 | 7/2007 |
| WO | WO 2009/009798 | 1/2009 |
| WO | WO 2011/012662 | 2/2011 |

OTHER PUBLICATIONS

International Search Report PCT/EP2010/060986 dated Dec. 23, 2010.

* cited by examiner

*Primary Examiner* — Rodney P. Swartz

(74) *Attorney, Agent, or Firm* — TraskBritt

(57) ABSTRACT

*Tuberculosis* (TB) is a major health problem and currently, the only licensed TB vaccine is *Mycobacterium bovis* Bacille Calmette-Guerin (*M. bovis* BCG). In the present invention, mutation of mycobacterial components reportedly involved in phagosome maturation inhibition was evaluated for vaccine purposes, as such mutations should result in better vaccine antigen processing and presentation. Thus, BCG mutants in genes coding for ManLAM capping α-1,2-mannosyltransferases and the PI3P phosphatase SapM were evaluated as TB vaccines in a stringent mouse model. Vaccination with both ManLAM capping mutants and the SapM mutant resulted in significantly longer survival as compared to non-vaccinated mice, whereas vaccination with the parental BCG did not. Moreover, mice vaccinated with the SapM mutant survived significantly longer than mice vaccinated with the parental BCG. The mutant BCG strains showed unaltered phagocytosis, replication, lysosome colocalization and oxidant activity in macrophages and similarly induced autophagy in the latter. Additionally, replication and granuloma formation in mice was unaffected, indicating BCG-equivalent safety of these vaccines.

16 Claims, 15 Drawing Sheets

A

B

C

D

E

F

G

SEQUENCE LISTING

```
<160> NUMBER OF SEQ ID NOS: 22

<210> SEQ ID NO 1
<211> LENGTH: 900
<212> TYPE: DNA
<213> ORGANISM: Mycobacterium bovis
<220> FEATURE:
<221> NAME/KEY: CDS
<222> LOCATION: (1)..(900)

<400> SEQUENCE: 1

atg ctc cgc gga atc cag gct ctc agc cgg ccc ctg acc agg gta tac       48
Met Leu Arg Gly Ile Gln Ala Leu Ser Arg Pro Leu Thr Arg Val Tyr
1               5                   10                  15

cgt gcc ttg gcg gtg atc ggt gtc ctg gca gca tcg ttg ctg gcc tca       96
Arg Ala Leu Ala Val Ile Gly Val Leu Ala Ala Ser Leu Leu Ala Ser
            20                  25                  30

tgg gtc ggc gct gtc cca caa gtg ggt ctg gca gcg agt gcc ctg ccg      144
Trp Val Gly Ala Val Pro Gln Val Gly Leu Ala Ala Ser Ala Leu Pro
        35                  40                  45

acc ttc gcg cac gtg gtc atc gtg gtg gag gag aac cgc tcg cag gcc      192
Thr Phe Ala His Val Val Ile Val Val Glu Glu Asn Arg Ser Gln Ala
    50                  55                  60

gcc atc atc ggt aac aag tcg gct ccc ttc atc aat tcg ctg gcc gcc      240
Ala Ile Ile Gly Asn Lys Ser Ala Pro Phe Ile Asn Ser Leu Ala Ala
65                  70                  75                  80

aac ggc gcg atg atg gcc cag gcg ttc gcc gaa aca cac ccg agc gaa      288
Asn Gly Ala Met Met Ala Gln Ala Phe Ala Glu Thr His Pro Ser Glu
                85                  90                  95

ccg aac tac ctg gca ctg ttc gct ggc aac aca ttc ggg ttg acg aag      336
Pro Asn Tyr Leu Ala Leu Phe Ala Gly Asn Thr Phe Gly Leu Thr Lys
            100                 105                 110

aac acc tgc ccc gtc aac ggc ggc gcg ctg ccc aac ctg ggt tct gag      384
Asn Thr Cys Pro Val Asn Gly Gly Ala Leu Pro Asn Leu Gly Ser Glu
        115                 120                 125

ttg ctc agc gcc ggt tac aca ttc atg ggg ttc gcc gaa gac ttg cct      432
Leu Leu Ser Ala Gly Tyr Thr Phe Met Gly Phe Ala Glu Asp Leu Pro
    130                 135                 140

gcg gtc ggc tcc acg gtg tgc agt gcg ggc aaa tac gca cgc aaa cac      480
Ala Val Gly Ser Thr Val Cys Ser Ala Gly Lys Tyr Ala Arg Lys His
145                 150                 155                 160
```

```
gtg ccg tgg gtc aac ttc agt aac gtg ccg gcg aca ctg tcg gtg ccg      528
Val Pro Trp Val Asn Phe Ser Asn Val Pro Ala Thr Leu Ser Val Pro
                165                 170                 175

ttt tcg gca ttt ccg aag ccg cag aat tac ccc ggc ctg ccg acg gtg      576
Phe Ser Ala Phe Pro Lys Pro Gln Asn Tyr Pro Gly Leu Pro Thr Val
            180                 185                 190

tcg ttt gtc atc cct aac gcc gac aac gac atg cac gac ggc tcg atc      624
Ser Phe Val Ile Pro Asn Ala Asp Asn Asp Met His Asp Gly Ser Ile
        195                 200                 205

gcc caa ggc gac gcc tgg ctg aac cgc cac ctg tcg gca tat gcc aac      672
Ala Gln Gly Asp Ala Trp Leu Asn Arg His Leu Ser Ala Tyr Ala Asn
    210                 215                 220

tgg gcc aag aca aac aac agc ctg ctc gtt gtg acc tgg gac gaa gac      720
Trp Ala Lys Thr Asn Asn Ser Leu Leu Val Val Thr Trp Asp Glu Asp
225                 230                 235                 240

gac ggc agc agc cgc aat cag atc ccg acg gtg ttc tac ggc gcg cac      768
Asp Gly Ser Ser Arg Asn Gln Ile Pro Thr Val Phe Tyr Gly Ala His
                245                 250                 255

gtg cgg ccc gga act tac aac gag acc atc agc cac tac aac gtg ctg      816
Val Arg Pro Gly Thr Tyr Asn Glu Thr Ile Ser His Tyr Asn Val Leu
            260                 265                 270

tcc aca ttg gag cag atc tac gga ctg ccc aag acg ggt tat gcg acc      864
Ser Thr Leu Glu Gln Ile Tyr Gly Leu Pro Lys Thr Gly Tyr Ala Thr
        275                 280                 285

aat gct ccg cca ata acc gat att tgg ggc gac tag                      900
Asn Ala Pro Pro Ile Thr Asp Ile Trp Gly Asp
    290                 295


<210> SEQ ID NO 2
<211> LENGTH: 299
<212> TYPE: PRT
<213> ORGANISM: Mycobacterium bovis

<400> SEQUENCE: 2

Met Leu Arg Gly Ile Gln Ala Leu Ser Arg Pro Leu Thr Arg Val Tyr
1               5                   10                  15

Arg Ala Leu Ala Val Ile Gly Val Leu Ala Ala Ser Leu Leu Ala Ser
            20                  25                  30

Trp Val Gly Ala Val Pro Gln Val Gly Leu Ala Ala Ser Ala Leu Pro
        35                  40                  45

Thr Phe Ala His Val Val Ile Val Val Glu Glu Asn Arg Ser Gln Ala
    50                  55                  60

Ala Ile Ile Gly Asn Lys Ser Ala Pro Phe Ile Asn Ser Leu Ala Ala
65                  70                  75                  80

Asn Gly Ala Met Met Ala Gln Ala Phe Ala Glu Thr His Pro Ser Glu
                85                  90                  95

Pro Asn Tyr Leu Ala Leu Phe Ala Gly Asn Thr Phe Gly Leu Thr Lys
            100                 105                 110

Asn Thr Cys Pro Val Asn Gly Gly Ala Leu Pro Asn Leu Gly Ser Glu
        115                 120                 125

Leu Leu Ser Ala Gly Tyr Thr Phe Met Gly Phe Ala Glu Asp Leu Pro
    130                 135                 140

Ala Val Gly Ser Thr Val Cys Ser Ala Gly Lys Tyr Ala Arg Lys His
145                 150                 155                 160

Val Pro Trp Val Asn Phe Ser Asn Val Pro Ala Thr Leu Ser Val Pro
                165                 170                 175

Phe Ser Ala Phe Pro Lys Pro Gln Asn Tyr Pro Gly Leu Pro Thr Val
            180                 185                 190
```

```
Ser Phe Val Ile Pro Asn Ala Asp Asn Asp Met His Asp Gly Ser Ile
        195                 200                 205

Ala Gln Gly Asp Ala Trp Leu Asn Arg His Leu Ser Ala Tyr Ala Asn
    210                 215                 220

Trp Ala Lys Thr Asn Asn Ser Leu Leu Val Val Thr Trp Asp Glu Asp
225                 230                 235                 240

Asp Gly Ser Ser Arg Asn Gln Ile Pro Thr Val Phe Tyr Gly Ala His
                245                 250                 255

Val Arg Pro Gly Thr Tyr Asn Glu Thr Ile Ser His Tyr Asn Val Leu
            260                 265                 270

Ser Thr Leu Glu Gln Ile Tyr Gly Leu Pro Lys Thr Gly Tyr Ala Thr
        275                 280                 285

Asn Ala Pro Pro Ile Thr Asp Ile Trp Gly Asp
    290                 295


<210> SEQ ID NO 3
<211> LENGTH: 1671
<212> TYPE: DNA
<213> ORGANISM: Mycobacterium bovis
<220> FEATURE:
<221> NAME/KEY: CDS
<222> LOCATION: (1)..(1671)

<400> SEQUENCE: 3

atg cat gcg agt cgt ccc ggc gca ccg ccg cac gcc ggg ctg ccc agt       48
Met His Ala Ser Arg Pro Gly Ala Pro Pro His Ala Gly Leu Pro Ser
1               5                   10                  15

cgc cga acc gcc ggt gac cag gat cat cgc gcg gac cct aag gtg acc       96
Arg Arg Thr Ala Gly Asp Gln Asp His Arg Ala Asp Pro Lys Val Thr
            20                  25                  30

cgc atc atg tcc gcc tcc act ctg gag cag ccc gcg gca gca cac gtc      144
Arg Ile Met Ser Ala Ser Thr Leu Glu Gln Pro Ala Ala Ala His Val
        35                  40                  45

gac gag ttg gtg gcg cgg atg cgc ggc cgg ctg ctc gac ccg ctg gcg      192
Asp Glu Leu Val Ala Arg Met Arg Gly Arg Leu Leu Asp Pro Leu Ala
    50                  55                  60

att gca gtg ctg gcc gcg gtc atc agc ggc gcc tgg gca agc agg cca      240
Ile Ala Val Leu Ala Ala Val Ile Ser Gly Ala Trp Ala Ser Arg Pro
65                  70                  75                  80

tcg ttg tgg ttc gac gag ggg gca acg atc tcg gct tca gcc agc cgg      288
Ser Leu Trp Phe Asp Glu Gly Ala Thr Ile Ser Ala Ser Ala Ser Arg
                85                  90                  95

aca ttg cca gag cta tgg agt ctg ctg ggc cat atc gac gcc gtg cac      336
Thr Leu Pro Glu Leu Trp Ser Leu Leu Gly His Ile Asp Ala Val His
            100                 105                 110

ggc ctg tac tac ctg ttg atg cat ggc tgg ttc gcc ata ttt ccg ccc      384
Gly Leu Tyr Tyr Leu Leu Met His Gly Trp Phe Ala Ile Phe Pro Pro
        115                 120                 125

acc gaa tta tgg tcg cgg ctt ccc agc tgc ctg gcc att gga gcg gcc      432
Thr Glu Leu Trp Ser Arg Leu Pro Ser Cys Leu Ala Ile Gly Ala Ala
    130                 135                 140

gcc gcc ggc gtg gtg gtt ttt gcc aaa cag ttt tcg gga cgc acc acg      480
Ala Ala Gly Val Val Val Phe Ala Lys Gln Phe Ser Gly Arg Thr Thr
145                 150                 155                 160

gcg gtg tgt gcg gga gcc gtg ttc gcg att ctg ccc agg gtg acg tgg      528
Ala Val Cys Ala Gly Ala Val Phe Ala Ile Leu Pro Arg Val Thr Trp
                165                 170                 175

gcc gga atc gaa gca cgc tcc tcc gcg ctg tcg gta gca gcc gcc gtc      576
Ala Gly Ile Glu Ala Arg Ser Ser Ala Leu Ser Val Ala Ala Ala Val
            180                 185                 190
```

```
tgg ctg acc gta tta ctc gtg gcc gcg gtg cgg tgc aac acc cag cgg      624
Trp Leu Thr Val Leu Leu Val Ala Ala Val Arg Cys Asn Thr Gln Arg
        195                 200                 205

cgg tgg ctg ctc tac gcg ctg gtt ttg atg ctg tcg atc ttg gtc agt      672
Arg Trp Leu Leu Tyr Ala Leu Val Leu Met Leu Ser Ile Leu Val Ser
    210                 215                 220

atc aac ctg gcc ctg ttg gta ccg gcc tat gcg acg atg gtg ccg ctg      720
Ile Asn Leu Ala Leu Leu Val Pro Ala Tyr Ala Thr Met Val Pro Leu
225                 230                 235                 240

ctg gcg tcc ggg aaa tca cgc aaa tct ccc gtg atc tgg tgg acg gtc      768
Leu Ala Ser Gly Lys Ser Arg Lys Ser Pro Val Ile Trp Trp Thr Val
                245                 250                 255

gtc acg gca gcc gcg ctc ggg gcc atg aca ccg ttc ata ctg ttc gcc      816
Val Thr Ala Ala Ala Leu Gly Ala Met Thr Pro Phe Ile Leu Phe Ala
            260                 265                 270

cac ggc cag gtt tgg cag gtc ggg tgg atc gca ggg ttg aac aga aac      864
His Gly Gln Val Trp Gln Val Gly Trp Ile Ala Gly Leu Asn Arg Asn
        275                 280                 285

atc att ctc gac gtc ata cac cgc cag tat ttc gat cac agt gtt ccg      912
Ile Ile Leu Asp Val Ile His Arg Gln Tyr Phe Asp His Ser Val Pro
    290                 295                 300

ttc gcc atc ctc gcg ggc ctc atc gtc gct gcc ggc atc gcg gcg cat      960
Phe Ala Ile Leu Ala Gly Leu Ile Val Ala Ala Gly Ile Ala Ala His
305                 310                 315                 320

ctg gcc gga gct cgt gga ccc ggt ggc gat acc cac cgg ctc gtg ctc     1008
Leu Ala Gly Ala Arg Gly Pro Gly Gly Asp Thr His Arg Leu Val Leu
                325                 330                 335

gtc agc gca gcc tgg atc gtc gtg ccc acc gcc gtc gtc ctc atc tac     1056
Val Ser Ala Ala Trp Ile Val Val Pro Thr Ala Val Val Leu Ile Tyr
            340                 345                 350

tcg gcg acc gtc gaa ccg atc tac tac ccg cgc tac ctg atc ctc acc     1104
Ser Ala Thr Val Glu Pro Ile Tyr Tyr Pro Arg Tyr Leu Ile Leu Thr
        355                 360                 365

gcc ccc gcc gcg gcc gtc atc ctg gcg gtt tgc gtc gtc acc atc gcc     1152
Ala Pro Ala Ala Ala Val Ile Leu Ala Val Cys Val Val Thr Ile Ala
    370                 375                 380

cgc aag ccg tgg ctc atc gcc ggg gtc gtg ttt ctc ctt gcc gcc gca     1200
Arg Lys Pro Trp Leu Ile Ala Gly Val Val Phe Leu Leu Ala Ala Ala
385                 390                 395                 400

gcg ttt ccg aac tac ttc ttc aca cag cgg ggg ccg tac gcg aaa gag     1248
Ala Phe Pro Asn Tyr Phe Phe Thr Gln Arg Gly Pro Tyr Ala Lys Glu
                405                 410                 415

ggc tgg gat tac agc cag gtg gca gat gtc atc agc gcc cat gcc aag     1296
Gly Trp Asp Tyr Ser Gln Val Ala Asp Val Ile Ser Ala His Ala Lys
            420                 425                 430

ccc ggg gat tgc ctg ctg gtg gac aac acc gcg ggt tgg cga ccc ggg     1344
Pro Gly Asp Cys Leu Leu Val Asp Asn Thr Ala Gly Trp Arg Pro Gly
        435                 440                 445

ccc atc cgc gcc ctg ctg gcc acc cgg ccg gcg gcg ttc cgg tcg ctg     1392
Pro Ile Arg Ala Leu Leu Ala Thr Arg Pro Ala Ala Phe Arg Ser Leu
    450                 455                 460

att gac gtc gag cgc ggc acc tac ggc ccc aag gtc ggc act ttg tgg     1440
Ile Asp Val Glu Arg Gly Thr Tyr Gly Pro Lys Val Gly Thr Leu Trp
465                 470                 475                 480

gat ggc cat gtc gct gtg tgg ctt acg acg gcc aag atc gac aag tgc     1488
Asp Gly His Val Ala Val Trp Leu Thr Thr Ala Lys Ile Asp Lys Cys
                485                 490                 495

ccc acg ctg tgg acg ata gcc aat cgt gac aag tcg ttg ccc gat cat     1536
Pro Thr Leu Trp Thr Ile Ala Asn Arg Asp Lys Ser Leu Pro Asp His
            500                 505                 510
```

```
cag gtc ggc gaa atg ttg tca ccg gga aca ggc ttc ggg cgc acg ccc      1584
Gln Val Gly Glu Met Leu Ser Pro Gly Thr Gly Phe Gly Arg Thr Pro
        515                 520                 525

gta tac cgg ttc ccg agc tac ctc ggc ttc cgc atc gtc gag cgc tgg      1632
Val Tyr Arg Phe Pro Ser Tyr Leu Gly Phe Arg Ile Val Glu Arg Trp
    530                 535                 540

cag ttc cac tac tcg cag gtg gtc aag tca acg cgg taa                  1671
Gln Phe His Tyr Ser Gln Val Val Lys Ser Thr Arg
545                 550                 555


<210> SEQ ID NO 4
<211> LENGTH: 556
<212> TYPE: PRT
<213> ORGANISM: Mycobacterium bovis

<400> SEQUENCE: 4

Met His Ala Ser Arg Pro Gly Ala Pro Pro His Ala Gly Leu Pro Ser
1               5                   10                  15

Arg Arg Thr Ala Gly Asp Gln Asp His Arg Ala Asp Pro Lys Val Thr
            20                  25                  30

Arg Ile Met Ser Ala Ser Thr Leu Glu Gln Pro Ala Ala Ala His Val
        35                  40                  45

Asp Glu Leu Val Ala Arg Met Arg Gly Arg Leu Leu Asp Pro Leu Ala
    50                  55                  60

Ile Ala Val Leu Ala Ala Val Ile Ser Gly Ala Trp Ala Ser Arg Pro
65                  70                  75                  80

Ser Leu Trp Phe Asp Glu Gly Ala Thr Ile Ser Ala Ser Ala Ser Arg
                85                  90                  95

Thr Leu Pro Glu Leu Trp Ser Leu Leu Gly His Ile Asp Ala Val His
            100                 105                 110

Gly Leu Tyr Tyr Leu Leu Met His Gly Trp Phe Ala Ile Phe Pro Pro
        115                 120                 125

Thr Glu Leu Trp Ser Arg Leu Pro Ser Cys Leu Ala Ile Gly Ala Ala
    130                 135                 140

Ala Ala Gly Val Val Val Phe Ala Lys Gln Phe Ser Gly Arg Thr Thr
145                 150                 155                 160

Ala Val Cys Ala Gly Ala Val Phe Ala Ile Leu Pro Arg Val Thr Trp
                165                 170                 175

Ala Gly Ile Glu Ala Arg Ser Ser Ala Leu Ser Val Ala Ala Ala Val
            180                 185                 190

Trp Leu Thr Val Leu Leu Val Ala Ala Val Arg Cys Asn Thr Gln Arg
        195                 200                 205

Arg Trp Leu Leu Tyr Ala Leu Val Leu Met Leu Ser Ile Leu Val Ser
    210                 215                 220

Ile Asn Leu Ala Leu Leu Val Pro Ala Tyr Ala Thr Met Val Pro Leu
225                 230                 235                 240

Leu Ala Ser Gly Lys Ser Arg Lys Ser Pro Val Ile Trp Trp Thr Val
                245                 250                 255

Val Thr Ala Ala Ala Leu Gly Ala Met Thr Pro Phe Ile Leu Phe Ala
            260                 265                 270

His Gly Gln Val Trp Gln Val Gly Trp Ile Ala Gly Leu Asn Arg Asn
        275                 280                 285

Ile Ile Leu Asp Val Ile His Arg Gln Tyr Phe Asp His Ser Val Pro
    290                 295                 300

Phe Ala Ile Leu Ala Gly Leu Ile Val Ala Ala Gly Ile Ala Ala His
305                 310                 315                 320
```

```
Leu Ala Gly Ala Arg Gly Pro Gly Gly Asp Thr His Arg Leu Val Leu
                325                 330                 335

Val Ser Ala Ala Trp Ile Val Val Pro Thr Ala Val Val Leu Ile Tyr
            340                 345                 350

Ser Ala Thr Val Glu Pro Ile Tyr Tyr Pro Arg Tyr Leu Ile Leu Thr
        355                 360                 365

Ala Pro Ala Ala Ala Val Ile Leu Ala Val Cys Val Val Thr Ile Ala
    370                 375                 380

Arg Lys Pro Trp Leu Ile Ala Gly Val Val Phe Leu Leu Ala Ala Ala
385                 390                 395                 400

Ala Phe Pro Asn Tyr Phe Phe Thr Gln Arg Gly Pro Tyr Ala Lys Glu
                405                 410                 415

Gly Trp Asp Tyr Ser Gln Val Ala Asp Val Ile Ser Ala His Ala Lys
            420                 425                 430

Pro Gly Asp Cys Leu Leu Val Asp Asn Thr Ala Gly Trp Arg Pro Gly
        435                 440                 445

Pro Ile Arg Ala Leu Leu Ala Thr Arg Pro Ala Ala Phe Arg Ser Leu
    450                 455                 460

Ile Asp Val Glu Arg Gly Thr Tyr Gly Pro Lys Val Gly Thr Leu Trp
465                 470                 475                 480

Asp Gly His Val Ala Val Trp Leu Thr Thr Ala Lys Ile Asp Lys Cys
                485                 490                 495

Pro Thr Leu Trp Thr Ile Ala Asn Arg Asp Lys Ser Leu Pro Asp His
            500                 505                 510

Gln Val Gly Glu Met Leu Ser Pro Gly Thr Gly Phe Gly Arg Thr Pro
        515                 520                 525

Val Tyr Arg Phe Pro Ser Tyr Leu Gly Phe Arg Ile Val Glu Arg Trp
    530                 535                 540

Gln Phe His Tyr Ser Gln Val Val Lys Ser Thr Arg
545                 550                 555


<210> SEQ ID NO 5
<211> LENGTH: 1284
<212> TYPE: DNA
<213> ORGANISM: Mycobacterium bovis
<220> FEATURE:
<221> NAME/KEY: CDS
<222> LOCATION: (1)..(1284)

<400> SEQUENCE: 5

atg agt gca tgg cgg gcg ccc gag gtg ggc agt cga ctc ggg cgg agg       48
Met Ser Ala Trp Arg Ala Pro Glu Val Gly Ser Arg Leu Gly Arg Arg
1               5                   10                  15

gtg ttg tgg tgc ctg ctg tgg ctg ctg gcc ggc gtg gcg ttg ggc tac       96
Val Leu Trp Cys Leu Leu Trp Leu Leu Ala Gly Val Ala Leu Gly Tyr
            20                  25                  30

gtg gcc tgg cgg ttg ttc ggc cac acg ccg tat cgc atc gat atc gac      144
Val Ala Trp Arg Leu Phe Gly His Thr Pro Tyr Arg Ile Asp Ile Asp
        35                  40                  45

atc tat cag atg ggc gct cga gct tgg ctg gac ggg cgt ccg ctg tat      192
Ile Tyr Gln Met Gly Ala Arg Ala Trp Leu Asp Gly Arg Pro Leu Tyr
    50                  55                  60

ggc ggt ggt gtg ttg ttc cac aca ccc atc ggg ctg aac ctc ccg ttc      240
Gly Gly Gly Val Leu Phe His Thr Pro Ile Gly Leu Asn Leu Pro Phe
65                  70                  75                  80

acc tat cct cca ctg gcg gcc gtc ctg ttc agc cca ttc gcc tgg ttg      288
Thr Tyr Pro Pro Leu Ala Ala Val Leu Phe Ser Pro Phe Ala Trp Leu
                85                  90                  95
```

-continued

```
cag atg ccg gct gcc agc gtc gcg atc acg gtg cta acc ctg gtg ctg      336
Gln Met Pro Ala Ala Ser Val Ala Ile Thr Val Leu Thr Leu Val Leu
            100                 105                 110

ctg atc gcg tcg acg gcg atc gtg ctg acc ggc ctc gac gca tgg cca      384
Leu Ile Ala Ser Thr Ala Ile Val Leu Thr Gly Leu Asp Ala Trp Pro
        115                 120                 125

acc tcc cga ctg gta ccc gcg ccg gct cgg tta cgc cgg ttg tgg ttg      432
Thr Ser Arg Leu Val Pro Ala Pro Ala Arg Leu Arg Arg Leu Trp Leu
    130                 135                 140

gcc gtg ctc atc gtg gct ccg gca acg att tgg ctg gag ccg atc agc      480
Ala Val Leu Ile Val Ala Pro Ala Thr Ile Trp Leu Glu Pro Ile Ser
145                 150                 155                 160

tcg aac ttc gct ttc ggt cag atc aat gtg gtg ctg atg acc ctg gtg      528
Ser Asn Phe Ala Phe Gly Gln Ile Asn Val Val Leu Met Thr Leu Val
                165                 170                 175

atc gtc gac tgc ttc cca cgc cga acg cca tgg cca cgc ggg ctg atg      576
Ile Val Asp Cys Phe Pro Arg Arg Thr Pro Trp Pro Arg Gly Leu Met
            180                 185                 190

ttg ggg ctg ggg ata gcc ctc aaa ctc acc ccc gcg gtg ttt ctc ctc      624
Leu Gly Leu Gly Ile Ala Leu Lys Leu Thr Pro Ala Val Phe Leu Leu
        195                 200                 205

tac ttc ctg cta cgt cgg gac ggt cgg gcc gcg ctg acg gcg ctg gcg      672
Tyr Phe Leu Leu Arg Arg Asp Gly Arg Ala Ala Leu Thr Ala Leu Ala
    210                 215                 220

tcg ttc gcg gtc gcc acg ctg ctc ggt ttc gtc ctg gcg tgg cgc gac      720
Ser Phe Ala Val Ala Thr Leu Leu Gly Phe Val Leu Ala Trp Arg Asp
225                 230                 235                 240

tcc tgg gag tac tgg acg cat acc ctt cac cac acg gac cgg atc ggc      768
Ser Trp Glu Tyr Trp Thr His Thr Leu His His Thr Asp Arg Ile Gly
                245                 250                 255

gct gcc gcc ttg aac aca gac cag aac atc gcg ggc gca ctc gcg cgg      816
Ala Ala Ala Leu Asn Thr Asp Gln Asn Ile Ala Gly Ala Leu Ala Arg
            260                 265                 270

ttg acg att ggc gat gac gaa cgc ttc gca ctg tgg gtg gcc gga tcc      864
Leu Thr Ile Gly Asp Asp Glu Arg Phe Ala Leu Trp Val Ala Gly Ser
        275                 280                 285

ctg ctc gtg ttg gca gcg acc ata tgg gcg atg cgg cga gtg ttg cgg      912
Leu Leu Val Leu Ala Ala Thr Ile Trp Ala Met Arg Arg Val Leu Arg
    290                 295                 300

gcc ggc gag ccg acc ctg gct gtg atc tgc gtc gcc ctg ttc ggg ttg      960
Ala Gly Glu Pro Thr Leu Ala Val Ile Cys Val Ala Leu Phe Gly Leu
305                 310                 315                 320

gta gtt tcg ccg gtc tcg tgg tca cac cat tgg gtg tgg atg ctg ccg     1008
Val Val Ser Pro Val Ser Trp Ser His His Trp Val Trp Met Leu Pro
                325                 330                 335

gcc gtg ctg gtg att ggg cta ctg ggt tgg cgt cgc cgc aac gtc gcg     1056
Ala Val Leu Val Ile Gly Leu Leu Gly Trp Arg Arg Arg Asn Val Ala
            340                 345                 350

ttg gcc atg ctc agc ctg gcc ggg gtg gtg ctg atg agg tgg aca ccg     1104
Leu Ala Met Leu Ser Leu Ala Gly Val Val Leu Met Arg Trp Thr Pro
        355                 360                 365

atc gac ctg ctt ccc caa cac cgg gag acg act gcg gtc tgg tgg cgt     1152
Ile Asp Leu Leu Pro Gln His Arg Glu Thr Thr Ala Val Trp Trp Arg
    370                 375                 380

caa ctc gcg ggg atg tcc tac gtg tgg tgg gcg ctg gcg gtc atc gtc     1200
Gln Leu Ala Gly Met Ser Tyr Val Trp Trp Ala Leu Ala Val Ile Val
385                 390                 395                 400

gtt gcc gga ctc acc gtt acc gcc agg atg acg ccg cag cgc tcg ctt     1248
Val Ala Gly Leu Thr Val Thr Ala Arg Met Thr Pro Gln Arg Ser Leu
                405                 410                 415
```

```
acg cgc gga ctg acc ccg gcg ccg acg gcc agc tga                    1284
Thr Arg Gly Leu Thr Pro Ala Pro Thr Ala Ser
            420                 425


<210> SEQ ID NO 6
<211> LENGTH: 427
<212> TYPE: PRT
<213> ORGANISM: Mycobacterium bovis

<400> SEQUENCE: 6

Met Ser Ala Trp Arg Ala Pro Glu Val Gly Ser Arg Leu Gly Arg Arg
1               5                   10                  15

Val Leu Trp Cys Leu Leu Trp Leu Leu Ala Gly Val Ala Leu Gly Tyr
            20                  25                  30

Val Ala Trp Arg Leu Phe Gly His Thr Pro Tyr Arg Ile Asp Ile Asp
        35                  40                  45

Ile Tyr Gln Met Gly Ala Arg Ala Trp Leu Asp Gly Arg Pro Leu Tyr
    50                  55                  60

Gly Gly Gly Val Leu Phe His Thr Pro Ile Gly Leu Asn Leu Pro Phe
65                  70                  75                  80

Thr Tyr Pro Pro Leu Ala Ala Val Leu Phe Ser Pro Phe Ala Trp Leu
                85                  90                  95

Gln Met Pro Ala Ala Ser Val Ala Ile Thr Val Leu Thr Leu Val Leu
            100                 105                 110

Leu Ile Ala Ser Thr Ala Ile Val Leu Thr Gly Leu Asp Ala Trp Pro
        115                 120                 125

Thr Ser Arg Leu Val Pro Ala Pro Ala Arg Leu Arg Arg Leu Trp Leu
    130                 135                 140

Ala Val Leu Ile Val Ala Pro Ala Thr Ile Trp Leu Glu Pro Ile Ser
145                 150                 155                 160

Ser Asn Phe Ala Phe Gly Gln Ile Asn Val Val Leu Met Thr Leu Val
                165                 170                 175

Ile Val Asp Cys Phe Pro Arg Arg Thr Pro Trp Pro Arg Gly Leu Met
            180                 185                 190

Leu Gly Leu Gly Ile Ala Leu Lys Leu Thr Pro Ala Val Phe Leu Leu
        195                 200                 205

Tyr Phe Leu Leu Arg Arg Asp Gly Arg Ala Ala Leu Thr Ala Leu Ala
    210                 215                 220

Ser Phe Ala Val Ala Thr Leu Leu Gly Phe Val Leu Ala Trp Arg Asp
225                 230                 235                 240

Ser Trp Glu Tyr Trp Thr His Thr Leu His His Thr Asp Arg Ile Gly
                245                 250                 255

Ala Ala Ala Leu Asn Thr Asp Gln Asn Ile Ala Gly Ala Leu Ala Arg
            260                 265                 270

Leu Thr Ile Gly Asp Asp Glu Arg Phe Ala Leu Trp Val Ala Gly Ser
        275                 280                 285

Leu Leu Val Leu Ala Ala Thr Ile Trp Ala Met Arg Arg Val Leu Arg
    290                 295                 300

Ala Gly Glu Pro Thr Leu Ala Val Ile Cys Val Ala Leu Phe Gly Leu
305                 310                 315                 320

Val Val Ser Pro Val Ser Trp Ser His His Trp Val Trp Met Leu Pro
                325                 330                 335

Ala Val Leu Val Ile Gly Leu Leu Gly Trp Arg Arg Arg Asn Val Ala
            340                 345                 350

Leu Ala Met Leu Ser Leu Ala Gly Val Val Leu Met Arg Trp Thr Pro
```

```
        355                 360                 365

Ile Asp Leu Leu Pro Gln His Arg Glu Thr Thr Ala Val Trp Trp Arg
    370                 375                 380

Gln Leu Ala Gly Met Ser Tyr Val Trp Trp Ala Leu Ala Val Ile Val
385                 390                 395                 400

Val Ala Gly Leu Thr Val Thr Ala Arg Met Thr Pro Gln Arg Ser Leu
                405                 410                 415

Thr Arg Gly Leu Thr Pro Ala Pro Thr Ala Ser
            420                 425


<210> SEQ ID NO 7
<211> LENGTH: 1551
<212> TYPE: DNA
<213> ORGANISM: Mycobacterium bovis
<220> FEATURE:
<221> NAME/KEY: CDS
<222> LOCATION: (1)..(1551)

<400> SEQUENCE: 7

atg act act ccg agc cat gct cca gcg gtt gat ttg gct aca gcg aaa       48
Met Thr Thr Pro Ser His Ala Pro Ala Val Asp Leu Ala Thr Ala Lys
1               5                   10                  15

gat gct gtt gtc caa cac ctt tcg cga ctt ttc gag ttc act acc ggt       96
Asp Ala Val Val Gln His Leu Ser Arg Leu Phe Glu Phe Thr Thr Gly
            20                  25                  30

ccg cag ggc gga ccg gcg cgg ctg ggc ttc gcc ggc gcg gtg ctg atc      144
Pro Gln Gly Gly Pro Ala Arg Leu Gly Phe Ala Gly Ala Val Leu Ile
        35                  40                  45

acc gca ggc ggg ctg gga gcc ggc agc gtc cgc caa cat gac ccg ctg      192
Thr Ala Gly Gly Leu Gly Ala Gly Ser Val Arg Gln His Asp Pro Leu
    50                  55                  60

ctg gag tcg att cac atg tcc tgg ctg cgc ttc ggc cac gga ctc gtg      240
Leu Glu Ser Ile His Met Ser Trp Leu Arg Phe Gly His Gly Leu Val
65                  70                  75                  80

ctg tcg tcg att ctg ttg tgg aca ggt gtg ggt gtg atg ctg ctt gcg      288
Leu Ser Ser Ile Leu Leu Trp Thr Gly Val Gly Val Met Leu Leu Ala
                85                  90                  95

tgg ctg ggt cta ggc cga cgg gtc ctc gcc ggc gaa gcc acc gag ttc      336
Trp Leu Gly Leu Gly Arg Arg Val Leu Ala Gly Glu Ala Thr Glu Phe
            100                 105                 110

acc atg cgg gca acc acc gtt atc tgg ctg gcg ccg cta ctg ctg tcg      384
Thr Met Arg Ala Thr Thr Val Ile Trp Leu Ala Pro Leu Leu Leu Ser
        115                 120                 125

gtg ccc gtc ttc agc cgg gac act tac tcg tat ctg gcc caa ggg gcg      432
Val Pro Val Phe Ser Arg Asp Thr Tyr Ser Tyr Leu Ala Gln Gly Ala
    130                 135                 140

ctt ctg cgc gac ggt ctg gat cct tac gct gtt ggc ccg gtc ggt aat      480
Leu Leu Arg Asp Gly Leu Asp Pro Tyr Ala Val Gly Pro Val Gly Asn
145                 150                 155                 160

ccc aat gcg ctg ctg gac gac gta agc ccg atc tgg acg atc acc acc      528
Pro Asn Ala Leu Leu Asp Asp Val Ser Pro Ile Trp Thr Ile Thr Thr
                165                 170                 175

gcg ccc tac ggt cct gcg ttc att ctg gtt gcg aag ttc gtc acg gta      576
Ala Pro Tyr Gly Pro Ala Phe Ile Leu Val Ala Lys Phe Val Thr Val
            180                 185                 190

atc gtc ggc aac aat gtc gtc gcc gga acc atg ctg ttg cgt ttg tgc      624
Ile Val Gly Asn Asn Val Val Ala Gly Thr Met Leu Leu Arg Leu Cys
        195                 200                 205

atg ctg ccc ggg ctg gcg ttg ctg gtc tgg gcc act cca cgc ttg gcc      672
Met Leu Pro Gly Leu Ala Leu Leu Val Trp Ala Thr Pro Arg Leu Ala
    210                 215                 220
```

```
agc cat ctc ggc acc cac ggc ccg acc gcg ctg tgg atc tgc gtg ctg      720
Ser His Leu Gly Thr His Gly Pro Thr Ala Leu Trp Ile Cys Val Leu
225                 230                 235                 240

aac cca ctg gtc ctc atc cat ctg atg ggc ggg gtg cac aac gag atg      768
Asn Pro Leu Val Leu Ile His Leu Met Gly Gly Val His Asn Glu Met
                245                 250                 255

ctg atg gtg ggt ctg atg acc gcc ggt atc gcg ttg acc gtc cag ggc      816
Leu Met Val Gly Leu Met Thr Ala Gly Ile Ala Leu Thr Val Gln Gly
            260                 265                 270

cgt aat gtc gcg ggg atc atc ctg atc acc gtt gcg atc gcg gtg aag      864
Arg Asn Val Ala Gly Ile Ile Leu Ile Thr Val Ala Ile Ala Val Lys
        275                 280                 285

gcc acc gcc gga atc gcg ttg ccc ttc ttg gtc tgg gtt tgg ctg cgt      912
Ala Thr Ala Gly Ile Ala Leu Pro Phe Leu Val Trp Val Trp Leu Arg
    290                 295                 300

cat ctg cgt gag cga cgg ggg tac cgg ccg gtc cag gcg ttc ctg gca      960
His Leu Arg Glu Arg Arg Gly Tyr Arg Pro Val Gln Ala Phe Leu Ala
305                 310                 315                 320

gcc gcc gcg ata tcg ctg ctg atc ttc gtc gcg gtg ttc gcg gtg ctg     1008
Ala Ala Ala Ile Ser Leu Leu Ile Phe Val Ala Val Phe Ala Val Leu
                325                 330                 335

tct gcg gta gcc ggc gtt ggc cta ggg tgg ctg acc gcg ctg gcc ggc     1056
Ser Ala Val Ala Gly Val Gly Leu Gly Trp Leu Thr Ala Leu Ala Gly
            340                 345                 350

tcg gtg aaa atc atc aac tgg ctg acg gtg ccc acc ggg gcg gcc aac     1104
Ser Val Lys Ile Ile Asn Trp Leu Thr Val Pro Thr Gly Ala Ala Asn
        355                 360                 365

gtg atc cac gcg ctg ggc aga ggg ctc ttc acg gtc gac ttc tac acc     1152
Val Ile His Ala Leu Gly Arg Gly Leu Phe Thr Val Asp Phe Tyr Thr
    370                 375                 380

ttg ctg cgg atc acc cgg ctg atc gga atc gtg atc atc gcg gtg tcg     1200
Leu Leu Arg Ile Thr Arg Leu Ile Gly Ile Val Ile Ile Ala Val Ser
385                 390                 395                 400

ctg ccg ctg ttg tgg tgg cgg ttc cgg cgc gac gac cgg gcc gcg ctg     1248
Leu Pro Leu Leu Trp Trp Arg Phe Arg Arg Asp Asp Arg Ala Ala Leu
                405                 410                 415

acc ggg gtc gca tgg tcg atg ctg atc gtg gtg ctg ttc gta ccc gcc     1296
Thr Gly Val Ala Trp Ser Met Leu Ile Val Val Leu Phe Val Pro Ala
            420                 425                 430

gcc ctg ccg tgg tac tac tcc tgg ccg ctg gcg gtc gct gcc ccg ttg     1344
Ala Leu Pro Trp Tyr Tyr Ser Trp Pro Leu Ala Val Ala Ala Pro Leu
        435                 440                 445

gcc cag tca cga cgg gcg atc gcg gcc atc gcc ggg ctc tcg act tgg     1392
Ala Gln Ser Arg Arg Ala Ile Ala Ala Ile Ala Gly Leu Ser Thr Trp
    450                 455                 460

gtg atg gtg atc ttc aaa ccc gac gga tcg cac ggg atg tat tcg tgg     1440
Val Met Val Ile Phe Lys Pro Asp Gly Ser His Gly Met Tyr Ser Trp
465                 470                 475                 480

ctg cac ttc tgg atc gcc acc gcc tgc gca ctg act gcg tgg tat gtc     1488
Leu His Phe Trp Ile Ala Thr Ala Cys Ala Leu Thr Ala Trp Tyr Val
                485                 490                 495

ctg tat cgg tca ccg gac cgg cgc gga gtg cag gct gca acc ccg gtg     1536
Leu Tyr Arg Ser Pro Asp Arg Arg Gly Val Gln Ala Ala Thr Pro Val
            500                 505                 510

gtc aat acg cca tag                                                 1551
Val Asn Thr Pro
        515
```

<210> SEQ ID NO 8
<211> LENGTH: 516

<212> TYPE: PRT
<213> ORGANISM: Mycobacterium bovis

<400> SEQUENCE: 8

```
Met Thr Thr Pro Ser His Ala Pro Ala Val Asp Leu Ala Thr Ala Lys
1               5                   10                  15

Asp Ala Val Val Gln His Leu Ser Arg Leu Phe Glu Phe Thr Thr Gly
            20                  25                  30

Pro Gln Gly Gly Pro Ala Arg Leu Gly Phe Ala Gly Ala Val Leu Ile
        35                  40                  45

Thr Ala Gly Gly Leu Gly Ala Gly Ser Val Arg Gln His Asp Pro Leu
    50                  55                  60

Leu Glu Ser Ile His Met Ser Trp Leu Arg Phe Gly His Gly Leu Val
65                  70                  75                  80

Leu Ser Ser Ile Leu Leu Trp Thr Gly Val Gly Val Met Leu Leu Ala
                85                  90                  95

Trp Leu Gly Leu Gly Arg Arg Val Leu Ala Gly Glu Ala Thr Glu Phe
            100                 105                 110

Thr Met Arg Ala Thr Thr Val Ile Trp Leu Ala Pro Leu Leu Leu Ser
        115                 120                 125

Val Pro Val Phe Ser Arg Asp Thr Tyr Ser Tyr Leu Ala Gln Gly Ala
    130                 135                 140

Leu Leu Arg Asp Gly Leu Asp Pro Tyr Ala Val Gly Pro Val Gly Asn
145                 150                 155                 160

Pro Asn Ala Leu Leu Asp Asp Val Ser Pro Ile Trp Thr Ile Thr Thr
                165                 170                 175

Ala Pro Tyr Gly Pro Ala Phe Ile Leu Val Ala Lys Phe Val Thr Val
            180                 185                 190

Ile Val Gly Asn Asn Val Val Ala Gly Thr Met Leu Leu Arg Leu Cys
        195                 200                 205

Met Leu Pro Gly Leu Ala Leu Leu Val Trp Ala Thr Pro Arg Leu Ala
    210                 215                 220

Ser His Leu Gly Thr His Gly Pro Thr Ala Leu Trp Ile Cys Val Leu
225                 230                 235                 240

Asn Pro Leu Val Leu Ile His Leu Met Gly Gly Val His Asn Glu Met
                245                 250                 255

Leu Met Val Gly Leu Met Thr Ala Gly Ile Ala Leu Thr Val Gln Gly
            260                 265                 270

Arg Asn Val Ala Gly Ile Ile Leu Ile Thr Val Ala Ile Ala Val Lys
        275                 280                 285

Ala Thr Ala Gly Ile Ala Leu Pro Phe Leu Val Trp Val Trp Leu Arg
    290                 295                 300

His Leu Arg Glu Arg Arg Gly Tyr Arg Pro Val Gln Ala Phe Leu Ala
305                 310                 315                 320

Ala Ala Ala Ile Ser Leu Leu Ile Phe Val Ala Val Phe Ala Val Leu
                325                 330                 335

Ser Ala Val Ala Gly Val Gly Leu Gly Trp Leu Thr Ala Leu Ala Gly
            340                 345                 350

Ser Val Lys Ile Ile Asn Trp Leu Thr Val Pro Thr Gly Ala Ala Asn
        355                 360                 365

Val Ile His Ala Leu Gly Arg Gly Leu Phe Thr Val Asp Phe Tyr Thr
    370                 375                 380

Leu Leu Arg Ile Thr Arg Leu Ile Gly Ile Val Ile Ile Ala Val Ser
385                 390                 395                 400
```

-continued

```
Leu Pro Leu Leu Trp Trp Arg Phe Arg Arg Asp Asp Arg Ala Ala Leu
                405                 410                 415

Thr Gly Val Ala Trp Ser Met Leu Ile Val Val Leu Phe Val Pro Ala
            420                 425                 430

Ala Leu Pro Trp Tyr Tyr Ser Trp Pro Leu Ala Val Ala Ala Pro Leu
        435                 440                 445

Ala Gln Ser Arg Arg Ala Ile Ala Ala Ile Ala Gly Leu Ser Thr Trp
    450                 455                 460

Val Met Val Ile Phe Lys Pro Asp Gly Ser His Gly Met Tyr Ser Trp
465                 470                 475                 480

Leu His Phe Trp Ile Ala Thr Ala Cys Ala Leu Thr Ala Trp Tyr Val
                485                 490                 495

Leu Tyr Arg Ser Pro Asp Arg Arg Gly Val Gln Ala Ala Thr Pro Val
            500                 505                 510

Val Asn Thr Pro
        515


<210> SEQ ID NO 9
<211> LENGTH: 22
<212> TYPE: DNA
<213> ORGANISM: Artificial
<220> FEATURE:
<223> OTHER INFORMATION: oligonucleotide

<400> SEQUENCE: 9

gacgtgggcc ggaatcgaag ca                                               22


<210> SEQ ID NO 10
<211> LENGTH: 24
<212> TYPE: DNA
<213> ORGANISM: Artificial
<220> FEATURE:
<223> OTHER INFORMATION: oligonucleotide

<400> SEQUENCE: 10

gatccacccg acctgccaaa cctg                                             24


<210> SEQ ID NO 11
<211> LENGTH: 21
<212> TYPE: DNA
<213> ORGANISM: Artificial
<220> FEATURE:
<223> OTHER INFORMATION: oligonucleotide

<400> SEQUENCE: 11

aacgcttcgc actgtgggtg g                                                21


<210> SEQ ID NO 12
<211> LENGTH: 24
<212> TYPE: DNA
<213> ORGANISM: Artificial
<220> FEATURE:
<223> OTHER INFORMATION: oligonucleotide

<400> SEQUENCE: 12

cgtaggacat ccccgcgagt tgac                                             24


<210> SEQ ID NO 13
<211> LENGTH: 21
<212> TYPE: DNA
<213> ORGANISM: Artificial
<220> FEATURE:
<223> OTHER INFORMATION: oligonucleotide
```

<400> SEQUENCE: 13
acacacccga gcgaaccgaa c 21

<210> SEQ ID NO 14
<211> LENGTH: 24
<212> TYPE: DNA
<213> ORGANISM: Artificial
<220> FEATURE:
<223> OTHER INFORMATION: oligonucleotide

<400> SEQUENCE: 14
caagcggatg ggtacgaggt cagc 24

<210> SEQ ID NO 15
<211> LENGTH: 24
<212> TYPE: DNA
<213> ORGANISM: Artificial
<220> FEATURE:
<223> OTHER INFORMATION: oligonucleotide

<400> SEQUENCE: 15
gatgggcggg gtgcacaacg agat 24

<210> SEQ ID NO 16
<211> LENGTH: 23
<212> TYPE: DNA
<213> ORGANISM: Artificial
<220> FEATURE:
<223> OTHER INFORMATION: oligonucleotide

<400> SEQUENCE: 16
cacgcagatg acgcagccaa acc 23

<210> SEQ ID NO 17
<211> LENGTH: 21
<212> TYPE: DNA
<213> ORGANISM: Artificial
<220> FEATURE:
<223> OTHER INFORMATION: oligonucleotide

<400> SEQUENCE: 17
atgacggcct tcgggttgta a 21

<210> SEQ ID NO 18
<211> LENGTH: 20
<212> TYPE: DNA
<213> ORGANISM: Artificial
<220> FEATURE:
<223> OTHER INFORMATION: oligonucleotide

<400> SEQUENCE: 18
cggctgctgg cacgtagttg 20

<210> SEQ ID NO 19
<211> LENGTH: 20
<212> TYPE: DNA
<213> ORGANISM: Artificial
<220> FEATURE:
<223> OTHER INFORMATION: oligonucleotide

<400> SEQUENCE: 19
caccacggtc ttataggcgc 20

<210> SEQ ID NO 20
<211> LENGTH: 16
<212> TYPE: DNA

-continued

```
<213> ORGANISM: Artificial
<220> FEATURE:
<223> OTHER INFORMATION: oligonucleotide

<400> SEQUENCE: 20

ccgttcacct ccactg                                                  16


<210> SEQ ID NO 21
<211> LENGTH: 21
<212> TYPE: DNA
<213> ORGANISM: Artificial
<220> FEATURE:
<223> OTHER INFORMATION: oligonucleotide

<400> SEQUENCE: 21

atcgtggctc ggtcccctaa a                                            21


<210> SEQ ID NO 22
<211> LENGTH: 20
<212> TYPE: DNA
<213> ORGANISM: Artificial
<220> FEATURE:
<223> OTHER INFORMATION: oligonucleotide

<400> SEQUENCE: 22

cggtgacgac ctaaagtcgg                                              20
```

MYCOBACTERIUM MUTANTS FOR VACCINES WITH IMPROVED PROTECTIVE EFFICACY

CROSS-REFERENCE TO RELATED APPLICATIONS

This is a national phase entry under 35 U.S.C. §371 of International Patent Application PCT/EP2010/060986, filed Jul. 28, 2010, published in English as International Patent Publication WO 2011/012662 A1 on Feb. 3, 2011, which claims the benefit, both under Article 8 of the Patent Cooperation Treaty and under 35 U.S.C. §119(e) to U.S. Provisional Patent Application Ser. No. 61/229,062 filed Jul. 28, 2009.

TECHNICAL FIELD

The present invention relates to the field of vaccines, most particularly, live attenuated *Mycobacterium*-based vaccines. Disclosed herein are genes that, when mutated in mycobacteria used for immunization of animals, particularly mammals, confer improved protective efficacy as a vaccine against a *Mycobacterium* infection, while not interfering with the beneficial properties of known vaccination strains such as *Mycobacterium bovis* BCG. Such vaccines are particularly suitable against *Mycobacterium tuberculosis* infection.

BACKGROUND

One-third of the world's population is infected with *Mycobacterium tuberculosis* (M. tb), the etiologic agent of TB. The World Health Organization estimates that about eight to ten million new TB cases occur annually worldwide and the incidence of TB is currently increasing. Together with malaria and HIV-AIDS, TB is one of the three leading causes of death from a single infectious agent, and approximately two million deaths are attributable to TB annually (WHO Report, 2008). The only currently licensed vaccine is *Mycobacterium bovis* Bacille Calmette-Guerin (*M. bovis* BCG), an attenuated strain of *M. bovis*, which has been administered to over four billion people over the years since 1921, when it was first used. When administered at birth, *M. bovis* BCG confers consistent and reliable protection against disseminated disease in the first ten years of life (Rodrigues et al., 1993). However, the protection conferred against pulmonary disease in adolescents and adults is much more variable (Colditz et al., 1994). The main current approach in developing improved prophylactic TB vaccines is to use modified *M. bovis* BCG or *M. tb* to improve upon *M. bovis* BCG as a priming vaccine, possibly followed by boosting some time later with selected immunodominant antigens as a protein or viral vector vaccine (Barker et al., 2009; STOP-TB Partnership, 2009).

In the case of *tuberculosis*, alveolar macrophages successfully phagocytose *M. tb* and are the primary site of infection. However, the mycobacteria interfere with phagosomal maturation, thus enabling the mycobacteria to partially evade many of the immune mechanisms that would otherwise eliminate them.[50] The bacterial genes and pathways that are essential for the intracellular growth and survival of *M. tb* are attractive drug targets and several of such bacterial virulence mechanisms have been suggested.[13, 14] However, the functional validation of the bacterial components suspected to be involved in *M. tb* host interactions requires the generation of mutants. These critical experiments are hampered by the slow growth and poor homologous recombination efficiency of *M. tb*[39] and by the requirement to work in costly high-biosafety laboratories. The combination of these features makes mutant generation a very lengthy, cumbersome and expensive process. Therefore, many researchers resort to non-pathogenic fast-growing mycobacterial species to generate mutants, with results that are not necessarily to be extrapolated to their slow-growing cousins.[24] The attenuated vaccine strain *M. bovis* BCG is a more faithful, yet safer model organism for many aspects of *M. tb* host interactions.[8, 17] It is also slow growing and is genomically extremely similar to *M. tuberculosis* (>99%), only lacking a small number of genomic regions, of which the RD1 locus has primarily resulted in its attenuation.[2, 33] Each BCG strain has multiple deletions, of which only the RD1 locus is common to all.

It should be noted that the unusual cell wall of mycobacteria is one of the factors that enable the mycobacteria to successfully colonize their host. The cell wall is composed of a complex of lipids, glycolipids and proteins that interact with macrophages.[5] One such cell envelope component is lipoarabinomannan (LAM), which, along with its precursors lipomannan (LM) and phosphatidyl-myo-inositol mannosides (PIMs), is noncovalently anchored to the plasma membrane. LAM contains a mannosylphosphatidyl-myo-inositol anchor (MPI), a mannan core and long, substituted arabinan branches. The mannan backbone consists of $\alpha$-1,6-linked mannose units with single residue $\alpha$-1,2-Manp substitutions. The arabinan polymer is composed of $\alpha$-1,5-linked Araf units and is substituted with branched hexa-arabinofuranosides and linear tetra-arabinofuranosides. The non-reducing termini of these arabinan side-chains terminate in cap motifs. In slow-growing pathogenic strains, these motifs consist of one, two or three $\alpha$-1,2-linked Manp residues with the dimannoside being the most abundant. In contrast, in non-pathogenic strains, there are usually inositol phosphate caps (PILAM in *M. smegmatis*) or no caps at all (AraLAM in *M. chelonae*).[7] ManLAM (mannosylated lipoarabinomannan) has been reported to play a role in subverting host cell signaling pathways[18] and blocking phagosome maturation[15] in host macrophages.

LAM is built from phosphatidyl-myo-inositol (PI), the synthesis of which requires the activity of the diacylglycerol kinase Mb2276.[45] PI undergoes a series of sequential $\alpha$-mannosylations, catalyzed by PimA (Mb2642c), PimB (Mb0572), PimC (Mb 1785c) and PimF (Mb1538).[25, 26, 38, 57] The glycosyl donor substrate for all mannosylations in ManLAM synthesis from PI is polyprenol phosphomannose, which is synthesized from GDP-mannose by the polyprenol phosphomannose synthase ppm1 (Mb2077c).[19] GDP-mannose synthesis in this process involves the phosphomannose mutase pmmB (Mb3336).[55] LM is synthesized on the PIM4 precursor by the addition of a linear $\alpha$-1,6-mannose polymer of 21-34 residues. The mannosyltransferase Mb2196 is required for this modification.[23] A previous study showed that Rv2181 (Mb2203) is the mannosyltransferase responsible for the addition of single $\alpha$-1,2-Manp residues to the mannan core of LM/LAM.[20] In this latter study, the inactivation of the corresponding homologue in *M. smegmatis* leads to the production of a truncated LAM and the absence of LM. However, more recent data reveal that a similar inactivation in *M. tb* leads to production of lower molecular weight LAM, but does not affect the synthesis of LM, revealing a role for this mannosyltransferase in the terminal capping of LAM.[24] LAM is derived from LM through the addition of poly $\alpha$-1,5-araf chains, the synthesis of which requires embC.[4, 65] The transcription of embC is regulated by the serine threonine kinase pknH via the phosphorylation of the transcriptional regulator EmbR.[59] The linear arabinan branches are further substituted with hexa- and tetra-arabinofuranoside structures. These non-reducing arabinan termini of the LAM are capped in *M. tuberculosis* and *M. bovis* BCG, to varying degrees, with one to three (α-1,2)-Manp residues. The first mannosyltransferase involved in this α-1,2-mannose capping is encoded by Rv1635c and its homologue in *M. bovis* BCG, Mb 1661c.[11] While the gene Mb1661c is likely responsible for the addition of the first mannose residue of the cap, the mannosyltransferase Mb2203 is thought to add the additional one or two mannose residues to generate di- and tri-Manp capped LAM.[24] Other factors influencing the virulence of *M. tb* include the lipoprotein signal peptidase, LspA (Mb1566),[53] the lipid phosphatase SapM (Mb3338),[42] and the Zn metalloprotease Zmp1 (Mb0204c).[35]

Most work in the *tuberculosis* vaccine field is directed by the belief that BCG is "missing something of *M. tuberculosis*" and that this either has to be added back to BCG to improve vaccine-induced protection, or that, conversely, *M. tb* should be attenuated to the low virulence of BCG while keeping its immunodominant antigens. Examples of the former are recombinant BCG strains overexpressing immunodominant *M. tb* antigens (Castanon-Arreola et al., 2005; Horwitz & Harth, 2003; Pym et al., 2003) and examples of the latter are virulence factor (Copenhaver et al., 2004), auxotrophic (Sambandamurthy et al., 2005; Sambandamurthy et al., 2002) or signal transduction (Martin et al., 2006) mutants of *M. tb*. Moreover, improved induction of phagosome maturation and apoptosis in phagocytes (Grode et al., 2005; Hinchey et al., 2007; Sadagopal et al., 2009; Sun et al., 2009; Velmurugan et al., 2007) is pursued to increase cross-presentation and therewith, vaccine efficiency. However, of all the engineered live vaccines, in direct comparisons with BCG vaccine, only five have been demonstrated to be sufficiently promising in experimental animals to be moved forward to Phase I clinical trials (STOP-TB Partnership, 2009): BCG overexpressing antigen 85b (rBCG30 prolonged survival in guinea pigs) (Horwitz & Harth, 2003); the urease C-deficient listeriolysin-secreting recombinant BCG (Grode et al., 2005; Tchilian et al., 2009) (ΔureC hly+ rBCG decreased CFU counts in lungs of mice), the urease C-deficient perfringiolysin-secreting recombinant BCG (Sun et al., 2009) (safer than BCG in SCID mouse study), the phoP mutant of *M. tuberculosis* (Martin et al., 2006; Verreck et al., 2009) (prolonged survival in guinea pigs, under high-dose challenge, while equal protection against low-dose challenge, and equal protection in mice; decreased CFU counts in lungs of rhesus macaques) and the secA2 mutant of *M. tuberculosis* (Hinchey et al., 2007; Sadagopal et al., 2009) (prolonged survival in mice). As *M. bovis* BCG is a live vaccine, there are regulatory and safety concerns toward transgenic strains being implemented at the massive scale, which is relevant for TB protection (e.g., transgene stability; risk for horizontal gene transfer of the transgene between the vaccine and *M. tb* itself (Krzywinska et al., 2004); different deliberate environmental release GMO regulations throughout the world) (Kamath et al., 2005; Walker et al., 2010). There are also potential safety issues with attenuated *M. tb* as a vaccine, and special precautions have to be taken (such as double mutations, with each single mutation resulting in sufficient attenuation) (Kamath et al., 2005; Walker et al., 2010). If a *M. bovis* BCG strain with better protective capability than the licensed strain BCG itself could be found in which the improved protection was brought about by targeted inactivation of endogenous genes rather than expressing heterologous transgenes, these concerns would be reduced and clinical implementation and public acceptance would be more straightforward.

DISCLOSURE

It was reasoned that mutation of mycobacterial components reportedly involved in phagosome maturation inhibition may yield better vaccines, as such mutations should result in better vaccine antigen processing and display. To this effect, an ordered *M. bovis* BCG transposon insertion mutant library was generated and mutants in 15 genes were identified, amongst which are two genes necessary for the alpha-1,2-oligomannosyl capping of cell wall ManLAM (Fratti et al., 2003; Hmama et al., 2004; Kang et al., 2005) and the PI3P phosphatase gene SapM.[21] Capping of LAM with α-1,2-oligomannosyl structures was, until recently, thought to be mainly mediated by the Rv1635c (Mb1661c)-encoded α-1,2-mannosyltransferase (Dinadayala et al., 2006). However, recent findings by Kaur and colleagues and in our laboratory demonstrate that another mannosyl-transferase (Rv2181 or Mb2203) is actually more selectively affecting the α-1,2-oligomannosyl cap structure synthesis, leaving the LAM levels in the cell wall intact (Kaur et al., 2006; Kaur et al., 2008). Therefore, this mutant is more suitable to address the specific role of α-1,2-oligomannosyl capping than the Mb1661c mutant (Appelmelk et al., 2008), which might have an altered cell wall composition compensating to the LAM deficiency. As ManLAM (mannosylated lipoarabinomannan) has been reported to play a role in subverting host cell signaling pathways[18] and blocking phagosome maturation[15] in host macrophages, mutants in the synthesis of ManLAM in slow-growing *mycobacterium* such as *M. bovis* BCG are of interest.

Both ManLAM capping and SapM were assigned important functions in phagosome maturation inhibition, but this has been disputed for ManLAM capping upon mutant studies[22] and has not yet been validated through mutant studies for SapM. In addition, the proposed LM α-1,6-mannosyltransferase Mb2196, which, so far, was not studied in slow-growing Mycobacteria, has now for the first time been biochemically characterized. These transposon insertion mutants of *M. bovis* BCG were evaluated as TB vaccines in a stringent model and it could be shown that they all have surprisingly improved vaccine efficacy, with the SapM::T mutant vaccines showing the longest survival. The mutant BCG strains showed unaltered uptake by macrophages and dendritic cells and lysosome colocalization in macrophages in vitro. In addition, their replication and granuloma formation in mice was comparable to *M. bovis* BCG wild-type, indicating BCG-equivalent safety of these vaccines. Vaccination with the SapM locus mutant significantly increases recruitment of $CD11c^{+}CD40^{+}$ MHC-$II^{lo/med}$ $CD8\alpha^{-}$ DCs to the draining lymph nodes and their activation, explaining an improved immune response. Further exploration of the mechanism evoking the improved vaccine efficiency of the mutants showed that the latter induced similar oxidant activity and autophagy following infection of macrophages compared to wild-type BCG.

Thus, according to a first aspect, a *mycobacterium* is provided comprising a genetically engineered mutation in at least one endogenous gene selected from SapM, the endogenous ManLAM α-1,2-mannosyltransferase corresponding to Mb1661c in *Mycobacterium bovis*, the endogenous ManLAM α-1,2-mannosyltransferase corresponding to Mb2203 in *Mycobacterium bovis* and the endogenous LM α-1,6-mannosyltransferase corresponding to Mb2196 in *Mycobacterium bovis*. These ManLAM α-1,2-mannosyltransferases are also equivalent to Rv1635c and Rv2181, respectively, in the *Mycobacterium tuberculosis* H37Rv strain. According to specific embodiments, the genetically engineered mutation (i.e., mutation obtained by genetic engineering methods) is a non-naturally occurring mutation. According to particular embodiments, combinations of the mentioned genes are mutated and/or an endogenous gene contains more than one mutation. According to specific embodiments, the genetically engineered mutation encodes a gene product that has a reduced (knock-down) or absent (knock-out) functionality. This may be either because there is none or less of the gene product present than in the corresponding wild-type strain, and/or because the gene product is not or only partially functional. According to particular embodiments, the genetically engineered mutation is created by insertion mutagenesis.

According to specific embodiments, the *mycobacterium* may have further mutations as well. According to even more specific embodiments, the *mycobacterium* also comprises at least one mutation that decreases virulence. According to alternative, but not exclusive, embodiments, the *mycobacterium* also comprises at least one mutation in an endogenous antioxidant gene. According to further embodiments, the endogenous antioxidant gene is selected from secA2, sigH and SodA (Sadagopal et al., 2009).

According to particular embodiments, the endogenous SapM gene, the ManLAM α-1,2-mannosyltransferase corresponding to the Mb1661c gene, the ManLAM α-1,2-mannosyltransferase corresponding to the Mb2203 gene or the LM α-1,6-mannosyltransferase corresponding to the Mb2196 gene comprises SEQ ID NOS:1, 3, 5, or 7, contiguous portions thereof, or sequences at least 95%, at least 98%, or at least 99% identical thereto, respectively; or comprises a sequence encoding SEQ ID NOS:2, 4, 6, or 8, contiguous portions thereof, or encoding sequences at least 95%, at least 98%, or at least 99% identical thereto, respectively.

According to specific embodiments, the mycobacteria described herein are selected from *Mycobacterium tuberculosis, Mycobacterium bovis* or *M. bovis* Bacille Calmette-Guérin (BCG).

According to very specific embodiments, the *mycobacterium* is selected from the deposited strains LMG P-25310, LMG P-25309, LMG P-25308, and LMG P-25441.

In a further aspect, uses of a *mycobacterium* as described herein, or of a portion thereof, are provided for the preparation of a recombinant vaccine, particularly a vaccine against *tuberculosis*. According to particular embodiments, the vaccine is a *M. bovis, M. bovis* Bacille Calmette-Guérin (BCG), or *M. tuberculosis*-based vaccine. According to alternative (but not exclusive) particular embodiments, the vaccine comprises a live attenuated vaccine.

Thus, methods are also provided for preparing a vaccine (or vaccine composition), comprising the step of generating a vaccine, e.g., by providing a live attenuated *mycobacterium* strain in a pharmaceutically acceptable carrier.

According to yet a further aspect, vaccines are provided comprising a *mycobacterium* as described herein, thus with a genetically engineered mutation in at least one endogenous gene selected from SapM, the endogenous ManLAM α-1,2-mannosyltransferase corresponding to Mb1661c in *Mycobacterium bovis*, the endogenous ManLAM α-1,2-mannosyltransferase corresponding to Mb2203 in *Mycobacterium bovis*, and the endogenous LM α-1,6-mannosyltransferase corresponding to Mb2196 in *Mycobacterium bovis*, in a pharmaceutically acceptable carrier or excipient. According to an alternative embodiment, the vaccines comprise a portion of the *mycobacterium*.

The vaccine may be useful in the treatment of several diseases, as recombinant *mycobacterium*-based vaccines are known to be excellent carrier vaccines (Bastos et al., 2009, particularly the tables therein). According to most specific embodiments, the vaccine is a vaccine against *tuberculosis*. In other words, the vaccine is suitable to protect an animal, most particularly a mammal, from challenge by a virulent *mycobacterium* selected from *M. bovis* or *M. tuberculosis*. Mammals may, for instance, be selected from humans (in particular, human children) or bovines, particularly cows.

According to particular embodiments, the vaccine is a live attenuated vaccine.

Thus, according to a particular aspect, the *mycobacterium* as described herein is provided for use in treatment of *tuberculosis*. According to further embodiments, the vaccine as described herein is provided for use in treatment of *tuberculosis*. Thus, methods are provided of protecting a mammal from a virulent *Mycobacterium* infection, particular from *Mycobacterium tuberculosis* or *M. bovis*, comprising treating the mammal with a vaccine as described herein (or possibly with a live attenuated *mycobacterium* as described herein). Alternatively, methods are provided of inducing an immune response in a mammal, the method comprising inoculating the mammal with the *mycobacterium* as described herein or the vaccine as described herein.

Panel A: The transposon insertion mutant library was created using the donor phagemid ΦMycomarT7. This phagemid includes a transposon that encodes a kanamycin resistance gene, T7 promoters oriented so as to promote transcription into adjacent chromosomal DNA and terminal 29-bp inverted repeats. This construct integrates into the mycobacterial genome theoretically after every "TA." Panel B: Individual mutants were grown in 96-well plates until mid-log phase (21 days) and aliquots from one row of the 96-well plates were pooled into a single well of a secondary pool plate. Aliquots from each well in a column from the secondary PCR pool plate were pooled into a single well of a tertiary PCR pool plate. These pools were frozen at −20° C. and used for genomic DNA isolation for PCR screening. Panel C: We performed PCR screening for specific mutants in the ordered library using a primer hybridizing to the inverted repeats at either ends of the transposon (Himar primer), and gene-specific primers either upstream or downstream of (and occasionally in) the ORF of the target gene. Panel D: The three mannosyltransferases and the lipid phosphatase biochemically characterized in this paper are shown in this panel with their site of action. Question marks indicate that the function of the genes in the indicated biosynthetic steps is either unclear at present (Mb1661c function in adding single α-1,2-mannose residues on the mannan backbone) or has not been confirmed in strains of the *M. tb* complex. Grey-filled circles represent single α-1,2-linked mannose residues.

Figure 2:
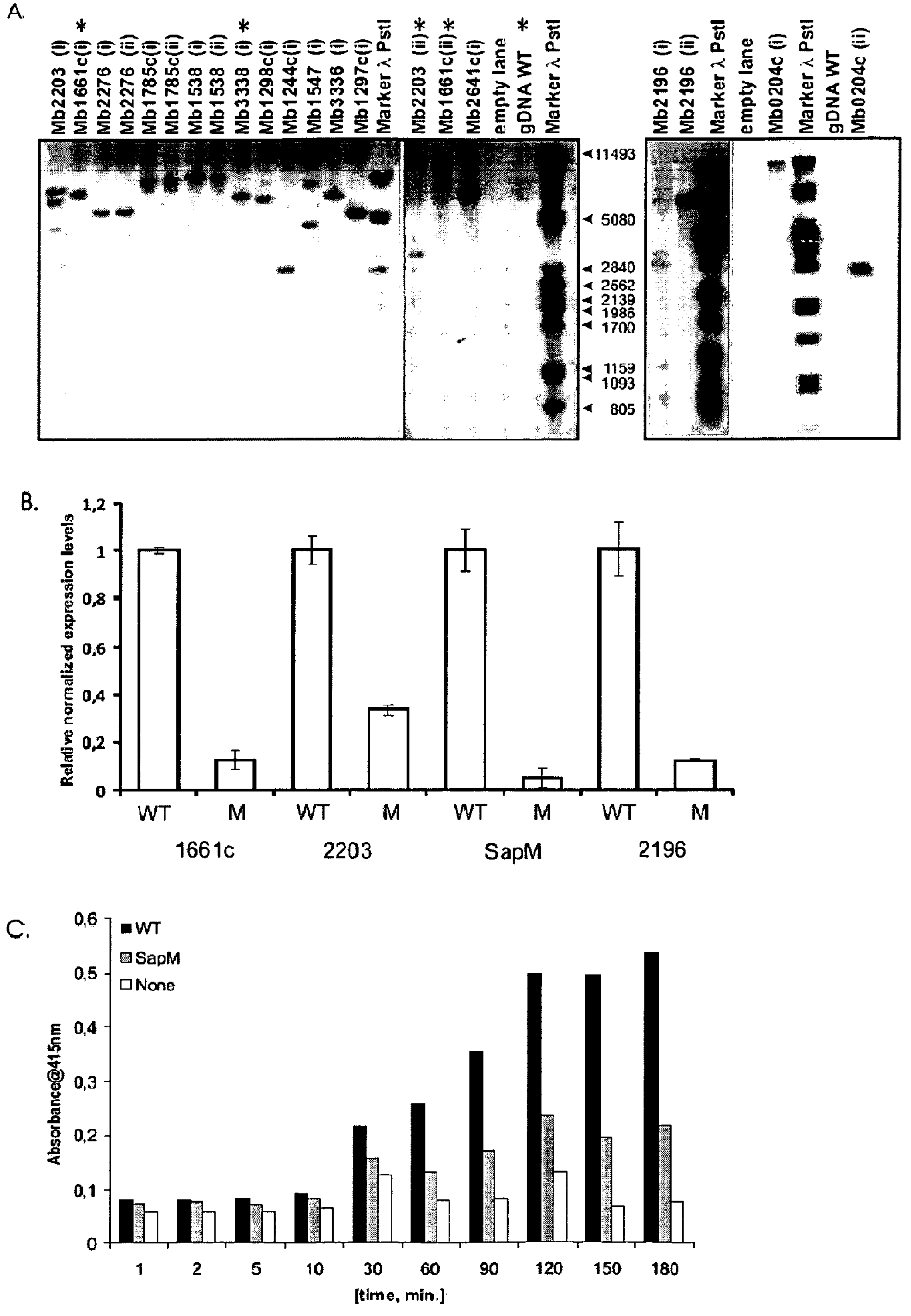

FIG. 2: Southern blot analysis of the mutants, relative expression analysis of disrupted genes by quantitative PCR and phosphatase assay.

Panel A: The genomic DNA of all the mutants was digested with BamHI and PstI (data not shown) and probed with $^{32}P$ dCTP-labeled transposon. The number of bands corresponds to the number of insertions of the transposon in the mutant. Apart from three mutants, i.e., mutants in Mb2203 (i), Mb1547(i), and Mb2196 (i), all other mutants show single integration of the transposon. The markers used were the λPstI marker prepared in-house by digesting 1 μg of lambda DNA with 1 U PstI enzyme (Fermentas, Canada) at 37° C. for two hours. Panel B: Quantification of Mb1661c, Mb2203, SapM (Mb3338) and Mb2196 transcript in wild-type (WT)

and mutants in genes for Mb1661c, Mb2203, SapM, Mb2196 (M). Transcript levels were measured by real-time PCR on cDNA prepared using RNA extracted from log phase cultures of wild-type and mutants. Primer sets are given in the table below. All values were normalized against the expression level of the 16S rRNA-encoding housekeeping gene. The wild-type to mutant transcript ratio was arbitrarily set to 1. Data represent average±SD (n=3). Similar results were obtained in an independent quantitative PCR performed using a second set of primers for each transcript (data not shown). Panel C: Phosphatase activity in the culture supernatant of *M. bovis* BCG wild-type (black bars) versus *M. bovis* BCG SapM mutant (grey bars) were determined by measuring the hydrolysis of pNPP at A415. Culture medium was used as a control (white bars).

| Primer Name | Primer Sequence |
|---|---|
| 1661c FP | 5' GACGTGGGCCGGAATCGAAGCA 3' (SEQ ID NO: 9) |
| 1661c RP | 5' GATCCACCCGACCTGCCAAACCTG 3'(SEQ ID NO: 10) |
| 2203 FP | 5' AACGCTTCGCACTGTGGGTGG 3'(SEQ ID NO: 11) |
| 2203 RP | 5' CGTAGGACATCCCCGCGAGTTGAC3'(SEQ ID NO: 12) |
| SapM FP | 5' ACACACCCGAGCGAACCGAAC 3'(SEQ ID NO: 13) |
| SapM RP | 5' CAAGCGGATGGGTACGAGGTCAGC 3'(SEQ ID NO: 14) |
| 2196 FP | 5' GATGGGCGGGGTGCACAACGAGAT 3'(SEQ ID NO: 15) |
| 2196 RP | 5' CACGCAGATGACGCAGCCAAACC 3'(SEQ ID NO: 16) |
| 16S FP | 5' ATGACGGCCTTCGGGTTGTAA 3'(SEQ ID NO: 17) |
| 16S RP | 5' CGGCTGCTGGCACGTAGTTG 3'(SEQ ID NO: 18) |

Figure 3:
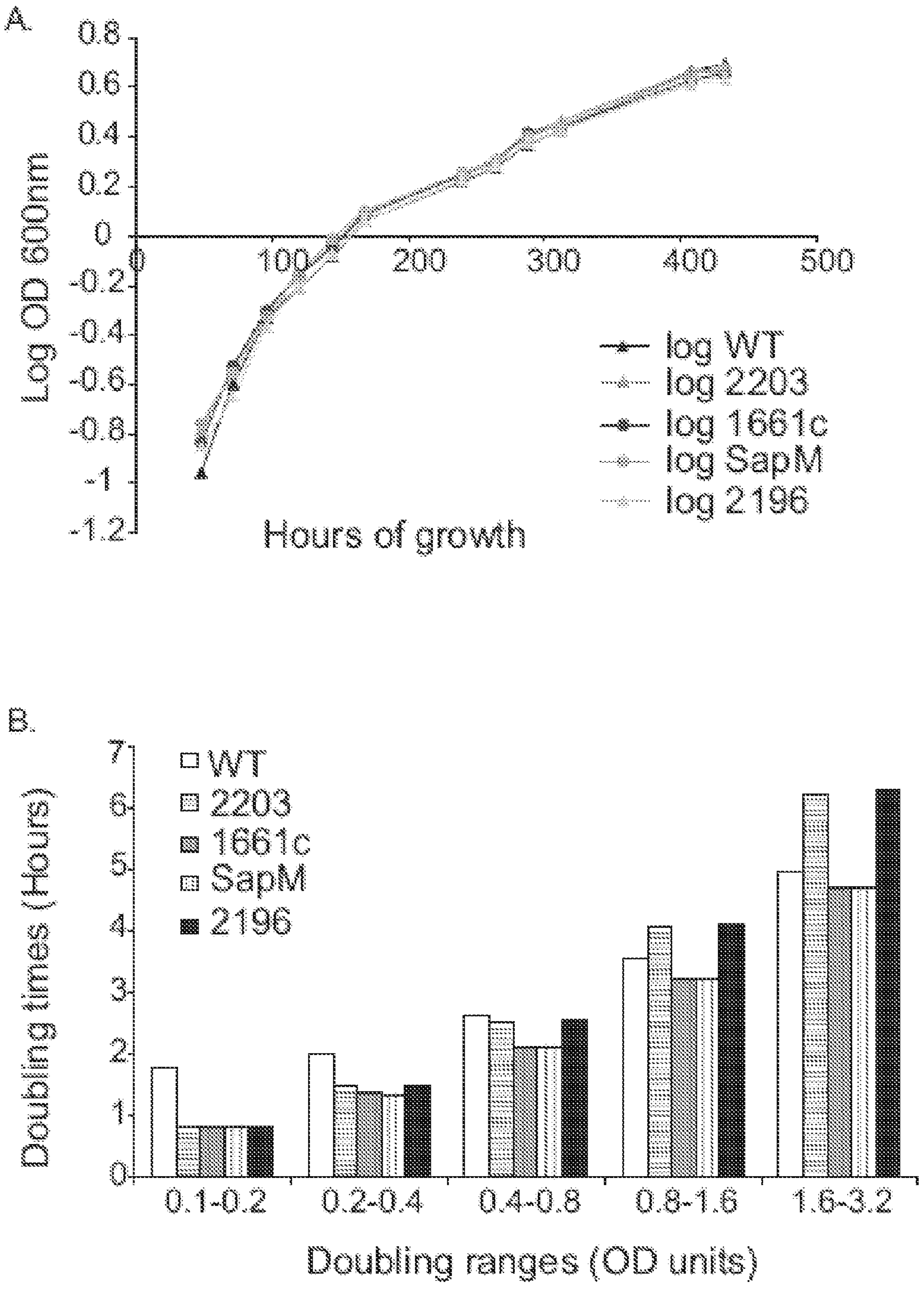

FIG. 3: Growth rate and doubling times.

Panel A: Wild-type and mutants are cultured in Middlebrook 7H9 broth (with glycerol, OADC, 0.05% TWEEN®-80 and antibiotics) for three weeks (504 hours), no stirring, at 37° C. ODs are taken once every 24 hours and doubling times calculated. No significant differences in growth rate are observed. Panel B: Doubling times were calculated from the growth curves and it was observed that as the density of the cultures increases, the doubling time also increases.

Figure 4:
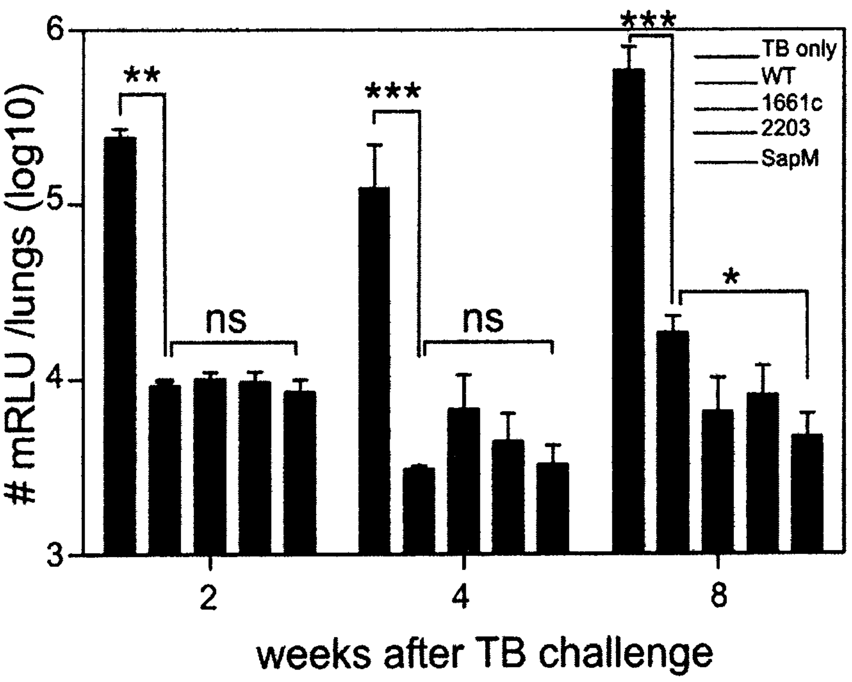
Figure 4:
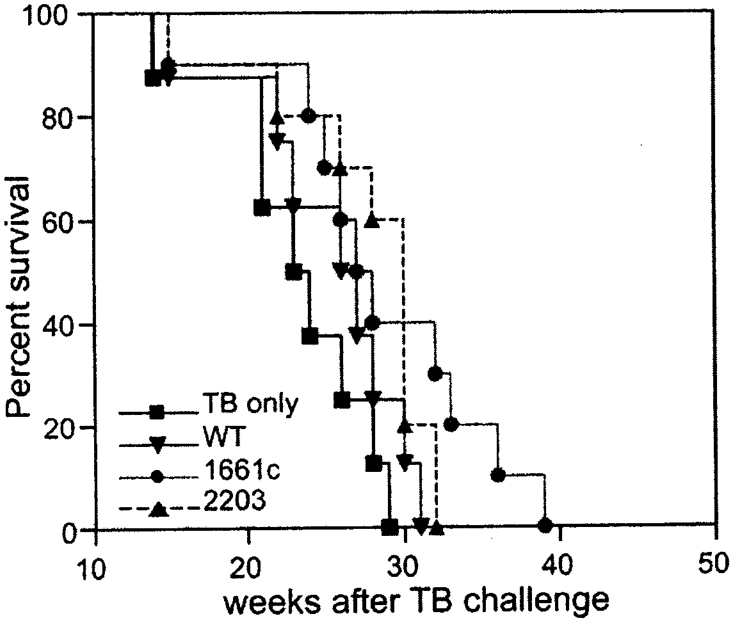
Figure 4:
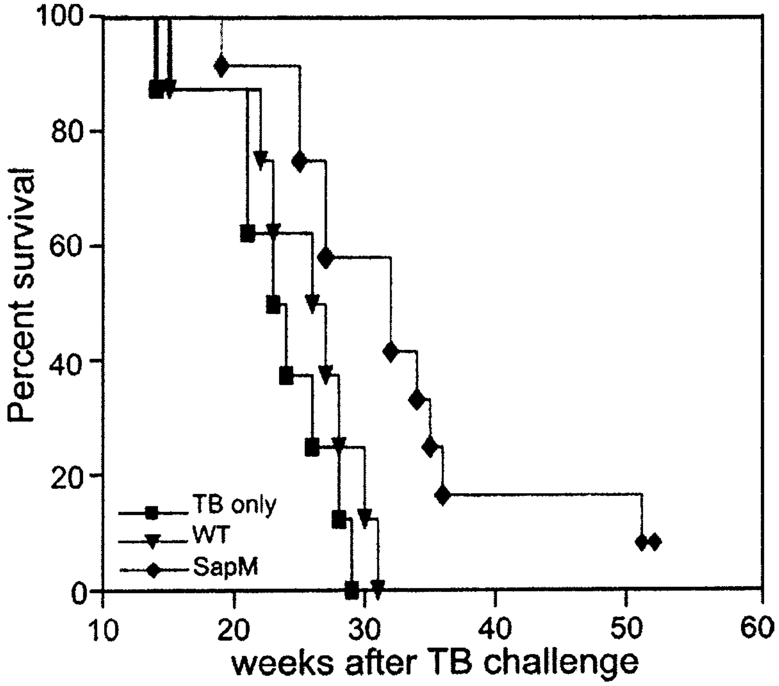
Figure 4:
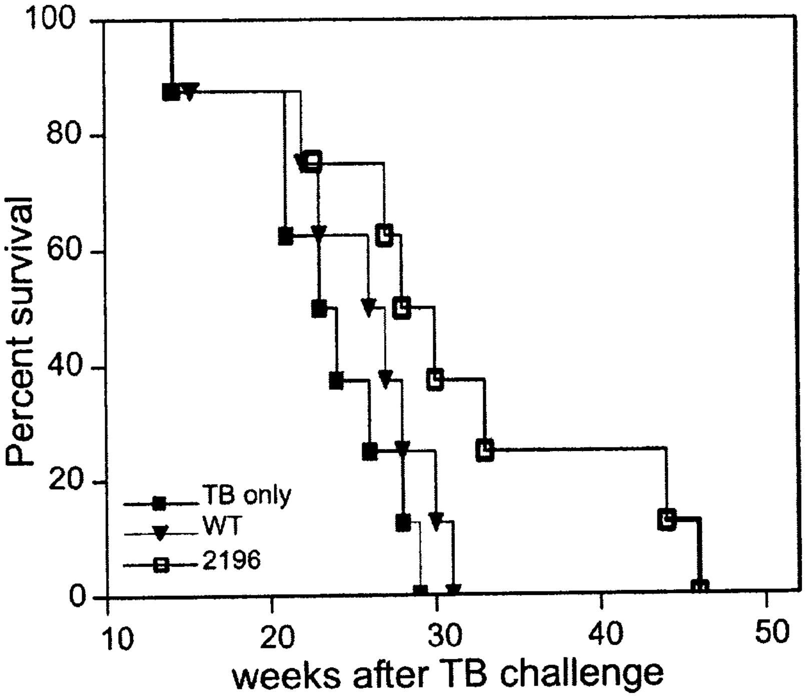
Figure 4:
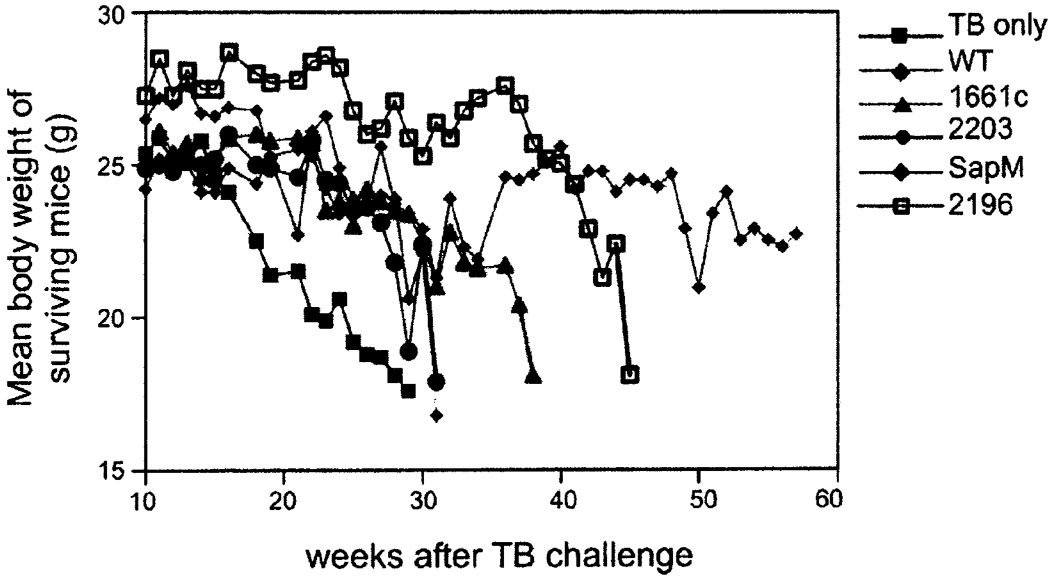
Figure 4:
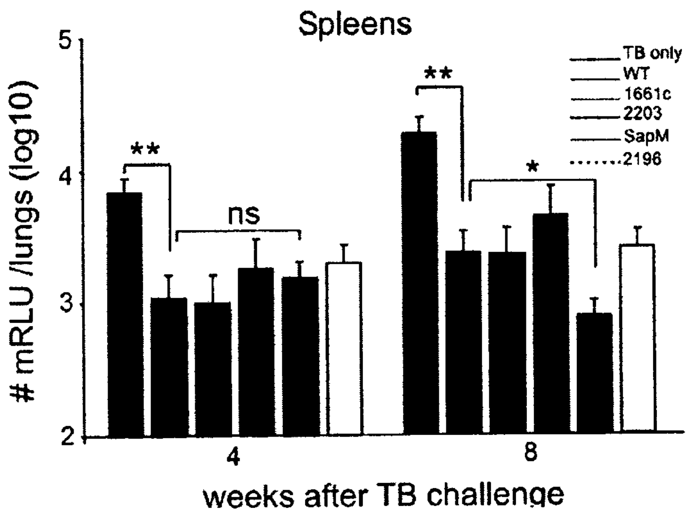
Figure 4:
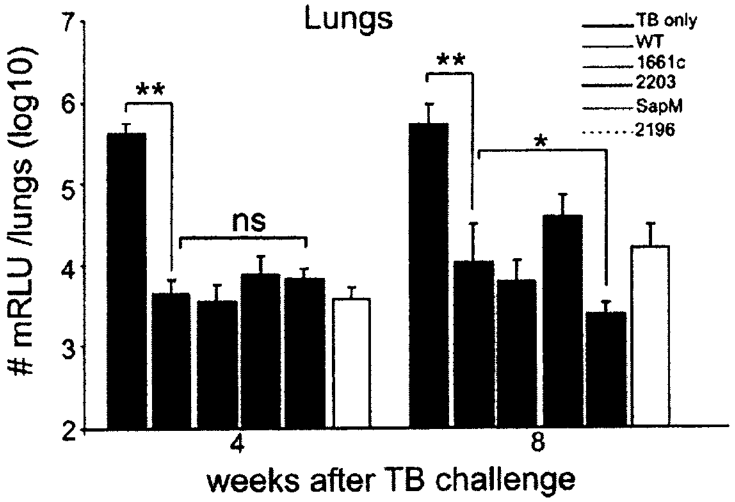

FIG. 4: Protective efficacy of *M. bovis* BCG wild-type versus mutant SapM::T (Mb3338), Mb2203::T, Mb1661c::T and Mb2196::T in Balb/c mice.

Panel A: BALB/c mice were vaccinated subcutaneously with the parental or mutant *M. bovis* BCG strains. Three months post-vaccination, animals were intravenously infected with luminescent *M. tuberculosis* H37Rv. Mice were sacrificed two, four and eight weeks post-infection and the number of bacteria in lungs was determined by luminometry. (One-way ANOVA, Bonferroni's Multiple Comparison Test; *P<0.0001; P<0.0012; *P<0.05; ns, not significant.) Panels B through E: Mice were also followed for eleven months in a long-term survival study and monitored weekly for mortality and weight loss. The percentage of survival is shown in the figure. The median survival time for unvaccinated mice is 23.5 weeks, and for mice vaccinated with BCG wild-type, 1661c::T, 2203::T, 2196::T and SapM::T, respectively, 26.5 weeks, 27.5 weeks, 29 weeks, 30 weeks and 32 weeks (P=0.0145) (Kaplan-Meier, Bonferroni). Panels F and G: BALB/c mice were vaccinated subcutaneously with the parental or mutant *M. bovis* BCG strains. Three months post-vaccination, animals were intratracheally infected with luminescent *M. tuberculosis* H37Rv. Mice were sacrificed four and eight weeks post-infection and the number of bacteria in spleens and lungs was determined by luminometry. (One-way ANOVA, Bonferroni's Multiple Comparison Test; *P<0.0001; P<0.0012; *P<0.05; ns, not significant.)

Figure 5:
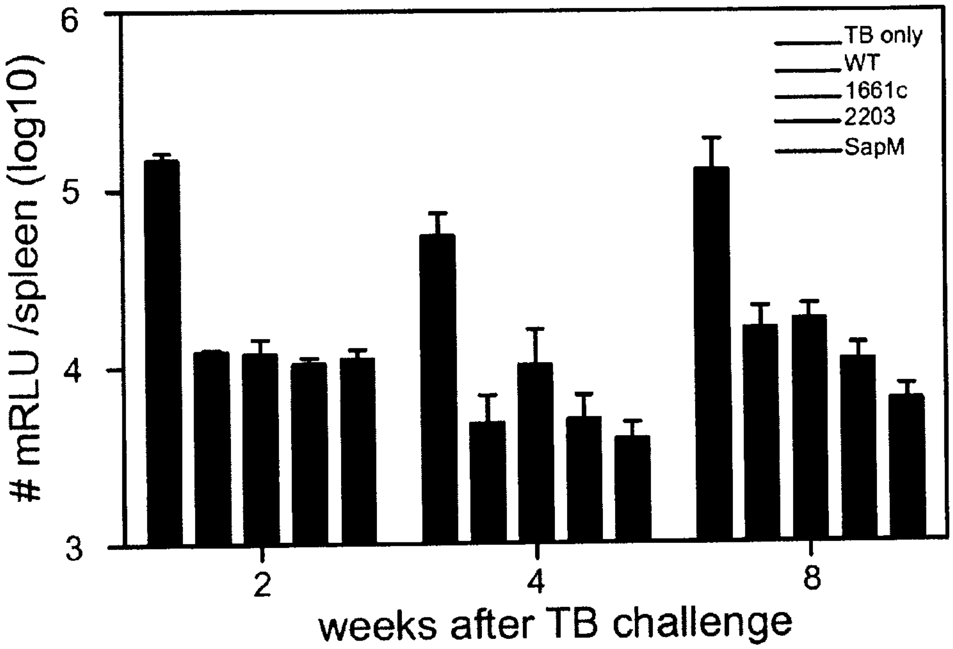

FIG. 5: Protective efficacy of *M. bovis* BCG wild-type versus mutant SapM::T (Mb3338::T), Mb2203::T and Mb1661c::T in Balb/c mice.

BALB/c mice were vaccinated subcutaneously with $10^5$ CFU of the parental or mutant *M. bovis* BCG strains. Three months post-vaccination, animals were intravenously infected with $5\times10^4$ CFU of luminescent *M. tuberculosis* H37Rv. Mice were sacrificed two, four and eight weeks post-infection and the number of bacteria in spleens was determined by luminometry. No significant differences could be detected (One-way ANOVA, Bonferroni's Multiple Comparison Test).

Figure 6:
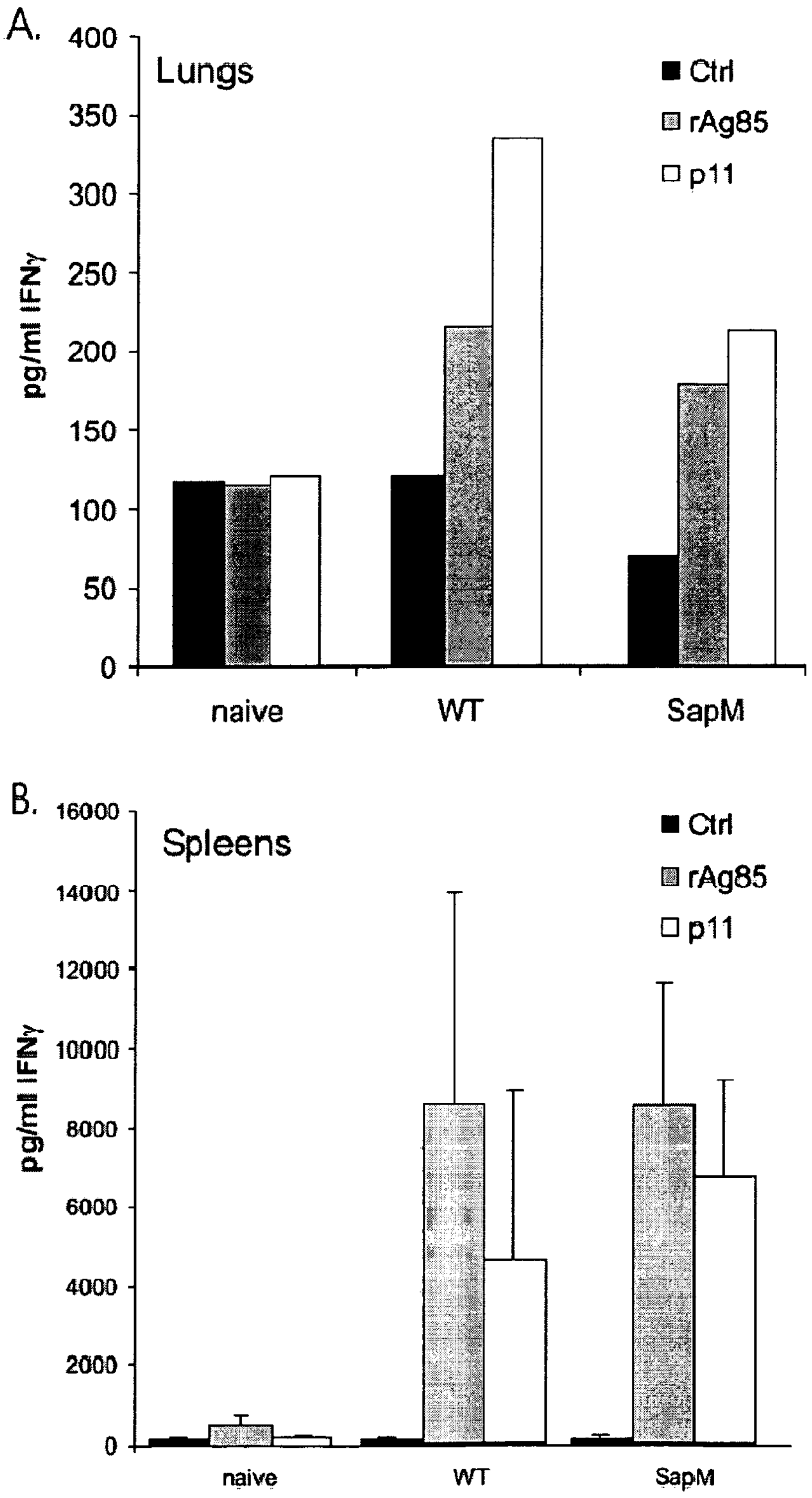

FIG. 6: IFN-γ production following restimulation of spleen and lung cells from vaccinated mice.

BALB/c mice were vaccinated intravenously with the parental *M. bovis* BCG or the SapM locus mutant. Four weeks after infection, mice were killed and lungs and spleens were removed aseptically. IFN-γ production following restimulation of lungs (Panel A) and splenocytes (Panel B) was determined (72 hours post-treatment) in response to recAg85A (Rv3804c) and the synthetic 20-mer peptide p11 (Ag85A99-118aa, dominant CD4 T cell epitope).

Figure 7:
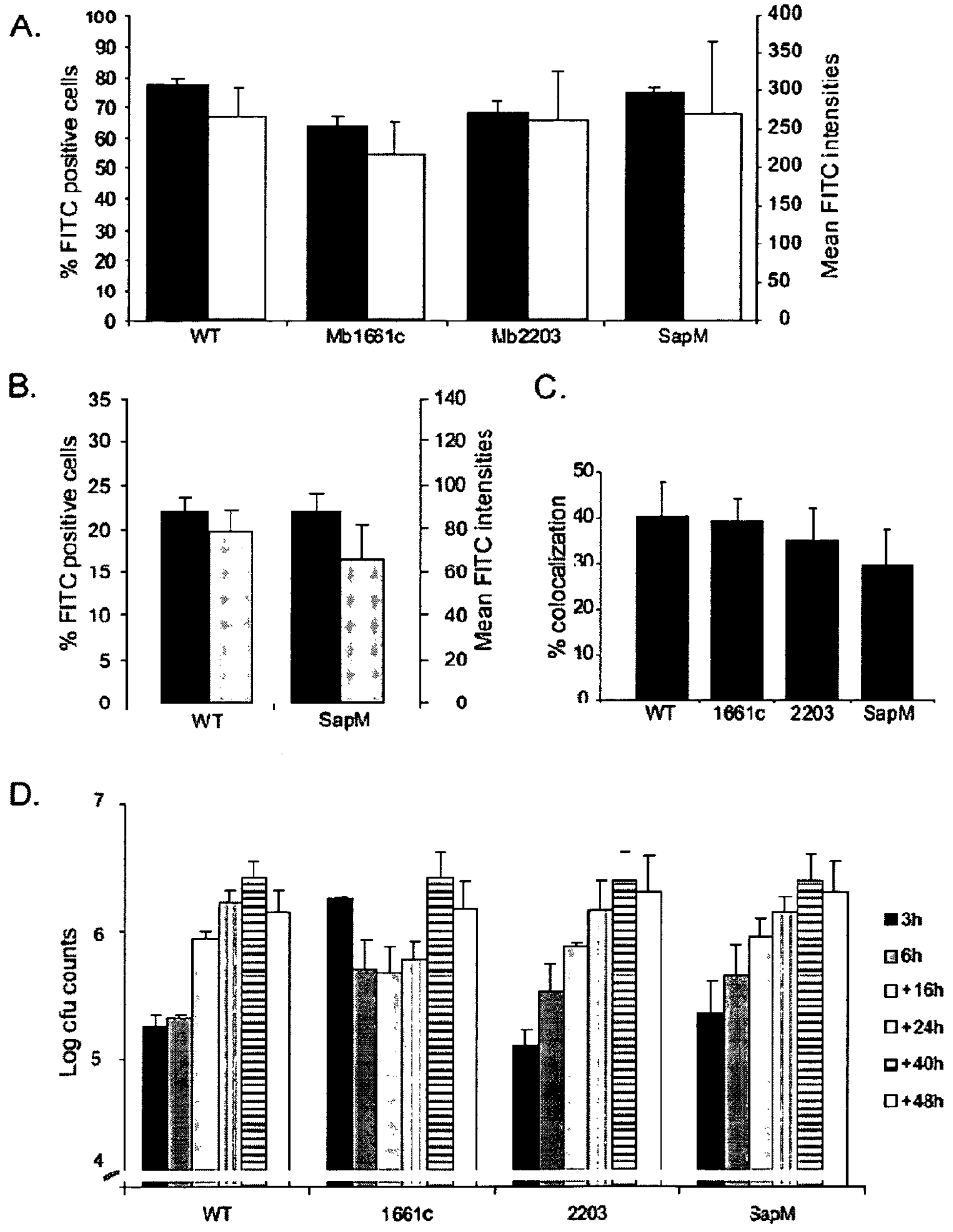

FIG. 7: Binding of *M. bovis* BCG wild-type and mutants to murine macrophages and BM-DCs and clearance following infection of macrophages.

Panel A: Macrophages were infected for six hours with FITC-labeled mycobacteria (*M. bovis* BCG wild-type versus mutants as indicated in the figure) at a MOI of 10. The amount of FITC-positive macrophages and mean FITC intensities are shown as averages of six independent experiments with indicated SEM. Panel B: BM-DCs were infected for 24 hours with FITC-labeled mycobacteria (*M. bovis* BCG wild-type versus SapM::T mutant as indicated in the figure) at a MOI of 2. The amount of FITC-positive DCs and mean FITC intensities are shown as averages of five independent experiments with indicated SEM. Panel C: Colocalization of FITC-labeled bacteria and lysotracker-stained lysosomes in infected murine macrophages three hours post-infection) was determined by confocal microscopy. Shown is an average of three independent experiments, with indicated SEM. Panel D: Mf4/4 cells were infected with *M. bovis* BCG wild-type versus mutants (MOI 10) for the indicated time points. Infected cells were lysed and intracellular mycobacteria counted by plating on 7H10 agar. In a parallel experiment, the cell death of Mf4/4 cells following infection was checked by PI uptake. Macrophages survived at least 48 hours post-infection (data not shown). This experiment is an average of a duplicate experiment (with indicated SEM) and is representative for three other independent experiments. Y-axis is represented in log scale. No statistically significant differences were found in the experiments shown in Panels A, B, C and D between any of the mutants and wild-type BCG ($P>0.1$, Mann-Whitney U-test).

Figure 8:
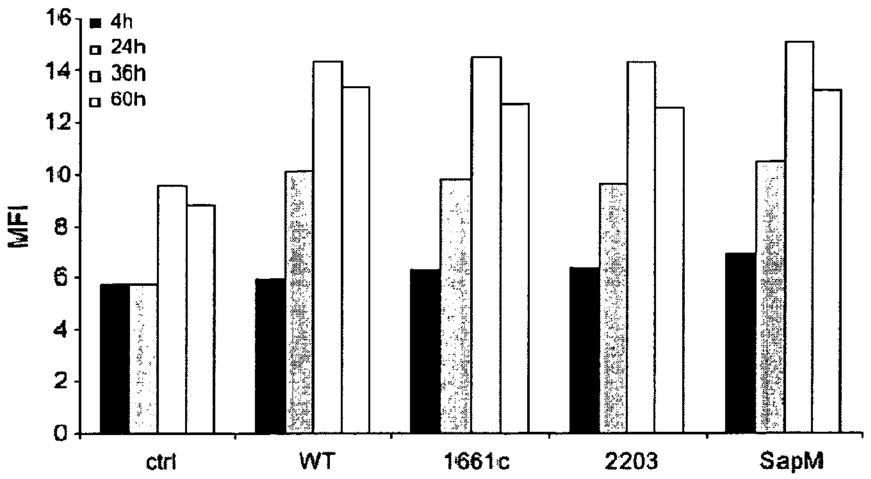

FIG. 8: Intracellular oxidative activity within macrophages and autophagy induction by macrophages and BM-DCs infected with *M. bovis* BCG wild-type versus mutants.

Mf4/4 cells were infected with *M. bovis* BCG wild-type versus mutants at MOI 10 and incubated at 37° C. At the indicated time points post-infection, cells were treated with $CMH_2DCFDA$ washed and analyzed on a FACS Calibur where mean fluorescence intensity (MFI) was determined.

Figure 9:
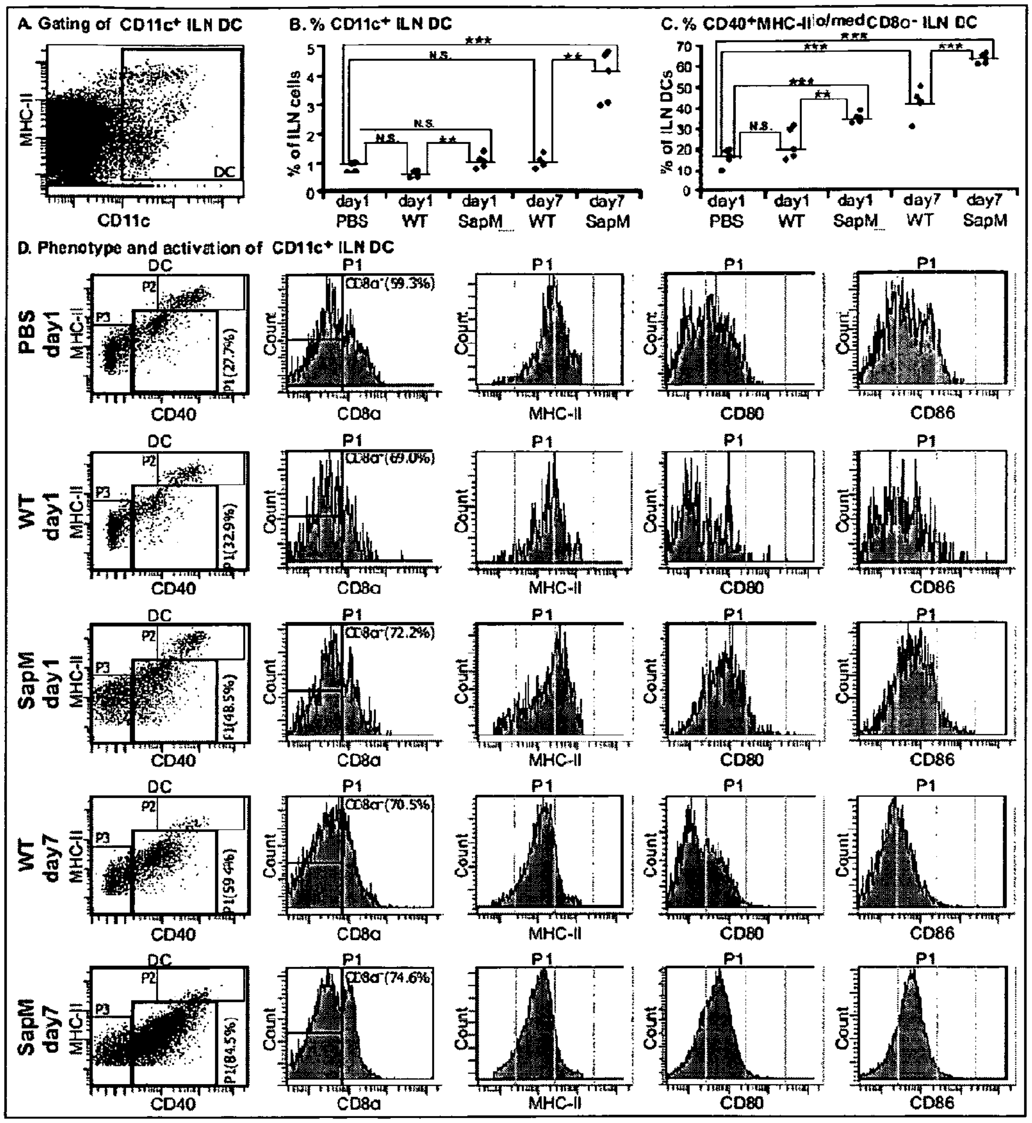

FIG. 9: LN DC trafficking and activation.

Balb/cJ mice were infected subcutaneously with *M. bovis* BCG wild-type and *M. bovis* BCG SapM mutant. At day 1 and day 7 post-infection, five mice per group were sacrificed and inguinal lymph nodes (ILN) were removed. Cells were prepared, labeled with the different antibodies and analyzed by flow cytometry. Panel A: Determination of CD11c+ cells. Panel B: Percentage of CD11c+ cells on the total ILN population. Panel C: Percentage of CD11c+CD40+MHC-IIlo/med CD8α− DCs. Panel D: Representation of MHCIIlo CD40− (P3), MHCIImed CD40+ (P1), MHCIIhi CD40+ (P2) (left column), representation of expression levels of CD8a, MHCII, CD80 and CD86 in on cells in P1. (Kruskal-Wallis, Bonferroni's Multiple Comparison Test; *$P<0.005$; $P<0.01$; *$P<0.05$; ns, not significant.)

Figure 10:
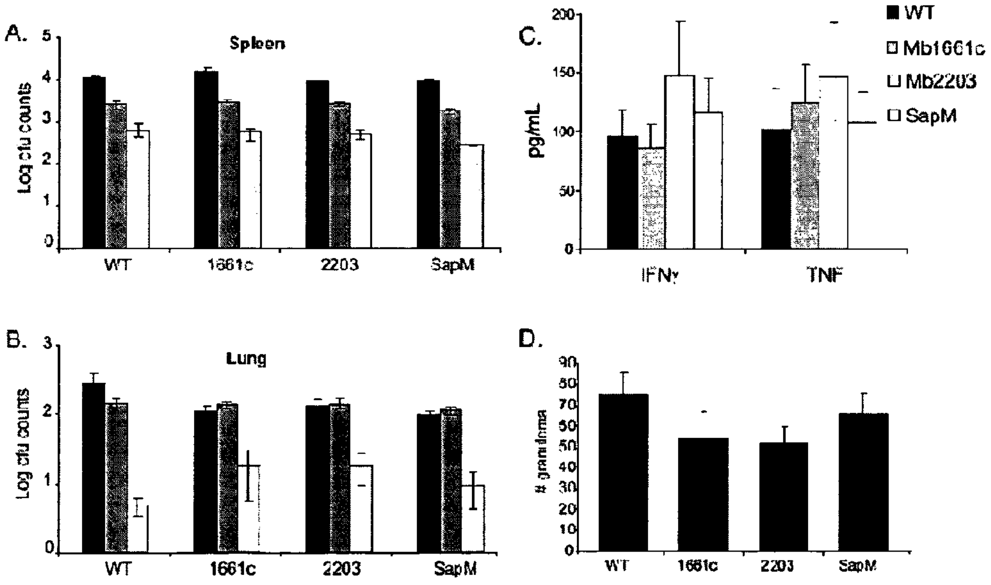

FIG. 10: Bacterial replication of *M. bovis* BCG wild-type versus mutants in spleen and lungs of mice, cytokine production and granuloma formation following infection of mice.

Panels A and B: Balb/c mice were intravenously infected with *M. bovis* BCG wild-type versus mutants and sacrificed two weeks (black bars), four weeks (dark gray bars) and twelve weeks (light gray bars) post-infection (five per group). Lung and spleen homogenates were plated for CFU counting on 7H10 agar in duplicate. The mean and standard errors (SEM) of each group are shown in the figure. No difference was detected between the mutants and wild-type ($P>0.1$, Mann-Whitney U-test). Panel C: C57BL/6 mice were infected intratracheally with *M. bovis* BCG wild-type and mutants. Four weeks post-infection, five mice per group were killed and bronchoalveolar lavage (BAL) was performed. The mean levels of TNF and IFN-γ in the BALF and standard errors (SEM) of each group are shown and representative for two independent experiments. ($P>0.05$, Mann Whitney U test.) Panel D: C57BL/6 mice were infected intravenously with *M. bovis* BCG wild-type and mutants. After three weeks, five mice per group were killed and livers were removed aseptically. Quantitative studies on hematoxylin/eosin (H&E)-stained paraffin sections to identify granuloma were performed by direct microscopic examination (3.5× magnification) and analysis with ImageJ software. The mean and standard errors (SEM) of each group are shown in the figure. Mb1661c::T and Mb2203::T induce less granuloma than *M. bovis* BCG wild-type following infection of mice ($P<0.01$, Mann-Whitney U-test).

Figure 11:
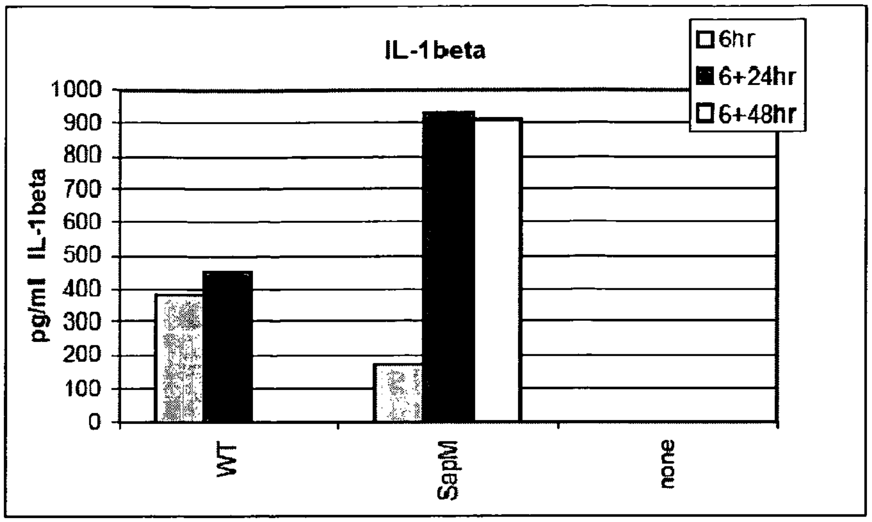
Figure 11:
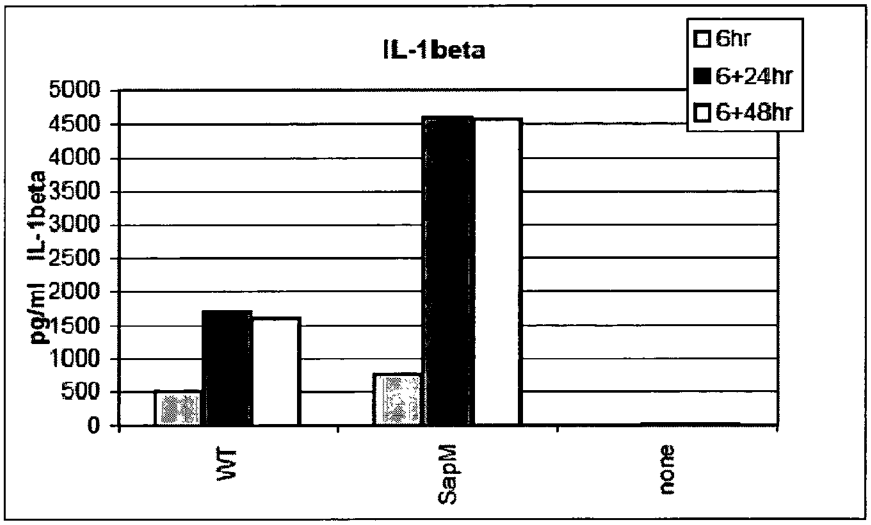
Figure 11:
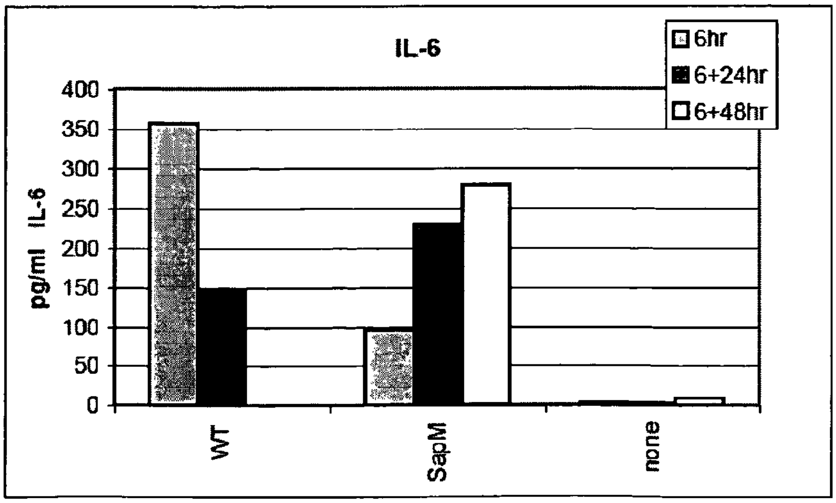
Figure 11:
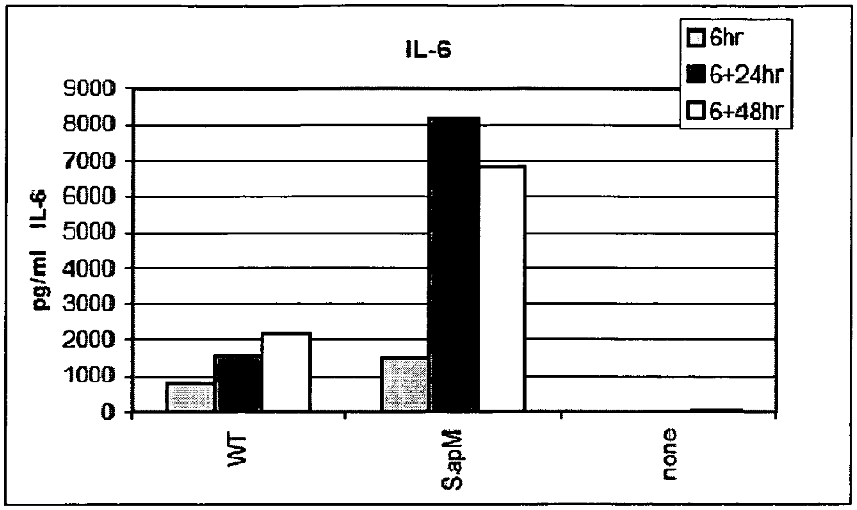
Figure 11:
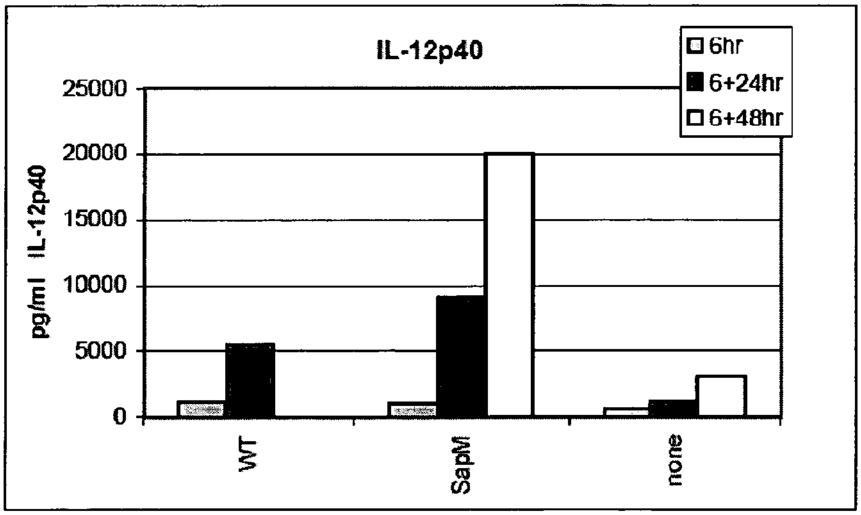
Figure 11:
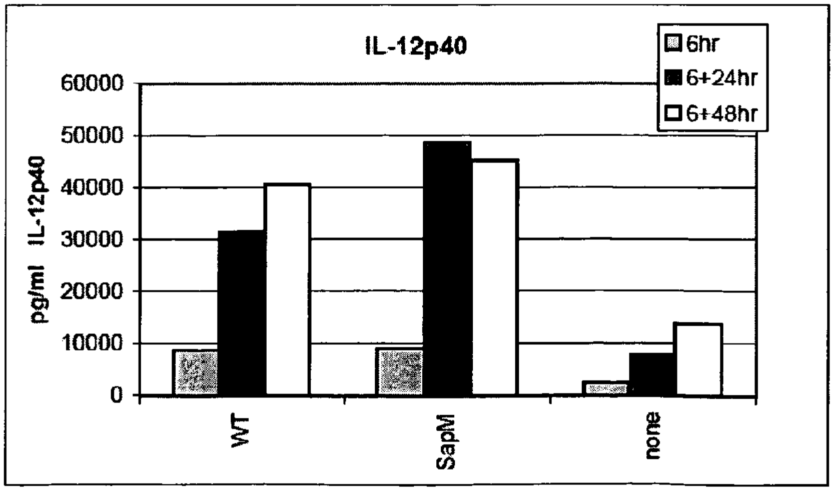
Figure 11:
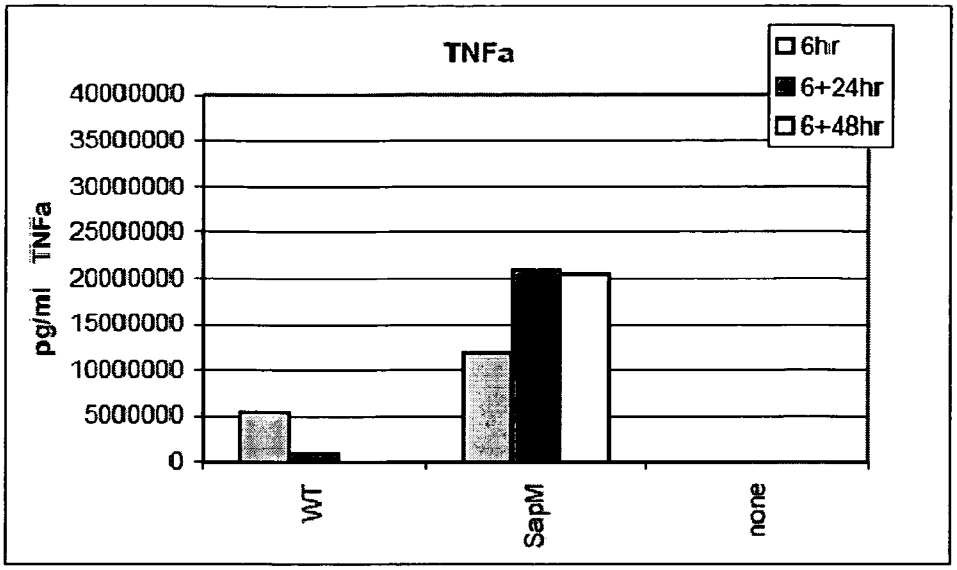
Figure 11:
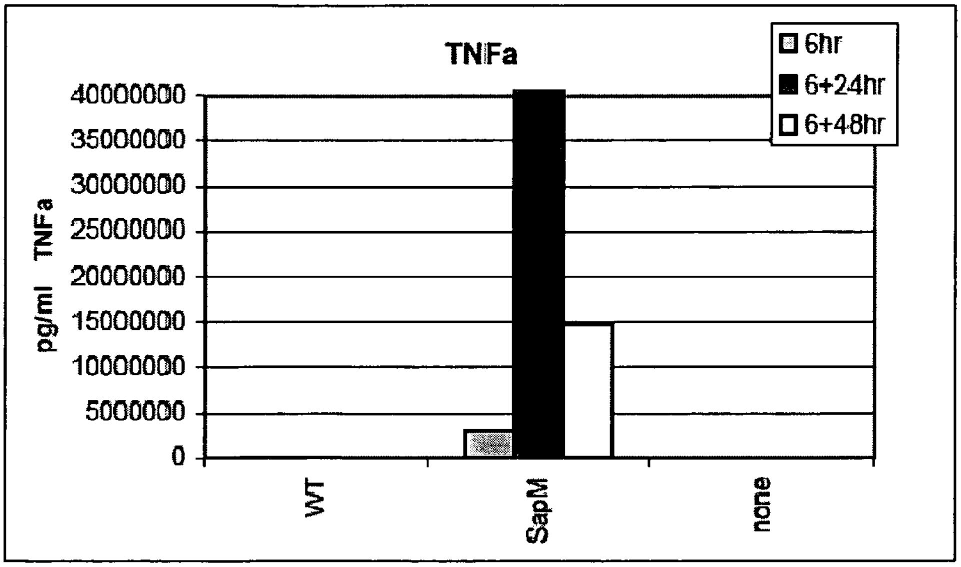

FIG. 11: Cytokine production following infection of BM-DCs with *M. bovis* BCG wild-type versus SapM::T.

BM-DCs were infected for six hours with *M. bovis* BCG wild-type versus mutants (MOI 2). At the indicated time points, supernatant was removed and analyzed for the presence of cytokines by flow cytometry.

DETAILED DESCRIPTION

Definitions

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun, e.g., "a," "an," or "the," this includes a plural of that noun unless something else is specifically stated.

Furthermore, the terms "first," "second," "third," and the like, in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. Unless specifically defined herein, all terms used herein have the same meaning as they would to one skilled in the art of the present invention. Practitioners are particularly directed to Sambrook et al., *Molecular Cloning: A Laboratory Manual,* $2^{nd}$ ed., Cold Spring Harbor Press, Plainsview, N.Y. (1989); and Ausubel et al., *Current Protocols in Molecular Biology* (Supplement 47), John Wiley & Sons, New York (1999), for definitions and terms of the art. The definitions provided herein should not be construed to have a scope less than understood by a person of ordinary skill in the art.

A "*mycobacterium*" as used herein refers to micro-organisms of the genus *Mycobacterium* (sometimes abbreviated as M. herein), from the family of Mycobacteriaceae. Particularly envisaged mycobacteria include members of the *Mycobacterium tuberculosis* complex (Taxon identifier 77643 in the UniProt or NCBI taxonomy database), which includes the species *M. tuberculosis* (the major cause of human *tuberculosis*), *M. bovis, M. bovis* BCG (the strain most often used for vaccination purposes), *M. africanum, M. microti, M. canetti*, and *M. pinnipedii.*

A "genetically engineered mutation" as used throughout the application refers to a mutation in the genetic material (i.e., typically DNA), in particular, a non-naturally occurring mutation, obtained via genetic engineering techniques. Such mutation can be a point mutation, a substitution, a deletion or an insertion. Typically, a genetically engineered mutation as envisaged herein will result in reduced or absent levels of the functional gene product (i.e., a loss-of-function mutation). The mechanism thereof is not vital to the invention, but typically may involve reduction or loss of transcription and/or translation of the affected gene, or only transcription/translation of a dysfunctional gene product. Genetically engineered mutations in a gene need not necessarily be in an exon or open reading frame, they can be in an intron or even be upstream of the start codon, as long as it affects the levels of the functional gene product. This can easily be checked, e.g., by Q-PCR for gene transcription levels. Functionality of a gene product can also be checked, as one of skill in the art will know, e.g., by providing a natural substrate to the affected enzyme.

An "endogenous gene" as used herein is a gene naturally occurring in the organism, in particular, in the species.

The term "SapM," as used herein refers to a gene that encodes a PI3P phosphatase (enzyme class 3.1.3.2), or to the encoded protein product. The gene is also known under other names, e.g., Rv3310 (from the *Mycobacterium tuberculosis* H37Rv strain; GeneID 887988), Mb3338 (from the *Mycobacterium bovis* AF2122/97 strain, GeneID 1093156), SapM putative acid phosphatase or BCG_3375, SapM_1 or JTY_3335, SapM_2 or JTY_3355, SapM_3 or JTY_3375 (respective GeneIDs 4696502 from *Mycobacterium bovis* BCG str. Pasteur 1173P2, 7561659, 7561660, and 7561661 from *Mycobacterium bovis* BCG str. Tokyo 172; the protein product of these differs in one amino acid (A171T) from Rv3310). Other GeneIDs are known as well (typically as hypothetical or provisional protein and not yet validated), but all of these can be mapped to Rv3310 of the H37Rv strain and are thus readily identifiable to the skilled person. Examples include GeneIDs 6698178, 6820173, and 5224028. The Rv3310 and Mb3338 genes and their encoded proteins show 100% sequence identity, the DNA and protein sequence are SEQ ID NOS:1 and 2, respectively. According to particular embodiments, the SapM gene is from a member of the *Mycobacterium tuberculosis* complex (Taxon identifier 77643). According to alternative very particular embodiments, the SapM gene does not encode the hypothetical protein MAP3432 (GeneID 2719192).

As used herein, the "endogenous ManLAM α-1,2-mannosyltransferase corresponding to Mb1661c in *Mycobacterium bovis*" is a gene that corresponds (can be mapped) to Mb1661c (Gene ID 1092601 from the *Mycobacterium bovis* AF2122/97 strain) or Rv1635c (GeneID 885100 from the *Mycobacterium tuberculosis* H37Rv strain), or to the encoded protein product. These two genes are equivalent to each other and show 100% sequence identity in the encoded 556 aa gene product (SEQ ID NO:4), as well as in the primary DNA sequence (SEQ ID NO:3). As with the SapM gene, other GeneIDs are known as well that can easily be (or are already) mapped to the H37RV Rv1635c gene. Examples include GeneIDs 5222331, 6822253 and 6701614.

The term "the endogenous ManLAM α-1,2-mannosyltransferase corresponding to Mb2203 in *Mycobacterium bovis*" as used herein is a gene that corresponds (can be mapped) to Mb2203 (GeneID 1091304 from the *Mycobacterium bovis* AF2122/97 strain) or Rv2181 (GeneID 888269 from the *Mycobacterium tuberculosis* H37Rv strain), or to the encoded protein product. These two genes are equivalent to each other and show 100% sequence identity in the encoded 427 aa gene product (SEQ ID NO:6), as well as in the primary DNA sequence (SEQ ID NO:5). As with the SapM gene or Rv1635c gene, other GeneIDs are known as well that can easily be (or are already) mapped to the H37RV Rv2181 gene. Examples include GeneIDs 6701835, 5222885 and 6822792.

The term "the endogenous LM α-1,6-mannosyltransferase corresponding to Mb2196 in *Mycobacterium bovis*" as used herein is a gene that corresponds (can be mapped) to Mb2196 (GeneID 1091287 from the *Mycobacterium bovis* AF2122/97 strain) or Rv2174 (GeneID 887528 from the *Mycobacterium tuberculosis* H37Rv strain), or to the encoded protein product. These two genes are equivalent to each other and show 99.8% sequence identity in the encoded 516 aa gene product (SEQ ID NO:8)—the only difference being a Ser→Ala substitution at position 451—as well as in the primary DNA sequence (SEQ ID NO:7). As with the SapM gene or Rv1635c gene, other GeneIDs are known as well that can easily be (or are already) mapped to the H37RV Rv2174 gene. Examples include GeneID 909900.

The term "contiguous portions of a sequence" as used herein refers to a non-interrupted sequence of nucleic acids or amino acids also occurring in the same order in the sequence referred to. Particularly envisaged are contiguous portions having a length of at least 25%, 50%, 70%, 75%, 80% or 90% of the length of the reference sequence, and contiguous portions are typically at least 25 nucleic acids or at least eight amino acids.

A "live attenuated vaccine" as used herein is a vaccine containing live or viable micro-organisms with reduced virulence (attenuated); as opposed to an inactivated vaccine.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software Engineering Co., Ltd., South San Francisco, Calif., USA; or accessible via the internet) using standard defaults as used in the reference manual accompanying the software. "Similarity" refers to the percentage number of amino acids that are identical or constitute conservative substitutions (e.g., replacing one hydrophobic amino acid residue with another, or one positively charged amino acid residue with another). Similarity may be determined using sequence comparison programs such as GAP (Deveraux et al. 1984, *Nucleic Acids Research* 12:387-395) or BLAST. In this way, sequences of a similar or substantially different length to those cited herein might be compared by insertion of gaps into the alignment, such gaps being determined, for example, by the comparison algorithm used by GAP.

The present invention relates inter alia to mycobacteria that are mutated in a gene encoding mycobacterial components reportedly involved in phagosome maturation inhibition, and their use in vaccine preparation. Such mutations were found to result in better vaccine antigen processing and presentation. This results in more effective vaccines (offering prolonged survival and/or increased chance of survival in a mouse model of *M. tuberculosis* infection), while maintaining the other properties of the strain used for vaccination (e.g., relating to biosafety measures).

Thus, according to a first aspect, a *mycobacterium* is provided comprising a genetically engineered mutation in at least one endogenous gene selected from SapM, the endogenous ManLAM α-1,2-mannosyltransferase corresponding to Mb1661c in *Mycobacterium bovis*, the endogenous ManLAM α-1,2-mannosyltransferase corresponding to Mb2203 in *Mycobacterium bovis*, and the endogenous LM α-1,6- mannosyltransferase corresponding to Mb2196 in *Mycobacterium bovis*. The nomenclature of genes across different species of mycobacteria is incomplete, and not all genes in each species have been attributed a function yet. In order to avoid confusion, it was chosen to indicate the genes in this way. Based on sequence homology, the skilled person will be able to readily identify the corresponding (or equivalent) gene in other species. For instance, in the *Mycobacterium tuberculosis* H37Rv reference strain, the gene corresponding to Mb1661c is Rv1635c, both having the same sequence (SEQ ID NO:3), and the gene corresponding to Mb2203 is indicated as Rv2181, also having an identical sequence (SEQ ID NO:5) (see Table 1). Note that this also applies to the PI3P phosphatase SapM: indicated as Mb3338 and Rv3310 in *Mycobacterium bovis* and *Mycobacterium tuberculosis*, respectively, but having an identical sequence, corresponding to SEQ ID NO:1.

Thus, according to particular embodiments, the endogenous SapM gene comprises SEQ ID NO:1, contiguous portions thereof, or sequences at least 90%, at least 95%, at least 98%, or at least 99% identical to SEQ ID NO:1 or the contiguous portions thereof. Similarly, the ManLAM α-1,2-mannosyltransferase equivalent to the Mb1661c gene may comprise SEQ ID NO:3, contiguous portions of this sequence, or sequences at least 90%, at least 95%, at least 98%, or at least 99% identical to SEQ ID NO:3 or the contiguous portions thereof. Likewise, the ManLAM α-1,2-mannosyltransferase corresponding to Mb2203 comprises in particular embodiments SEQ ID NO:5, contiguous portions thereof, or sequences at least 90%, at least 95%, at least 98%, or at least 99% identical thereto. Or the LM α-1,6-mannosyltransferase corresponding to Mb2196 comprises in particular embodiments SEQ ID NO:7, contiguous portions thereof, or sequences at least 90%, at least 95%, at least 98%, or at least 99% identical thereto.

Alternatively, the percentage sequence identity or similarity may be defined at the protein (amino acid) level. Thus, the endogenous SapM gene may be defined as a gene encoding a sequence comprising SEQ ID NO:2, contiguous portions of this sequence, or encoding sequences at least 90%, at least 95%, at least 98%, or at least 99% identical to SEQ ID NO:2, or a contiguous portion thereof. Similarly, the ManLAM α-1,2-mannosyltransferase equivalent to the Mb1661c gene may encode sequences comprising SEQ ID NO:4, contiguous portions thereof, or sequences at least 90%, at least 95%, at least 98%, or at least 99% identical to SEQ ID NO:4, or the contiguous portions thereof. Likewise, the ManLAM α-1,2-mannosyltransferase corresponding to Mb2203 encodes in particular embodiments sequences comprising SEQ ID NO:6, contiguous portions thereof, or sequences at least 90%, at least 95%, at least 98%, or at least 99% identical thereto. Or the LM α-1,6-mannosyltransferase corresponding to Mb2196 encodes in particular embodiments sequences comprising SEQ ID NO:8, contiguous portions thereof, or sequences at least 90%, at least 95%, at least 98%, or at least 99% identical thereto.

According to particular embodiments, combinations of these genes are mutated, for instance, both ManLAM α-1,2-mannosyltransferase genes are mutated, or the endogenous SapM gene and one or two of the ManLAM α-1,2-mannosyltransferase genes or the LM α-1,6-mannosyltransferase gene. Additionally and/or alternatively, one or more of these endogenous genes may contain more than one mutation.

According to specific embodiments, the gene with the genetically engineered mutation encodes a gene product that has a reduced (knock-down) or absent (knock-out) functionality. This may be either because there is none or less of the gene product present than in the corresponding wild-type strain, and/or because the gene product is not or only partially functional. Thus, the genetically engineered mutations may influence expression levels of the gene product, stability of the gene product, encode defunct or nonsense gene products (e.g., by insertion of a stop codon), encode a different gene product, or any combination of these. According to specific embodiments, the expression levels of the gene product are reduced by 25%, 50%, 75% or more. Expression of the gene product can, e.g., be evaluated by QPCR. Mutations may be insertions, substitutions or deletions, and may vary in size from one base pair (or one amino acid) to the whole gene (e.g., complete gene deletion or substitution). Of note, mutations also include mutations upstream of the start codon, such as in the promoter region, particularly mutations within 30 nucleotides upstream of the start codon, as long as these mutations affect the levels and/or function of the gene product. According to particular embodiments, the genetically engineered mutation is created by insertion mutagenesis. According to specific embodiments, the mutation is not generated using an allelic exchange mutagenesis method.

According to specific embodiments, the *mycobacterium* may have further mutations as well. According to even more specific embodiments, the *mycobacterium* also comprises at least one mutation that decreases virulence (note that this is, for instance, the case in the *Mycobacterium bovis* BCG strain). Another example of these further mutations, are mutations in antioxidant genes. Indeed, Sadagopal et al. have shown that reducing the activity and secretion of microbial antioxidants enhances the immunogenicity of BCG (Sadagopal et al., 2009). This may be of particular interest for pulmonary TB, as the traditional BCG strains are less reliable in protecting against this form of TB. As these antioxidants function independently from phagosome maturation, it can be expected that a *mycobacterium* with at least one mutation in a phagosome maturation gene (such as in SapM, Mb1661c, Mb2203 or Mb2196) and at least one mutation in an antioxidant gene will be even more suitable as basis for an improved vaccine composition. Particularly envisaged as antioxidant genes to be down-regulated or knocked out are one or more (or all) of the group selected from secA2, sigH and SodA. How mutants in these antioxidant genes can be generated is described in Sadagopal et al. (2009).

According to specific embodiments, the mycobacteria described herein are selected from *Mycobacterium tuberculosis, Mycobacterium bovis* or *Mycobacterium bovis* Bacille Calmette-Guérin (BCG). Note that many strains for BCG are known (including, but not limited to, BCG-Russia, -Japan, -Moreau, -Sweden, -Birkhaug, -China, -Prague, -Glaxo, -Danish, -Merieux, -Tice, -Phipps, -Frappier, -Connaught and -Pasteur), and all of them are envisaged for the applications described herein.

Brosch et al. (2007) have demonstrated that the different BCG strains harbor different duplicated regions. This is of interest, as some BCG strains (e.g., BCG-Pasteur) do not have a duplication of regions harboring the phagosome maturation genes and antioxidant genes discussed herein, whereas others (e.g., BCG-Danish) do. As it is easier to ensure non-functional genes when they are not duplicated, it is envisaged in particular embodiments to use strains not harboring a duplication of regions harboring a phagosome maturation gene (such as, e.g., SapM). Alternatively or additionally, it is envisaged that the strain does not have a duplication of an antioxidant gene.

According to very specific embodiments, the *mycobacterium* is selected from the deposited strains LMG P-25310 (*Mycobacterium bovis* BCG carrying a mutation in the SapM gene—Mb 3338), LMG P-25309 (*M. bovis* BCG carrying a mutation in the Mb1661c gene), LMG P-25308 (*M. bovis* BCG carrying a mutation in the Mb2203 gene) and LMG P-25441 (*M. bovis* BCG carrying a mutation in the Mb2196 gene). Deposits have been made at the BCCM/LMG Bacteria Collection, University of Gent, Belgium. Also deposited was the wild-type *M. bovis* BCG strain used for generation of the mutants, such as LMG P-25307.

In a further aspect, uses of a *mycobacterium* as described herein, or of a portion thereof, are provided for the preparation of a recombinant vaccine, particularly a vaccine against *tuberculosis*. Whereas typically, a whole (attenuated) *mycobacterium* will be used in a vaccine, it is envisaged that portions thereof may be used (a so-called—"sub-unit vaccine"), e.g., containing specific proteins from the *Mycobacterium*. Very particular subsets of sub-unit vaccines are recombinant vaccines, in which at least one protein from a *mycobacterium* is non-endogenously present in micro-organisms used for vaccination (e.g., through recombinant overexpression). A recombinant vaccine can also be used as a vaccine against diseases other than *tuberculosis*, when other non-endogenous proteins are expressed as antigens in the *mycobacterium*.

The development of mycobacterial genetic systems to express foreign antigens and the adjuvanticity of BCG are the basis of the potential use of this attenuated *mycobacterium* as a recombinant vaccine (Stover et al., 1991). Over the years, a range of strategies has been developed to allow controlled and stable expression of viral, bacterial and parasite antigens in BCG, resulting in both cellular and humoral immune responses against these heterologous antigens (Dennehy et al., 2005). Moreover, it has been demonstrated that recombinant BCG overexpressing antigens of *M. tuberculosis* is more efficient in conferring protection against *tuberculosis* than the wild-type BCG strain (Castanon-Arreola et al., 2005; Horwitz, 2005).

A good overview of heterologous bacterial, parasite and viral antigens that may be successfully used in recombinant BCG as a vaccine vector is given in Bastos et al. (2009), particularly in tables 1-3. Examples include, but are not limited to, bacterial antigens to provide a vaccine against bacterial infection (e.g., of *Escherichia coli, Borrelia burgdorferi, Streptococcus pneumonia, Listeria monocytogenes, Bordetella pertussis, Mycobacterium tuberculosis, Mycobacterium leprae, Anaplasma marginale, Leptospira interrogans, Mycoplasma hyopneumoniae, Clostridium perfringens*), bacterial toxins (e.g., Pertusis toxin, tetanus toxin, cholera toxin), parasitic antigens to provide protection against parasitic disease (e.g., of *Leishmania* species, *Schistosoma mansoni, Schistosoma haematobium, Schistosoma japonicum, Plasmodium yoelii, Plasmodium falciparum, Toxoplasma gondii, Leishmania chagasi, Echinococus multilocularis, Eimeria tenella*), and viral antigens to protect against viral disease (e.g., of HIV-1, FMDV (foot-and-mouth disease virus), SIV, measles virus, papillomavirus, rabies virus, PRRSV (Porcine reproductive and respiratory syndrome virus), HCV (Hepatitis C virus), HBV (Hepatitis B virus), CRPV (cottontail rabbit papillomavirus), rotavirus, infectious bronchitis virus, and RSV (respiratory syncytial virus)).

The skilled person will readily appreciate the potential of recombinant BCG and realize that this list is non-exhaustive and that other antigens can be readily tested to provide a vaccine for other (or even the same) diseases (for instance, a BCG equipped with the membrane-perforating listeriolysin (Hly) of *Listeria monocytogenes* showed a significantly improved protection in mouse model when compared to the parental BCG strain following aerosol challenge with *M. tuberculosis* (Grode et al., 2005)).

Moreover, recombinant BCG may also be used as an immunomodulator. Immunomodulators are substances or live organisms that accelerate, prolong, or enhance the quality of a specific immune response to antigens. Live, attenuated, recombinant bacterial vaccines have been largely used to modulate the immune system to respond in a specific profile to a specific antigen. The immunomodulator effect of wild-type BCG has been well described, and recently the expression of cytokines has even improved this effect. This approach has allowed modulation of the immune system to respond with a specific and desired pattern of cytokines. Examples of cytokines that can be expressed in recombinant BCG include, but are not limited to, IFN-γ, IL-2, IL-18, IFN-α-2b (see table 4 of Bastos et al., 2009).

Through immunomodulation, BCG may also be a useful therapy in the treatment of cancer, e.g., by strengthening particular immune responses. Even non-recombinant BCG can be used in the treatment of cancer, as promising results have been shown in, e.g., leukemia, melanoma, colon cancer, lung cancer, skin cancer and bladder cancer. It is envisaged that the mycobacteria described herein can be used to develop vaccines (either recombinant or non-recombinant) against these diseases. Most particularly, it is envisaged that the mycobacteria provided herein can be used for a vaccine against bladder cancer. Indeed, BCG has been FDA-approved for treatment of bladder cancer since 1990. Most particularly, it is envisaged to treat superficial bladder cancer (i.e., bladder cancer not invading the muscular wall of the bladder), as BCG is recognized as the most effective treatment for this disease. This could even further be increased by providing BCG that recombinantly express IL-18 (Luo et al., 2004).

According to particular embodiments, the vaccine is a *M. bovis, M. bovis* Bacille Calmette-Guérin (BCG), or *M. tuberculosis*-based vaccine. According to alternative (but not exclusive) particular embodiments, the vaccine comprises a live attenuated vaccine.

Thus, methods are also provided for preparing a vaccine (or vaccine composition), comprising the step of generating a vaccine, e.g., by providing a live attenuated *mycobacterium* strain in a pharmaceutically acceptable carrier.

According to yet a further aspect, vaccines are provided comprising a *mycobacterium* as described herein, thus with a non-naturally occurring mutation in at least one endogenous gene selected from SapM, the endogenous ManLAM α-1,2-mannosyltransferase corresponding to Mb1661c in *Mycobacterium bovis*, the endogenous ManLAM α-1,2-mannosyltransferase corresponding to Mb2203 in *Mycobacterium bovis*, and the endogenous LM α-1,6-mannosyltransferase corresponding to Mb2196 in *Mycobacterium bovis*, in a pharmaceutically acceptable carrier or excipient. According to an alternative embodiment, the vaccines comprise a portion of the *mycobacterium*.

According to most specific embodiments, the vaccine is a vaccine against *tuberculosis*. In other words, the vaccine is suitable to protect an animal, in particular a mammal, from challenge by a virulent *mycobacterium* selected from *M. bovis* or *M. tuberculosis*. Many mammals are known to suffer from *tuberculosis*, in particular, from *M. tuberculosis* or *M. bovis* infection, and these animals may benefit from the vaccine. Such mammals include pets (such as, but not limited to, cats, dogs, rabbits, hamsters, guinea pigs and the like), livestock (such as, but not limited to, horses, donkeys, mules, bovines, cows or other cattle, llamas, camels or other camelids, pigs, sheep, goats, deer, elk, reindeer), non-domestic or zoo animals (such as, but not limited to, elephants, nonhuman primates (e.g., mandrills, baboons, macaques, etc.), wild felines (tigers, lions, etc.), bears, antelopes, sea lions, badgers, possums, and the like) and humans. *Tuberculosis* may behave as a zoonotic disease. Mammals that are particularly envisaged for the vaccines described herein are bovines, most particularly cows. Also particularly envisaged are humans, in particular, children. Generally, young animals are particularly envisaged for the vaccines described herein. With young animals, it is typically meant that they are not yet of reproductive age.

According to particular embodiments, the vaccine is a live attenuated vaccine.

Thus, the *mycobacterium* as described herein is provided for use in treatment of *tuberculosis*. According to further embodiments, the vaccine as described herein is provided for use in treatment of *tuberculosis*. Thus, methods are provided of protecting an animal, in particular a mammal, in particular an animal in need thereof, from a virulent *Mycobacterium tuberculosis* or *M. bovis*, comprising treating the mammal with a vaccine as described herein (or possibly with a live attenuated *mycobacterium* as described herein). Alternatively, methods are provided of inducing an immune response in a mammal, the method comprising inoculating the mammal with the *mycobacterium* as described herein or the vaccine as described herein.

The way of administration of the vaccine can be determined by the skilled person, in accordance with the administration routes known in the art. These include, but are not limited to, subcutaneous administration, intradermal administration, intranasal administration, oral administration, parenteral administration, intramuscular administration, injection, or the like.

The dosage regimen may also be determined by the skilled person using his expertise (e.g., single administration, repeated administration (twice or more at regular or irregular intervals), etc. This will typically also depend on the disease to be treated and the individual receiving the treatment (in bladder cancer in humans, for instance, a low-dose BCG regimen has been described as 75 mg, while a standard dose is 150 mg). Doses of BCG as low as 1 mg have been documented to effectively support an immune response for a long period of time (5 years). In *tuberculosis*, an example of a typical dose is much lower: 0.075 mg, corresponding to 0.3 to 1.2 million living mycobacteria. Roughly speaking, a typical dose may fall between 0.01 μg/kg body weight and 10 mg/kg body weight. In treatment of *tuberculosis*, one treatment typically protects for a number of years. However, it is also envisaged that repeat doses are given (as is, e.g., typically the case in treatment of bladder cancer).

As the vaccines described herein are more effective than standard vaccines, it is also envisaged that the treatment regimen may be shorter than for a treatment regimen with the equivalent WT *mycobacterium* strain; or that a suboptimal dose can be used (i.e., a dose that is lower than that typically used with the equivalent WT *mycobacterium* or WT *mycobacterium*-based vaccine).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, useful methods and materials are described below. The materials, methods, and examples are illustrative only and not intended to be limiting. Other features and advantages of the invention will be apparent from the detailed description and from the claims.

EXAMPLES

Materials and Methods

Mycobacterial Strains and Media

The streptomycin resistant *M. bovis* BCG strain 1721 (RpsL, 42 Lys→Arg; a gift of Prof. P. Sander, Institute for Medical Microbiology, Zurich) and its mutants were grown in Middlebrook 7H9 broth (Difco) supplemented with 0.05% TWEEN® 80, Middlebrook OADC (Becton Dickinson) and appropriate antibiotic selection (100 μg/ml streptomycin for wild-type and additionally 50 μg/ml kanamycin for the mutants) when grown in liquid culture. Difco Middlebrook 7H10 agar (similarly supplemented) was used for growth on solid culture. We selected the mutants on 7H10 plates supplemented with 20 μg/ml kanamycin. For the propagation of the phage, a streptomycin-resistant *M. smegmatis* strain (also obtained from Prof. P. Sander) was used and grown in the Middlebrook 7H9 broth (Difco) supplemented with Middlebrook ADC (Becton Dickinson) without TWEEN® 80 or antibiotics. Throughout this study, *M. bovis* BCG was cultivated in static culture (i.e., without shaking) in tissue culture flasks equipped with a gas-permeable filter cap. The flasks were incubated upright with 10 mL culture in a T25 flask (Falcon).

Construction of an Ordered Transposon Mutant Library and Generation of the Mutants The transposon donor phagemid, ΦmycomarT7 (received as a gift from Prof. Dr. Eric Rubin, Harvard School of Public Health, Boston), was propagated in *M. smegmatis* to generate phage stocks as described.[43] Transduction was performed in *M. bovis* BCG, grown to OD600 1.0 as previously described.[54] The library was plated on 7H10 agar plates containing 20 μg/ml kanamycin, as the transposon contains the kanamycin resistance gene. The plating was performed at the appropriate dilution to obtain well-separated single colonies. Once the colonies were well grown on the 7H10 agar plates, they were manually picked using sterile toothpicks into deep 96-well plates, each plate containing 96 individual mutants. Great care was taken to only pick those colonies that were clearly clonal to avoid contamination in the subsequent ordering of the mutants.

Ordering of the Library into Pools

Individual mutants were grown in 96-well plates in 200 μl of Middlebrook 7H9 broth supplemented with 10% OADC and 50 μg/ml kanamycin and 100 μg/ml streptomycin until mid-log phase (21 days) and aliquots frozen in 50% glycerol at −80° C. The remaining cultures were duplicated and grown for three more weeks. Ten μl culture aliquots from each row of a deep 96-well plate (12 individual mutants from the primary plate) were pooled into a single well to form a "secondary pool" (FIG. 1, Panel B) and 10 μl culture aliquots from each column of a secondary pool plate were pooled into a single well to form a "tertiary pool." The cultures in the eight secondary pool plates and the one tertiary pool plate were pelleted and stored at −20° C. The remaining cultures in the two sets of deep 96-well plates were stored in 50% glycerol at −80° C. (one working library with the second as back-up).

PCR Screening

Figure 1:
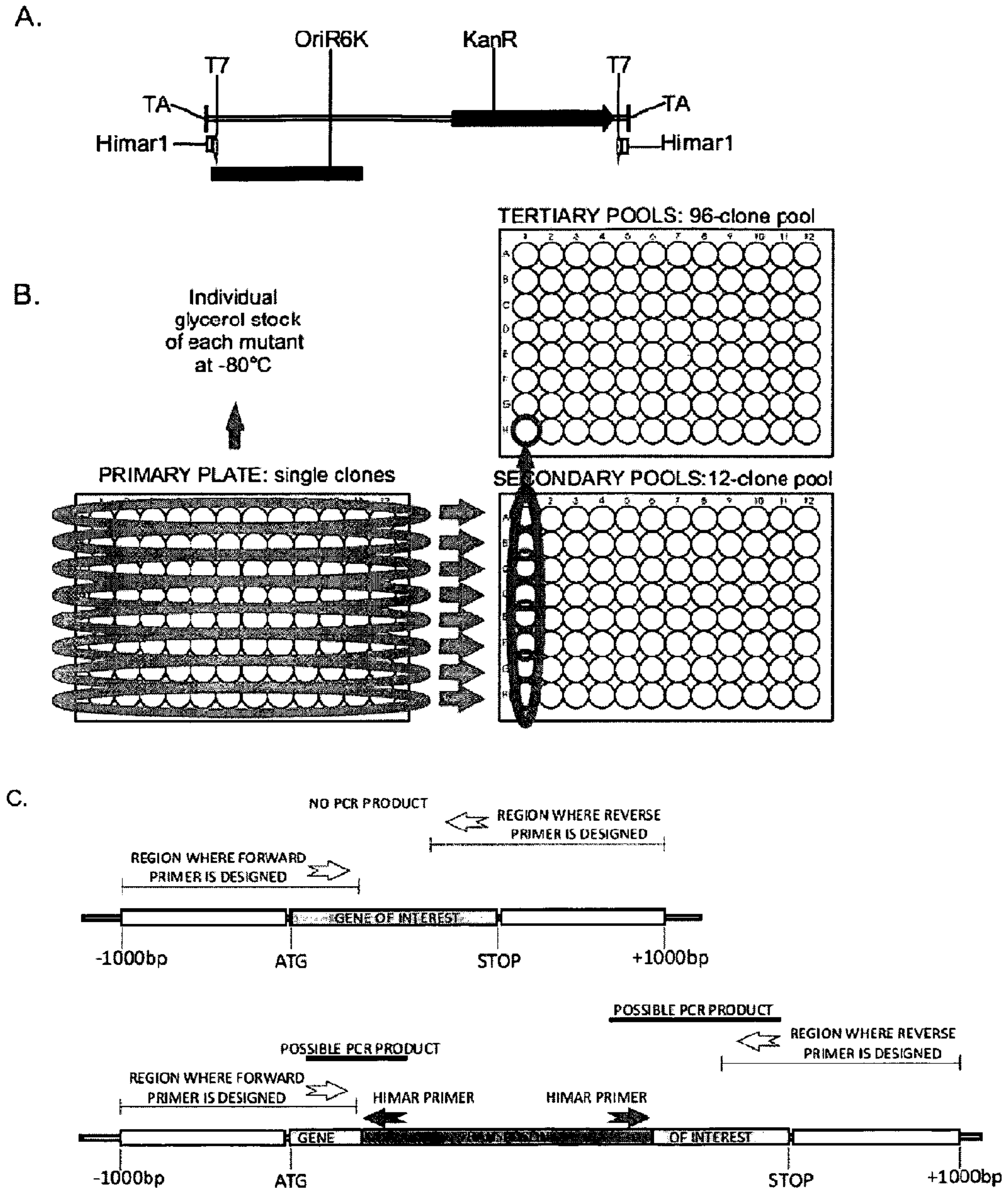
FIG. 1: Generation of an ordered transposon insertion mutant library and schematic representation of the four selected mutants.
Figure 1:
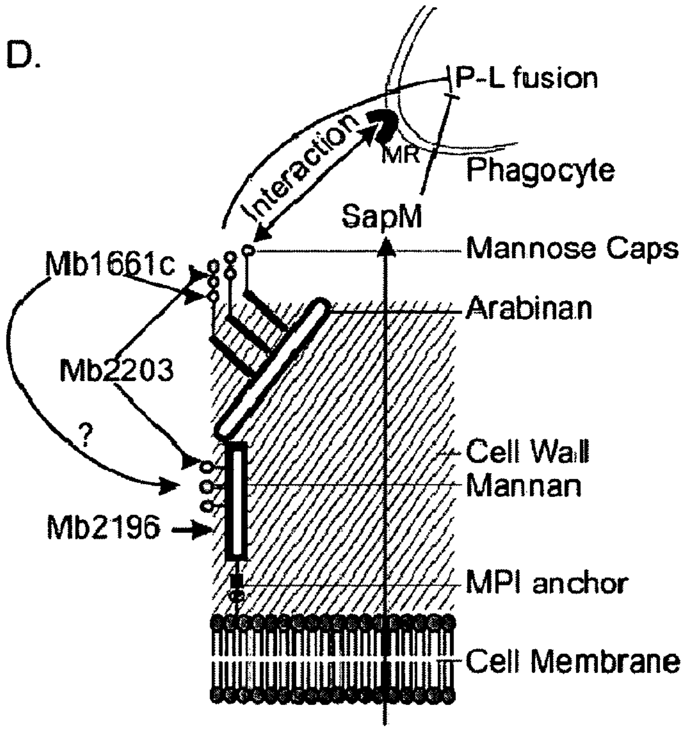

For each gene of interest, a primer that hybridizes anywhere in the 1000 bases upstream or downstream of the coding sequence was designed using one of the following software packages: Primer Excel, Oligo or DNA Star. The primers were aligned against the *M. bovis* BCG genome (on the worldwide web at genolist.pasteur.fr/BoviList/) to ensure that the primer was as gene specific as possible. PCR was performed using this primer and a second primer that hybridized within the inverted repeats flanking the transposon (FIG. 1, Panel C). This primer reads away from the transposon and into the adjacent genomic sequence of the insertion, irrespective of its orientation with respect to the target sequence. We first screened the tertiary pools for the presence of transposon insertions in each target locus and then the secondary pools. The final 12 mutants (one row in the primary library plates containing one mutant per well) were then grown up from glycerol stocks and screened again to identify the individual mutant with the insertion (FIG. 1, Panel B). The region of the genome amplified by the primers was sequenced to confirm insertion in the gene of interest. The genomic DNA of the mutants was prepared as described[37] and approximately 30 ng was used per PCR reaction. PCR was set-up using the Amplitaq Gold (Amersham, Uppsala) polymerase and buffer set.

Characterization of the Mutants by Southern Blotting

Genomic DNA of the mutants was digested with BamHI and PstI (restriction sites absent in the transposon) in sequence. The digested samples were blotted to Hybond N+ membranes (Amersham, Uppsala) by the neutral denaturing procedure (as per manufacturer's instructions). We hybridized the membranes with the full-length transposon sequence, labeled with 250 μCi [α-$^{32}$P] dCTP (Amersham, Uppsala) by random priming (Random Prime Kit, Amersham, Uppsala).

Quantitative Real Time PCR

Log phase cultures of wild-type *M. bovis* BCG and mutants (OD600 0.8-1.0), were pelleted and resuspended in TRI reagent (Molecular Research Center, Inc., USA), in a ratio of 1 ml reagent per 50 mg pellet. One-tenth μM baked glass beads were added and the pellet disrupted in a Retsch MM2000 bead beater (Retsch GmbH, Germany) at maximum amplitude for three minutes at 4° C. The supernatant was collected by centrifugation at 13,000 rpm, two minutes at 4° C. and extracted with equal volumes of chloroform. The aqueous layer was collected and the RNA precipitated with 0.6 volumes of isopropanol. This solution was loaded on an RNEASY® mini column (RNEASY® Mini kit, Qiagen, USA) and further steps followed according to the Qiagen protocol for RNA extraction with the exception that, after DNase treatment, RNA was eluted in a final volume of 50 μl of DEPC water. Ten μl of the RNA obtained was used as template for cDNA synthesis using the iScript cDNA Synthesis Kit (Bio-Rad, USA). The cDNA obtained was diluted 1:5 and 2 μl used in a Q-PCR reaction using the Fast SYBR Green Master Mix (Applied Biosystems, USA). The samples were analyzed on the LightCycler Real Time PCR System (Roche Applied Science, Switzerland). The primers used for the analysis were designed downstream of the transposon insertion site in the mutants (as determined by sequencing). The PCR was done a total of three times for each sample and the mean results were used as the value for each sample.

Analysis of Phosphatase Activity

Late log phase cultures of wild-type *M. bovis* BCG and *M. bovis* BCG SapM mutant ($OD_{600}$ 4), were pelleted and the supernatans was evaluated for phosphatase activity, using p-nitrophenyl phosphate (pNPP) as the substrate.[52] Fifteen μL pNPP (5 mM final) was added to 50 μl culture supernatant in a total volume of 150 μL (adjusted with 0.1 M sodium acetate pH6). Samples were incubated at 37° C. for the indicated time points before stopping the reaction with 50 μL 1 M $Na_2CO_3$. The relative rate of hydrolysis of pNPP was determined by quantification of released pNP and Pi at 415 nm.

Growth Curves and Ultra-Structure

We cultivated all strains in 10 ml of Middlebrook 7H9 broth (no antibiotic selection) at 37° C. and recorded absorbance at 600 nm once every 24 hours for a period of four weeks. For electron microscopy, mycobacterial cells were frozen in membrane carriers in a high pressure freezer (EM Pact, Leica Microsystems, Vienna, Austria). Freeze substitution was carried out in a Leica EM Automatic Freeze Substitution (AFS). Over a period of four days, the cells were substituted in dry acetone with 1% osmium, 0.2% glutaraldehyde and 0.1% uranyl acetate (UrAc) as follows: −90° C. for 26 hours, 2° C./hour temperature increase over 15 hours, −60° C. for eight hours, 2° C./hour temperature increase over 15 hours, −30° C. for eight hours. At −30° C., the carriers were rinsed three times with acetone for 20 minutes each time. At the end, cells are warmed up slowly to 4° C. Subsequently, we impregnated cells stepwise in Spurr's resin, which we polymerized at 70° C. for nine hours. We cut ultra-thin sections of gold interference color using an ultra-microtome (ultracut E, Reichert-Jung) and collected them on formvar-coated copper slot grids. We stained the sections for one hour with 50:50 (v/v) glutaraldehyde 4% and a 0.2 M cacodylate buffer containing 1.5 g/L ruthenium red followed by rinsing in 0.2 M cacodylate buffer. We subsequently stained the sections for four hours with a freshly prepared solution of 50:50 (v/v) osmium tetroxide 4% in $ddH_2O$ and 0.2 M cacodylate buffer containing 1.5 g/L ruthenium red, followed by rinsing in the cacodylate buffer and then $ddH_2O$. We visualized the grids with a JEOL 1010 TEM operating at 90 kV.

Cyanovirin-N Binding and Mannosidase Treatment

One mg (wet weight) of *M. bovis* BCG wild-type or mutant cells (culture OD600~1.0) were incubated with 1 μl of Cyanovirin-N (702.9 μg/ml, received as a gift from Dr. B. O'Keefe, NIH, Bethesda) coupled to Alexa-488 (according to manufacturer's instructions, Molecular Probes) in 100 μl of lectin buffer (50 mM Tris/Cl pH 7.5, 150 mM NaCl, 1 mM $MgCl_2$, 1 mM $CaCl_2$, 1 mM $MnCl_2$) for one hour on ice and assessed via flow cytometry on a FACS Calibur (Becton Dickinson) flow cytometer. Just before analysis, 15 μM of propidium iodide (PI) was added into the sample. For the α-1,2-mannosidase treatment, 1 mg of cells were incubated overnight at 37° C. in 100 mM ammonium acetate buffer (pH 5.0) with 33 ng of recombinant *Trichoderma reesei* α-1,2-mannosidase in 50 uL (LPS-free, produced in *Pichia pastoris* inhouse).[34] The cells were then washed once with the buffer and the Cyanovirin-N staining performed as given above, followed by flow cytometric analysis.

CS-35 Labeling

One mg (wet weight) *M. bovis* BCG wild-type or mutant cells (culture OD600~1.0) were incubated with 1:100 diluted CS-35 monoclonal antibody (TBVTRM, Colorado State University)[22] for 15 minutes in 1×PBS pH 7.4, in a reaction volume of 100 μl, following which anti-mouse IgG-PE (Phycoerythrin, Molecular Probes, USA) was added and additionally incubated for 15 minutes. The cells were briefly washed in 1×PBS and analyzed via flow cytometry.

Isolation of LM and LAM

We isolated lipoglycans on a small scale following the protocol described.[23] Briefly, 50 mg of cells (wet weight) from a culture at OD 1.0 (or 0.4-0.5 in case of low OD cultures), were extracted in chloroform:methanol:water (10:10:3) for 30 minutes at 50° C. The pellet was then incubated with buffer-saturated phenol for two hours at 80° C. and extracted with equal volumes of chloroform. The aqueous phase was collected and dialyzed against water.

SDS-PAGE and In-Gel Lectin Blot (In-Gel Western)

The lipoglycan samples (derived from 10 mg of cells) were analyzed on 12% SDS-PAGE gels without stacking gels followed by Periodic acid-Schiff staining.[48] The in-gel western was performed by incubating the gels for one hour in blocking buffer (In-gel western kit, Westburg, Leusden, The Netherlands) followed by an overnight incubation in lectin buffer with Cyanovirin-N (received as a gift from Dr. B. O'Keefe, NIH, Bethesda) coupled to Alexa-633 (according to manufacturer's instructions, Molecular Probes) at 4° C. Shorter incubations times were tried but resulted in very low signal strength. The gel was washed thoroughly for one hour in lectin buffer and visualized at 700 nm using the Odyssey Infrared Imaging System (Westburg, Leusden, The Netherlands) and read-outs made in grey-scale.

DSA-FACE Analysis of *M. Bovis* BCG and Isolated LM and LAM Samples

Lipoglycan samples were subjected to mild acid hydrolysis by boiling them for five minutes in 10 μl of 10 mM HCl, followed by neutralization with an equal volume of 10 mM NaOH. We desalted the samples using porous-graphitized-carbon (Nu-tip) tips (SunChrom GmbH, Friedrichsdorf, Germany) as described previously.[46] We vacuum-evaporated the desalted sample and labeled them with APTS, followed by analysis by capillary electrophoresis on the ABI 3130 DNA sequencer (Applied Biosystems, Foster City, USA) as described.[30] One μl of the APTS-labeled samples were then digested overnight at 37° C. in 0.1 μl of 100 mM ammonium acetate buffer (pH 5.0), with 6 ng of recombinant *T. reesei* α-1,2-mannosidase and the volume made up to 2 μl with milli-Q water. The samples were then analyzed by capillary electrophoresis as above.

Lipid Extraction and Mycolic Acid Analyses by Thin-Layer Chromatography.

We grow the mycobacterial strains (5 ml to an OD600 nm of 0.4 in the presence of 0.05% TWEEN® 80 in Middlebrook 7H9 broth (Difco) and 10% ADC (Difco) with appropriate antibiotics (wild-type: 100 μg/ml Streptomycin, and mutants: 100 μg/ml Streptomycin and 50 μg/ml Kanamycin) at 37° C. At this point, 1 μCi/ml [1,2-14C]acetate (57 mCi/mmol, GE Healthcare, Amersham Bioscience) was added to the cultures, which were further incubated at 37° C. for 24 hours. The [14C]-labeled cells were harvested by centrifugation at 2000×g, washed with PBS and processed as described below.

We initially resuspended the [$^{14}$C]-labeled cells in $CH_3OH$/0.3% NaCl (2 ml, 100:10, v/v) and mixed them with 1 ml of petroleum ether (60-80° C.) for 15 minutes. The upper petroleum ether layer was removed and a further 1 ml of petroleum ether added, followed by further mixing for 15 minutes. The petroleum ether extracts were combined and evaporated under nitrogen using a heating block. The dried apolar lipid extract was resuspended in 200 μl of $CH_2Cl_2$ prior to thin-layer chromatography (TLC) and autoradiography. Polar lipids were extracted by the addition of $CHCl_3$/$CH_3OH$/0.3% NaCl (2.3 ml, 9:10:3, v/v/v) to the lower methanolic saline phase and mixed for one hour. The mixture was centrifuged and the pellet reextracted twice with $CHCl_3$/$CH_3OH$/0.3% NaCl (750 μl, 5:10:4, v/v/v). $CHCl_3$ (1.3 ml) and 0.3% NaCl (1.3 ml) were added to the combined extracts and the mixture centrifuged. The lower layer containing the polar lipids recovered and dried. The polar lipid extract was resuspended in $CHCl_3$/$CH_3OH$ (2:1, v/v). We applied the apolar and polar lipid extracts (50,000 cpm each) to the corners of 6.6×6.6 cm plates of silica gel 60 F254 (Merck 5554) TLC plates. The plates were developed in a series of solvent systems, designed to cover the whole range of lipid polarities as described. For apolar lipid extracts these systems were named systems A-D and for polar lipid extracts, system E. System A TLCs were run thrice in direction 1 (petroleum ether 60-80: ethyl acetate 98:2) and once in direction 2 (petroleum ether 60-80: acetone 98:2). System B TLCs were run thrice in direction 1 (petroleum ether 60-80: acetone 92:8) and once in direction 2 (toluene:acetone 95:5). Systems C, D and E TLCs were run once in each direction using, for system C, $CHCl_3$:$CH_3OH$ (96:4) in the first direction and toluene:acetone (80:20) in the second; for system D, $CHCl_3$:$CH_3OH$:$H_2O$ (100:14:0.8) in the first direction and chloroform:acetone:$CH_3OH$:$H_2O$ (50:60:2.5:3) in the second; and for system E, $CHCl_3$:$CH_3OH$:$H_2O$ (60:30:6) in the first direction and $CHCl_3$:acetic acid:$CH_3OH$:$H_2O$ (40:25:3:6) in the second. Autoradiograms were produced by overnight exposure of Kodak X-Omat AR film to the plates to reveal [14C]-labeled apolar and polar lipids. For extraction of mycolic acid methyl esters (MAMEs), the delipidated cells from the 5 ml cultures were subjected to alkaline hydrolysis with 5% aqueous TBAH at 100° C. overnight, followed by the addition of 4 ml $CH_2Cl_2$, 500 μl $CH_3I$, 2 ml water, followed by mixing for 30 minutes. The upper aqueous phase was discarded following centrifugation, and the lower organic phase washed thrice with water and evaporated to dryness. The resulting MAMEs were dissolved in diethyl ether, insoluble residues were removed by centrifugation, and the ether solution evaporated to dryness and redissolved in 200 μl of $CH_2Cl_2$. Equivalent volumes (5 μl) of the resulting solution of MAMEs was subjected to TLC with silica gel plates (5735 silica gel 60F254; Merck), developed in petroleum ether-acetone (95:5). Autoradiograms were produced by overnight exposure of Kodak X-Omat AR film to the plates to reveal [$^{14}$C]-labeled MAMEs.

Macrophage Cells

Isolation and routine culture of the murine macrophage clone Mf4/4 has been described previously (Desmedt et al., 1998). The cells were cultured in RPMI 1640 medium supplemented with 10% fetal calf serum, L-glutamine (0.03%), 0.4 mM sodiumpyruvate, 0.1 mM non-essential amino acids and 50 μM (3-mercaptoethanol.

Generation of Bone Marrow-Derived Dendritic Cells

Bone marrow cells were cultured for eight days in DC culture medium (RPMI 1640 containing GlutaMAX-I, supplemented with 5% (vol/vol) FCS, 50 μM β-mercaptoethanol and 20 ng/mL GM-CSF (produced in house).

Laboratory Animals

Female C57BL/6 mice and BALB/c mice were purchased from Janvier (France) and were housed under specific pathogen-free conditions in microisolator units. Animals were used at seven to eight weeks at the beginning of the experiment. All experiments were approved by and performed according to the guidelines of the animal ethical committee of Ghent University and SIPH, Belgium.

*M. bovis* BCG Vaccination and *M. tb* Challenge

Female BALB/c mice were vaccinated subcutaneously with $10^5$ CFU of the parental or mutant *M. bovis* BCG strains grown on 7H9-OADC medium (30 mice/group). Mice were challenged intravenously three months after BCG vaccination with $5\times10^4$ CFU luminescent *M. tb* H37Rv, grown for two weeks on liquid 7H9-OADC medium (Tanghe et al., 2001). Bacterial replication in spleen and lungs was monitored by luminometry. Mice were sacrificed on weeks 2, 4 and 8 post-infection (four to five mice/group), as indicated in the text. Luminescence was measured in a Turner Design Luminometer as flash emission (15-second integration time) using 1% n-decanal (Sigma) in ethanol as substrate. In this assay, only live bacteria are enumerated, because emission of light is dependent on the presence of reduced flavin mononucleotide ($FMNH_2$), co-factor that is only found in living cells. At least ten additional mice/group were monitored for weight loss and mortality in a long-term survival experiment as reported before (Romano et al., 2006).

Cytokine Production Following Splenocyte and Lung Cell Stimulations

BALB/c mice were infected intravenously ($10^6$ cells/mouse in 200 μl in tail vein) with the *M. bovis* BCG wild-type or mutant. Four weeks after infection, mice were killed by cervical dislocation and lungs and spleens were removed aseptically. Cells were isolated by use of a loosely fitting Dounce homogenizer, washed and adjusted to a concentration of $2\times10^6$ cells/mL, and grown in round-bottom microwell plates (Nunc), in RPMI 1640 medium, supplemented with 10% fetal calf serum, L-glutamine (0.03%), 0.4 mM sodiumpyruvate, 0.1 mM non-essential amino acids and 50 μM β-mercaptoethanol. Recombinant Ag85a (5 μg/mL; Colorado State University) and the synthetic 20-mer peptide p11 (Ag85A99-118aa, dominant CD4 T cell epitope (Denis et al., 1998) were used to stimulate the cells in a volume of 100 μL of cell suspension (in triplicate). Cells were incubated at 37° C. in a humidified $CO_2$ incubator, and supernatants were harvested after 72 hours. Supernatants were frozen at −20° C. until assay. The IFNγ concentration was determined by ELISA.

Flowcytometric Analysis of Binding/Uptake of Mycobacteria by Macrophages and BMDCs Mf4/4 macrophages were kept in 24-well plates at 37° C. to reach $2\times10^5$ cells/well at the time of infection. Log phase *M. bovis* BCG wild-type and mutants (OD~0.8-1.2) were FITC labeled by resuspending the bacterial pellet (10 mg wet weight) in 200 μL of a FITC solution (0.1 mg/mL FITC isomer 1 (Sigma Aldrich) diluted in 0.1 M $NaHCO_3$, pH 9) and incubating this bacterial suspension at 25° C. for one hour with gentle shaking. Following this incubation period, bacteria are washed in PBS until the supernatant is clear of residual FITC. The bacteria were used for infection of Mf4/4 cell monolayers or BM-DCs at an MOI of ten or two, respectively, and incubated for the indicated time points at 37° C. Macrophages were washed after infection, fresh medium was added and the infected cells were further incubated at 37° C. Before measurement, macrophages were washed two times with PBS and detached in non-enzymatic dissociation buffer (Gibco, Invitrogen NV). Infected BM-DCs were centrifuged for ten minutes at 150×g and washed in PBS. The amount of FITC-positive macrophages/BM-DCs was determined in FL1 on a FACS Calibur flow fluorocytometer (Becton Dickinson) equipped with a 488 nm argon ion laser.

Infection of Macrophages with *M. Bovis* BCG and Evaluation of Survival and Phagolysosome Fusion Macrophages were infected as described above. The number of CFU after the indicated time points was determined. For evaluation of phagolysosome formation by confocal microscopy, the cells were infected with FITC-labeled BCG. At three hours post-infection, cells were incubated with Lysotracker Red DND-99 (200 nM) for 30 minutes. Cells were washed, and subsequently placed in medium without Lysotracker. Image fields were picked at random under transmission light (non-fluorescent) and each image field contained at least 20 macrophages. For experimental details, see below.

Measurement of Oxidant Activity

Log phase *M. bovis* BCG wild-type and mutants were used to infect Mf4/4 cells (MOI 10). At the indicated time points, cells were washed with PBS and incubated for 30 minutes with 100 nM CM-$H_2$DCFDA (Molecular Probes). Afterwards, cells were washed in PBS again and analyzed for intracellular fluorescence on a FACScalibur flow cytometer equipped with a 488 nm argon ion laser.

Induction of Autophagy

To analyze autophagy following *M. bovis* BCG infection of macrophages or BM-DCs, the latter were infected with *M. bovis* BCG wild-type versus mutants at, respectively, MOI 10 or MOI 2 for four hours or 24 hours. Autophagy was also induced with rapamycin as previously described (Gutierrez et al, 2004). Cells were lysed in NP-40 lysis buffer (1% NP-40, 200 mM NaCl, 5 mM EDTA, 10% glycerol, 10 mM Tris-HCl pH 7.5, protease inhibitors). We analyzed 40 μg total protein on western blot (17.5% SDS-PAGE), which was revealed with monoclonal anti-LC3 antibody clone 5f10 (Nanotools, Enzo Life Sciences) and anti-mouse-HRP (Amersham).

LC3-I (18 kD), LC3-II (16 kD)

Lymph Node DC Trafficking and Activation

Eight-week-old female Balb/cJ mice (Janvier, France) were infected subcutaneously at the base of the tail with $1\times10^6$ CFU *M. bovis* BCG wild-type and *M. bovis* BCG SapM mutant in 100 μL PBS (five mice/group). Day 1 and day 7 post-infection, five mice per group were sacrificed; inguinal and brachial/axillary lymph nodes were removed aseptically, and homogenized in RMPI with 1% collagenase (shaking 45 minutes at RT). Cells were prepared and labeled with CD11c-APC, MHCII-FITC, CD80-V450, CD40-PE, CD8a-PerCP, CD86-PE-Cy7 and analyzed on a LSRII flow cytometer (BDTM). Analysis was performed using FACSdiva software.

Statistical Analyses

For statistical analysis, results obtained in milliRelative Light Units (mRLU) were converted to mean log 10 mRLU/organ. Survival data were analyzed using the method of Kaplan-Meier and Logrank test in Prism version 4.0 (GraphPad). The other data were analyzed with one-way ANOVA or Kruskal-Wallis followed by Bonferroni's Multiple Comparison Test or Mann-Whitney U test as indicated. P values <0.05 were considered statistically significant.

Cells

The macrophages used in these experiments are derived from a clonal, immortalized C57BL/6-derived population that both functionally and phenotypically expresses features characteristic of mature macrophages. Thus, these Mf4/4 cells express the surface molecules BM-8, F4/80, Mac-1, Mac-2, and CD14 that have been described for mature macrophages; they can exert receptor-mediated phagocytosis and produce IL-1, IL-6, IL-12, and TNF in response to LPS, but not to IFN-γ. Moreover, the Mf4/4 cells express increased levels of MHC class II Ags after treatment with IFN-γ and concomitantly acquire the capacity to present exogenous Ag to CD4+ T cells. These features demonstrate that, despite their transformed state, the Mf4/4 cells retain their macrophage-specific constitutive and inducible functions. We could also demonstrate the expression of mannose receptor by competing the binding of FITC-mannose BSA with α-methyl-D-mannopyranoside (data not shown).

Analysis of Uptake of *M. Bovis* BCG by Confocal Microscopy

Mf4/4 cells, grown on one-well glass bottom dishes (Willco Wells B.V., Amsterdam, The Netherlands) and labeled with Cell tracker red (Molecular Probes, 10 μM final, pre-incubated for 30 minutes in serum-free medium), are infected with FITC-labeled *M. bovis* BCG (MOI 10). After three hours at 37° C., confocal images were acquired with a 63×HCX PL APO 1.4 NA OIL UV-corrected objective on a Leica TCS sp5 AOBS laser scanning inverted DMi6000 microscope. FITC was excited with the 488 nm line of a Multi Argon laser and Cell tracker red with a 543 nm HeNe. Sequential scanning was performed to exclude cross-excitation bleed through. FITC and Cell tracker red were detected with the respective emission bandwidths: 500 nm till 540 nm and 550 nm till 700 nm. Images were taken with a 512×512 pixel resolution, using a 4× zoom, resulting in a pixel size of 123 nm. Twenty-three z-layers were recorded with a step size of 0.26 μm.

Electron Microscopy of Macrophages Infected with *M. Bovis* BCG Wild-Type and Mutants Mf4/4 cells were infected with *M. bovis* BCG wild-type and mutants (MOI 10) for three hours. Following infection, the cells were washed two times in PBS, fixed in 4% paraformaldehyde and 2.5% glutaraldehyde in 0.1 M NaCacodylate buffer, pH 7.2 for four hours at RT followed by fixation 0/N at 4° C. After washing three times 20 minutes in buffer, cells were dehydrated through a graded ethanol series, including a bulk staining with 1% uranyl acetate at the 50% ethanol step followed by embedding in Spurr's resin. Ultrathin sections of a gold interference color were cut using an ultramicrotome (Leica EM UC6), followed by a post-staining with uranyl acetate and lead citrate in a Leica EM AC20 and collected on formvar-coated copper slot grids. They were viewed with a transmission electron microscope 1010 (JEOL, Tokyo, Japan).

Evaluation of Phagolysosome Fusion

Confocal images were acquired with a 63×HCX PL APO 1.4 NA OIL UV-corrected objective on a Leica TCS sp5 AOBS laser scanning inverted DMi6000 microscope equipped with a 37° C. incubation chamber (Leica Microsystems, Wetzlar, Germany). FITC was excited with the 488 nm line of a Multi Argon laser and emission light was captured between 500 and 540 nm. Lysotracker Red (Molecular Probes) was excited with a 543 nm HeNe laser line and emission light was captured between 560 and 620 nm. Sequential scanning was always performed, scanning zoom was set at 2.0 and z-series image stacks were collected over the complete depth (in z-axis) of the macrophages. Depending on the experiment, two different imaging setups were used: in the first (low resolution) setup, the image size was 512×512 pixels and z-intervals were set at 1.0 μm, resulting in 240×240×1000 $nm^3$ voxels. In the second and third (high resolution) imaging setups, 1024×1024 pixel images were taken with 0.25 μm z-stepsize, resulting in 120×120×250 $nm^3$ voxels. Phagolysosome fusion was evaluated by analyzing colocalization between FITC and lysotracker Red with the JaCoPplugin of the ImageJ 1.3i public domain imaging software (Abramoff et al, 2004; Rasband & ImageJ, 2008). Thresholded Manders' M1 coefficients were used to measure the amount of bacteria that had undergone phagolysosomal fusion and are defined as the ratio of the "summed intensities of pixels from the FITC channel for which the intensity in the lysotracker Red channel is above zero" to the "total intensity in the FITC channel" (Bolte & Cordelières, 2006). Thresholds for the Manders' M1 coefficient were set automatically without user intervention based on the image histogram. Three independent experiments were performed in which twenty (first experiment; low resolution setup) or ten (second and third experiments; high resolution setup) z-series image stacks were taken per strain.

Replication of *M. Bovis* BCG Following Infection of Mice

Eight-week-old female Balb/cJ mice (Janvier, France) were infected intravenously with $1\times10^6$ CFU *M. bovis* BCG wild-type and mutants in 200 μL PBS. Two weeks, four weeks and twelve weeks post-infection, five mice per group were sacrificed; lungs and spleens were removed aseptically, and homogenized in PBS. Neat, 1/10 and 1/500 dilutions were made, 100 μl was plated in duplicate on 7H10-OADC agar, and the colonies were counted at 21 days. The CFU counts were based on the highest dilution showing distinct colonies.

Granuloma Formation and Cytokine Measurements Following Infection of Mice with *M. Bovis* BCG C57BL/6 mice were anesthetized and infected intravenously with $1\times10^6$ CFU, or intratracheally with $0.5\times10^6$ CFU, *M. bovis* BCG wild-type and mutants. After three and four weeks respectively, five mice per group were sacrificed, livers and lungs were removed aseptically, and fixed in 3.7% paraformaldehyde prior to embedding in paraffin for thin sectioning. General morphology and inflammation were examined by hematoxylin/eosin staining (Merck, VWR international). Quantitative studies were performed by direct microscopic examination and analysis with ImageJ software. Bronchoalveolar lavage (BAL) was performed four weeks post-infection and cytokine levels in BAL fluid were determined using Cytometric Bead Array and Flex sets according to manufacturer's instructions (BD Biosciences).

Cytokine Production Following Infection of BM-DCs with *M. bovis* BCG Wild-Type Versus SapM::T BM-DCs were infected for six hours with *M. bovis* BCG wild-type versus mutants. Following infection, the BM-DCs are collected by centrifuging at 150×g ten minutes, 4° C. Cells are washed in PBS and brought back in culture for 24 hours and 48 hours. At the indicated time points, supernatant was removed and analyzed for the presence of cytokines by flow cytometry (BioPlex Pro Cytokine Express Assay, Biorad).

Coculture of BM-DCs and iNKT Hybridomas

Wild-type and CD1d−/− BM-DCs ($1\times10^6$ cells) were infected with *M. bovis* BCG wild-type versus mutants for 24 hours (MOI 2). Following infection, the cells were washed with PBS and put in coculture with the iNKT cell hybridoma 2C12 (Brossay et al., 1998a; Brossay et al., 1998b) ($50\times10^3$ BM-DCs: $25\times10^3$ iNKT). As a control, BM-DCs were loaded with α-GalCer (100 ng/mL per $1\times10^6$ cells) and incubated at 37° C. for two hours before setting up the coculture with the 2C12 cells. At the indicated time points, supernatans were collected and IL-2 and IL-12p40 production was analyzed by flow cytometry (BioPlex Pro Cytokine Express Assay, Biorad). Cells were labeled with panel 1 (CD11c-PerCP-Cy5.5, MHCII-FITC, PD-L1-PE, CD86-PE-Cy7, CD80-V450, CD40-APC), panel 2 (CD11c-PerCP-Cy5.5, MHCII-FITC, CD1d-PE) and panel 3 (CD11c-PerCP-Cy5.5, TCRβ-FITC, CD1d aGalCer tetramer-PE, CD69-V450) and analyzed on a LSRII flow cytometer (BDTM). Analysis was performed using FACSdiva and Flowjo software (Tree Star, Inc.).

Example 1

Generation and Screening of *M. bovis* BCG Mutants

Transposon delivery by mycophages is a highly efficient method for the generation of saturation-mutagenesis libraries of mycobacteria.[54] The method makes it possible to generate a wide variety of mutants in an isogenic background, which is ideal for comparison of the effects of different gene mutations. The insertion of the transposon into a gene most often leads to its inactivation and reversion frequencies are usually very low.[47] The transposon can also be used to deliver additional markers like antibiotic resistance genes. It also allows for the transposon flanking genomic regions to be amplified and identified by sequencing.[27] Transposon mutagenesis has been successfully used in both fast and slow-growing mycobacterial strains.[1, 10, 32, 51] Here, we have created a 96×96 clone, ordered *M. bovis* BCG transposon insertion mutant library using the Himar1-derived minitransposon delivered by the temperature-sensitive MycomarT7 phage.[49]

Moreover, we have developed a PCR-based screen of this ordered library to rapidly identify insertions in targeted open reading frames of interest. The system was validated by screening the library for insertions in genes involved in cell wall component biosynthesis or of reported importance in mycobacterial virulence.

Library Construction and Ordering

*M. bovis* BCG 1721,[36] a derivative of *M. bovis* BCG Pasteur, carrying a non-restrictive rpsL alteration resulting in streptomycin resistance, was used as parental strain in the construction of the ordered transposon insertion library in *M. bovis* BCG by using a Himar1-based mariner transposon and mycomarT7 donor phagemid[56] (FIG. 1, Panel A). Mutants were selected for double antibiotic resistance (kanamycin and streptomycin). The library yielded about 100,000 mutants, 9216 (96×96 well plates) of which were hand-picked to create an ordered library as previously described (FIG. 1, Panel B).[29] Briefly, the single clones from each row of a 96-well plate were pooled to form a "secondary pool" (FIG. 1, Panel B) and aliquots from each column of this secondary pool plate were pooled into a single well to form a "tertiary pool." Due to the property of mycobacteria to clump and thus frequently faun fused colonies, robotic clone picking would be very difficult. Hand picking of clearly individual clones from the plates was deemed necessary to reduce the frequency of mixed culture in the ordered library. The genome size of *M. bovis* BCG is 4.4 Mb and, as the transposon can insert in every TA sequence,[28] theoretically, an insertion is expected in our library every ~460 bp.

PCR Screening

Using a primer hybridizing to the inverted repeats at either ends of the transposon, and gene-specific primers either upstream or downstream (and occasionally in) the ORF of the target gene, we performed PCR screening of the ordered library (FIG. 1, Panel C). The library has been manually ordered into a series of pools in order to enable efficient PCR screening. Due to this, only two rounds of PCR (first 96 reactions, then eight reactions) are needed to identify the twelve-clone row in which the desired mutant is present (FIG. 1, Panel B). These twelve clones are then cultivated and genomic DNA is prepared for a final round of PCR to identify the mutant. If a primer is identified that gives gene-specific amplification in PCR round one, then the entire screen is completed in about four to five weeks (with most of that time required to grow the twelve final cultures). We completed screens for insertions in 19 ORFs (annotated not to be essential for growth in vitro (based on the presence of transposon mutants in these genes in *M. tuberculosis* libraries that were analyzed through TRASH[55]). Our screen was focused on genes involved in (Man)LAM biosynthesis and/or in interference with the phagosome-lysosome fusion event. The total screened size of these ORFs was ~11,120 bp. In these ORFs, we found a total of 22 transposon insertions (1/500 bp approximately), providing mutants in 15 of the 19 ORFs. Not surprisingly, three out of four unsuccessful screenings were for the three smallest ORFs (less than 750 bp). In this screening, primer design was critical. For most screenings, several gene-specific primers had to be tested for one to be found that yielded gene-specific amplification. This was mainly due to the fact that the *M. bovis* BCG genome has a very high GC content, with an average percentage G+C of over 65%.[16] This made it difficult to design primers that did not bind non-specifically elsewhere in the genome.

Example 2

Biochemical Characterization of Transposon Insertion Mutants

Southern Analysis for Confirmation of Single Transposon Insertion

The sequence-confirmed mutants were further characterized by Southern blotting with the full-length transposon as probe, to confirm the presence of a single transposon insertion in the genome. This is essential in order to ensure that the observed phenotype of a mutant is due to a transposon insertion, leading to the inactivation of the gene of interest alone. Apart from three mutants (FIG. 2, Panel A), all the rest showed a single transposon insertion.

Mutants in Mb1661c, Mb2203, Mb2196 and SapM

We obtained two mutants each for genes Mb1661c, Mb2203 and Mb2196 in our library screen. One of the mutants for the gene Mb2203 and for Mb2196 showed multiple transposon insertions when analyzed by southern blot analysis and was removed from further use. Among the two mutants for gene Mb1661c, we decided to work with the mutant where the insertion of the transposon was closer to the 5' end of the coding sequence (CDS), as proximity to the start of the CDS is even more likely to inactivate its functionality. Besides mutants in ManLAM biosynthesis, we also selected the mutant in the secreted acid phosphatase SapM as a control to assess any effects that the mere transposon presence might have on cell wall composition. For the gene SapM, we obtained only one mutant (Table 1). The site of transposon insertion in the four finally selected mutants was confirmed by cloning the fragments obtained by PCR screen using the TOPO TA® Cloning Kit (Invitrogen, USA) and sequencing the clones to determine the exact position of transposon insertion into the open reading frame (Table 1).

TABLE 1

List of mutants screened for by PCR in the ordered *M. bovis* BCG transposon insertion mutant library and described in this study

| Gene in H37Rv | Homologue AF2122/97 | Length (bp) | Length (aa) | (putative) function | Screening primer sequence (5' to 3') | No of mutants | Insertion at (in by from start codon) |
|---|---|---|---|---|---|---|---|
| Rv1635c | Mb1661c | 1671 | 556 | Man-T mannose capping of arabinan | *CACCACGGTCTTATAGGCGC* (SEQ ID NO: 19) | 2 | 470 and 344 (mutant ii) |
| Rv2181 | Mb2203 | 1284 | 427 | Man-T addition to mannan core and caps | *CCGTTCACCTCCACTG* (SEQ ID NO: 20) | 2 | 591* and 731 (mutant ii) |

TABLE 1-continued

List of mutants screened for by PCR in the ordered *M. bovis* BCG transposon insertion mutant library and described in this study

| Gene in H37Rv | Homologue AF2122/97 | Length (bp) | Length (aa) | (putative) function | Screening primer sequence (5' to 3') | No of mutants | Insertion at (in by from start codon) |
|---|---|---|---|---|---|---|---|
| Rv3310 | Mb3338 | 900 | 299 | PI3P phosphatase SapM | *ATCGTGGCTCGGTCCCCTAAA* (SEQ ID NO: 21) | 1 | -8 |
| Rv2174 | Mb2196 | 1551 | 516 | Man-T in synthesis of Man21-34 | *CGGTGACGACCTAAAGTCGG* (SEQ ID NO: 22) | 2 | 40* and 6 |

The Mutants Show Strong Reduction in Transcription of Gene of Interest and the Mutant in SapM Shows Decreased Phosphatase Activity Quantitative Real Time PCR (qRT-PCR) was performed on the wild-type *M. bovis* BCG 1721 and the mutants to compare expression levels of the genes of interest. RNA was extracted from mid-log phase cultures and cDNA synthesized using standard protocols. Q-PCR was performed with 16S rRNA as a reference. All mutants have strongly decreased abundance of the transcripts from the mutated gene as compared to the wild-type. The SapM mutant had almost no detectable transcription of the SapM gene (FIG. 2, Panel B), probably due to the insertion just upstream of the ORF, effectively separating the promoter from the ORF. Inactivity of SapM was also confirmed by a decreased phosphatase activity in the supernatans of the *M. bovis* BCG SapM::T culture compared to phosphatase activity in the supernatans of a wild-type culture (FIG. 2, Panel C). Residual phosphatase activity in the supernatans of the SapM mutant can still be due to the presence of other phosphatases.[3, 9]

Mutants have Unaltered Ultra-Structure and In Vitro Growth Rate

As the LAM molecule forms part of the cell wall (it is anchored in the cell membrane and extends through the inner and outer cell walls into the capsule), we wanted to assess whether the mutants in LAM biosynthesis show differences in the cell wall ultra-structure as compared to the wild-type. However, there were no overt differences in cell wall ultra-structure, as evident from the electron microscopy of thin sections stained to enhance the contrast of polar lipids and polysaccharides in the cell wall (data not shown). The mutants also show no retardation in growth in liquid medium as observed in the growth curve analysis (FIG. 3, Panel A). However, we did observe slight growth retardation in mutant Mb1661c when cultured on solid media (data not shown). All cultures grew at the same rate, although under our static growth conditions, doubling times increased with time and culture density (FIG. 3, Panel B). Doubling times were around 20-24 hours until an OD of 1-1.2 was reached, beyond which the doubling times steadily increased to 48-96 hours at higher ODs (~6) (for mutants as well as wild-type).

Cyanovirin-N Staining and DSA-FACE Analysis Reveals Differences in the α-1,2-Mannose Cap Structures in the Mb2203 and Mb1661c Mutants We analyzed the density of α-1,2-oligo-mannosyl glycotopes by flow cytometry with Cyanovirin-N lectin, which specifically binds oligo-α-1,2-mannose structures.[60] As a binding specificity control, the mycobacterial cells were also treated with recombinant α-1,2-mannosidase prior to the lectin staining. The mutants in Mb1661c and Mb2203 showed lower staining when compared to the wild-type, indicating that these mutants display less α-1,2-mannose linkages (data not shown). The mutants in SapM and Mb2196 show a similar staining profile as the wild-type, indicating that they have similar levels of α-1,2-oligomannoside linkages in their cell wall structure. These results are strengthened by the observation that when the wild-type strain or the SapM or Mb2196 mutants are treated with α-1,2-mannosidase, it shows a reduction in subsequent Cyanovirin-N staining (data not shown). This reduction is not observed in the mutants Mb1661c::T and Mb2203::T. This shows that, while the wild-type strain has α-1,2-mannose linkages available for the enzyme to act upon, the mutants Mb1661c::T and Mb2203::T do not.

To assess whether the reduced Cyanovirin-N staining in Mb1661c::T and Mb2203::T is reflected in the ManLAM capping structures, DNA sequencer-aided fluorophore-assisted carbohydrate electrophoresis (DSA-FACE)[31] was used to study the cap structures of ManLAM. We isolated the lipoglycan fractions from the cells using an extraction method, which can be performed at small scale and yields all lipoglycan species, rather than ManLAM only, making it more suitable for comparative analysis of mutants that may be affected in the exact structure of ManLAM. The preparation thus obtained is less pure than the standard ManLAM purified through a lengthy, very selective procedure,[62] but to the benefit of enabling more comprehensive lipoglycan profiling. Upon this isolation, we performed mild acid hydrolysis of the lipoglycans, which causes the acid labile α-1,5-araf linkages to be hydrolyzed, whereas the α-1,2- and α-1,6-mannose linkages are acid stable and are thus not hydrolyzed.[41] This results in the release of the α-1,2-oligomannoside-capped terminal structures of ManLAM. These samples were analyzed before and after α-1,2-mannosidase digestion. For the wild-type and the mutants SapM::T and Mb2196::T, several peaks were sensitive to α-1,2-mannosidase digestion (data not shown). These peaks had the same mobility as the α-1,2-mannosidase-sensitive peaks in the profile of the highly purified standard ManLAM, identifying them as the α-1,2-mannose cap bearing acid-resistant fragments of this molecule. The decrease in size by one or two hexose units corresponds to removal of one or two α-1,2-mannose residues from these ManLAM fragments. In the mutant Mb2203::T, no such α-1,2-mannosidase-sensitive structures are found, and instead, a profile is found that is consistently identical to the post-α-1,2-mannosidase profile of the wild-type. For Mb1661c::T, much lower levels of the α-1,2-mannosidase-sensitive structures were found than in wild-type, SapM::T or Mb2196::T. However, these structures were still present, indicating that there must be another yet-to-be-identified mannosyltransferase, which can very partially complement the Mb1661c mutation. Strikingly, a regular series of peaks was observed with a Poisson-like intensity distribution with increasing degree of polymerization. This was reminiscent of the acid hydrolysate of an α-glucan, as is used frequently as size standard in oligosaccharide analysis (data not shown).

Indeed, we confirmed through amyloglucosidase digestion that this is an α-1,4-linked gluco-oligosaccharide ladder. Such a glucan has been reported to be a major constituent of the capsular layer of the mycobacterial cell wall.[44] Thus, our sample preparation procedure likely leads to co-purification of part of this glucan. In fact, its presence allows estimating the relative abundance of ManLAM-derived oligosaccharides in the preparations from different mutants. Therefore, we interpret our findings of lower abundance of cyanovirin ligands on the mycobacterial cell wall as the compound result of both a somewhat lower ManLAM abundance and a lower but not absolute deficiency in synthesizing the oligo-α-1,2-mannosyl cap structures.

The Mutants do not Show Major Differences in Cell Wall Arabinan-Containing Components The monoclonal antibody CS-35 specifically binds α-1,5-linked arabinofuranosides (araf) (22). This glycotope is present in the arabinan side-chains of the LAM molecule and in arabinogalactan. Staining with this antibody will thus yield some information on alterations in the arabinan content of the cell wall in the mutants. The flow cytometry profiles of all the mutants with CS-35 antibody show no difference from wild-type profiles (data not shown).

Mutants Mb1661c::T and Mb2203::T Display Lower Molecular Weight and Noncyanovirin-N-Binding LAM SDS-PAGE analysis of the purified lipoglycan samples from the mutants versus wild-type was performed in order to determine the size of LAM and LM from the mutants when compared to wild-type (data not shown). The analysis revealed that the mutants Mb1661c::T and Mb2203::T have LAM that is of a smaller size, and the Mb2203::T LAM is the smallest. The sizes of LAM from the mutants SapM::T and Mb2196::T are the same as that of wild-type. The LM from all the samples appears to be of the same size, perhaps with the exception of the Mb2203::T mutant, where it appears larger. An in-gel western on these LAM samples was performed with the lectin Cyanovirin-N-Alexa-633 (data not shown). The results show that while the lectin binds the wild-type LAM and that from the mutant SapM::T, it does not bind the LAM samples from the three LAM mutants, indicating that these mutants lack the motifs for the lectin to bind under these conditions.

Analysis of LAM from Low OD Cultures

Both in vitro and in vivo infection studies using mycobacteria described in the literature are typically carried out with cultures growing in early to mid-log phase at ODs of 0.3-0.6 (referred to herein as low OD). Most of the above-observed biochemical analyses have been carried out with cultures growing at OD600 1.0. We have observed that cells at this culture density have higher in vitro infection efficiencies of macrophages than at low OD. We wanted to analyze the difference, if any, in the LAM content between the cultures growing at low OD600 0.5 and those grown to OD600 1.0. In order to do this, we grew cultures from the same glycerol stocks to two different ODs, isolated the lipoglycans, and analyzed them on SDS-PAGE followed by silver-PAS staining. We observed that at low OD, the amount of LAM produced is considerably less compared to the amount isolated from cells at a higher OD (data not shown). We also observed a presence, in greater amount, of the LM/LAM precursor, PIMs at low OD. We did not observe any PIMs in the lipoglycan samples from cultures at OD600 1.0. This indicates that LAM synthesis from the precursor PIMs only occurs efficiently when the cells are dividing slower, as occurs in our culture conditions as of OD600 1.0. The difference in LAM content may explain the difference in infection efficiencies, as interaction of ManLAM with the macrophage mannose receptor is one of the important entry pathways for the bacterium.[58]

ManLAM Biosynthesis Mutants do not Show Differences in Cell Wall Lipid Composition As mentioned earlier, the mycobacterial cell envelope is important for its virulence and consists of a peptidoglycan/arabinogalactanimycolic acid core, interacting with complex lipids ranging in polarity from apolar triacylglycerols (TAGs) and phthiocerol dimycocerosates (PDIMs) to polar glycolipids and lipo-oligosaccharides.[40] We have analyzed apolar and polar lipids from *M. bovis* BCG wild-type and its ManLAM biosynthesis mutants by two-dimensional thin-layer chromatography. The SapM mutant was used as a control to assess any effects that the mere transposon presence might have. The plates were developed in a range of solvent systems, designed to cover the whole range of lipid polarities (data not shown). Mycolic acid methyl esters (MAMEs) were extracted from delipidated cells and also analyzed on TLC (data not shown). We did not observe any difference in lipid composition between wild-type *M. bovis* BCG and the mutants, demonstrating that the transposon mutagenesis of ManLAM biosynthesis genes results in selective defects in this molecule and does not fundamentally alter the biosynthesis of other cell wall constituents nor the cell wall lipid composition.

Discussion

Many pathways are involved in aiding pathogenic mycobacteria to survive successfully within its host, even in the presence of an elaborate immune response.[7] An important aspect of this survival strategy is the inhibition by the bacterium of macrophage phagosome maturation. In the context of improved vaccine design for TB, inactivation of the virulence factors involved in, e.g., phagosome maturation inhibition, is an attractive strategy. As the only currently licensed vaccine for TB is *M. bovis* BCG, we chose to set up a rapid system to obtain mutants in *M. bovis* BCG in order to rapidly evaluate the effects of such mutations on the target pathways and on immunogenicity. Furthermore, the deletions that have occurred in deriving the BCG strains from virulent *M. bovis* have inactivated one of the pathways involved in the blocking of the phagosome-lysosome fusion[2, 61] making it more likely that mutations in other pathways involved in this process will give a clearer phenotype in this background than in *M. tb* or *M. bovis*, as less phenotypic complementation is expected. Moreover, the vaccine strain is very similar, genetically (99.9%) and physiologically, to *M. tb* while having the advantage of being non-pathogenic to immunocompetent humans, thus allowing its manipulation under standard biosafety conditions. This makes a rapidly screenable mutant collection a very useful resource for the wider TB research community. For all these reasons, we created a transposon insertion library of about 100,000 mutants in the *M. bovis* BCG background, 96×96 clones of which were manually picked and pooled to form an ordered library. This enabled rapid and efficient PCR screening of the library for mutants in any gene of interest, under condition that the gene is non-essential for in vitro growth. We obtained mutants for a majority of the genes that we screened for (15 out of 19). Screens for several more genes are currently ongoing. To validate the approach, we screened for mutants in genes involved in the biosynthetic pathway of ManLAM, a molecule known to contribute to key aspects of the pathogenesis of *tuberculosis*.[6, 63] We also screened for mutants in the secreted acid phosphatase SapM, which is also suspected to be important for intra-macrophage survival.[64] For the biochemical characterization of ManLAM mutants, the mutant in the PI3P phosphatase SapM served as a control to exclude any effects that the mere presence of the transposon might have on lipoglycan biosynthesis. The genes Mb1661c and Mb2203 are predicted to be α-1,2-mannosyltransferases involved in ManLAM modification (either in the poly-α-1,6-mannosyl backbone or on the terminal cap structures), based on analysis of their orthologues in *M. tuberculosis* and *M. smegmatis*.[12, 21] The current understanding is that in slow-growing pathogenic mycobacteria, Mb1661c is largely responsible for adding the first α-1,2-mannose residue in the cap structures, while the Mb2203-encoded enzyme synthesizes the di-mannosyl caps (and may elongate them to trimannosides as well).[24] However, in the study reporting the function of the Mb1661c homologue in *M. tb*, it was noted that the levels of ManLAM per cell in the knock-out was about ten-fold lower than in the wild-type,[11] indicating that this mutation has more profound effects on LAM synthesis than just affecting ManLAM capping. Consistent with this, we find that both Mb2203::T and Mb1661c::T mutants have strongly reduced cell surface abundance of α-1,2-oligomannosides, but this is reflected differently in the direct chemical lipoglycan analysis. Mb2203 inactivation yields a clear defect in synthesis of the di- and tri-mannoside caps, whereas, the Mb1661c inactivation results in a strongly reduced abundance of the caps, while the remaining ones still have intact structures, probably because of partial complementation of the defect by another, as-yet-to-be-identified transferase. Clearly, the Mb2203::T mutant is more specifically affected in the α-1,2-oligomannosyl capping of the ManLAM and is, therefore, more suitable for the analysis of the role of these caps in mycobacterial pathogenesis. Mb2196 has so far only had its orthologue characterized in the fast-growing non-pathogenic species *M. smegmatis* where its mutation caused the accumulation of a truncated LM and absence of LAM.[23] Our mutant in *M. bovis* BCG, Mb2196::T, displayed entirely wild-type behavior with regard to Cyanovirin-N cell wall staining and lipoglycan size analysis. In glycan analysis of acid hydrolysates of the lipoglycan extract, ManLAM cap structures were less abundant than for WT, but not as dramatic as for the Mb1661s mutant. This is partially inconsistent with the reported function of the homologous gene in *M. smegmatis* (one would expect no LAM synthesis, which may be the case, and accumulation of a truncated LM, which is not the case here). A further difference with the wild-type that was found was that ManLAM of Mb2196::T mutant did not stain with Cyanovirin-N under SDS-PAGE conditions. We speculate that this may be because of subtle alterations in the positioning of the α-1,2-oligomannoside caps along the molecule. Cyanovirin-N binds with high avidity to several α-1,2-oligomannoside branches of N-glycans at the same time,[60] while binding to single branches is much weaker. It may be that thus, under SDS-PAGE conditions, Mb2196 ManLAM is not properly structured for the high avidity binding. Further analysis is needed, but it is clear that Mb2196 mutation causes a more subtle phenotype in lipoglycan synthesis in *M. bovis* BCG than in *M. smegmatis*. It also illustrates that it is best to validate pathways with potential importance in pathogenesis in slow-growing *M. tb* complex strains, and our easily screenable *M. bovis* BCG mutant library is an efficient tool to that effect. In conclusion, the screenable mutant collection in *M. bovis* BCG allows rapid identification and characterization of a mutant of interest, e.g., the effect of mutations on BCG vaccine efficiency, with the hope of improving the suboptimal protection obtained with the only vaccine presently available to prevent *tuberculosis* (*M. bovis* BCG).

Example 3

Protective Efficacy of *M. bovis* BCG Wild-Type Versus Mutant SapM::T (Mb3338::T), Mb2203::T, Mb1661c::T and Mb2196::T in BALB/c Mice BALB/c mice were vaccinated subcutaneously with $10^5$ CFU of the parental or mutant *M. bovis* BCG strains. Three months post-vaccination, animals were intravenously infected with $5\times10^4$ CFU of luminescent *M. tuberculosis* H37Rv. Mice were sacrificed two, four, and eight weeks post-infection and the number of bacteria in spleen and lungs was determined by luminometry. Both parental and three mutant BCG strains offered significant protection against *M. tuberculosis* as indicated by ten- to 100-fold reduced numbers of bacteria in spleen and lungs as compared to unvaccinated TB infected mice (the Mb2196 mutant is currently being tested in this setting and is not yet included) (FIG. 4, Panel A and FIG. 5). In spleen, there was no difference in efficacy between the parental and mutant strains (FIG. 5), whereas in lungs, a significantly lower number of bacteria was found in mice vaccinated with the SapM::T mutant than in mice vaccinated with parental BCG at eight weeks post-infection (FIG. 4, Panel A). It is interesting to note that at eight weeks post-infection, the protective efficacy of the parental BCG started to decrease, whereas bacterial counts for all three mutants remained stable.

Mice were also followed for eleven months in a long-term survival study and monitored weekly for mortality and weight loss. Vaccination with both ManLAM capping mutants ($P<0.05$) and the SapM::T mutant ($P<0.005$) resulted in significantly longer survival as compared to nonvaccinated mice, whereas vaccination with the parental BCG did not. Moreover, mice vaccinated with the SapM::T mutant survived significantly longer than mice vaccinated with the parental BCG (Median Survival Time of SapM::T mutant is 32 weeks cfr 26.5 weeks in mice vaccinated with parental BCG $P=0.0145$) (FIG. 4, Panels B and C).

Of note, the Mb2196::T mutant was also tested in this setting and significantly longer survival was seen, with survival times between the ManLAM capping mutants and the SapM::T mutant (FIG. 4, Panel D). Vaccination with all BCG strains delayed the apparition of cachexia as compared to mice infected with TB alone. Whereas TB-infected mice started to show weight loss at about week 15 post-infection. BCG-vaccinated animals kept their initial body weight about ten weeks longer. Afterwards, cachexia also developed in BCG-vaccinated mice and, as for the survival, mice vaccinated with Mb1661c::T, 2196::T and SapM::T mutant showed the smallest reductions in mean body weight (FIG. 4, Panel E).

We subsequently checked if results could be confirmed when the infection occurred intratracheally instead of intravenously three months post-vaccination. The number of bacteria in spleen and lungs was determined four and eight weeks post-infection. We could clearly see that both parental and all four mutant BCG strains offered significant protection against *M. tuberculosis* as shown by ten- to 100-fold reduced numbers of bacteria in spleen and lungs as compared to unvaccinated TB-infected mice. Both in spleens and lungs, a significantly lower number of bacteria was found in mice vaccinated with the SapM::T mutant than in mice vaccinated with parental BCG at eight weeks post-infection (FIG. 4, Panels F and G).

Four weeks after vaccination, we also assessed T-cell immunity by comparing antigen-specific interferon (IFN)-γ production by lung cells and splenocytes (FIG. 6). Significant IFNγ production in response to recAg85A (Rv3804c) and the synthetic 20-mer peptide p11 (Ag85A99-118aa, dominant CD4 T cell epitope (Denis et al., 1998)) could be measured in both spleen and lung cell culture supernatants from BALB/c mice vaccinated with *M. bovis* BCG wild-type and the SapM locus mutant, demonstrating a clear Th1 response. Lung cells from mice vaccinated with *M. bovis* BCG SapM::T induced lower IFN-γ levels in response to p11 compared to lung cells from mice vaccinated with *M. bovis* BCG. No drastic differences could be observed between splenocytes from mice vaccinated with *M. bovis* BCG wild-type versus mutants. Unvaccinated mice produced only minimal amounts of IFNγ.

Effect of the Mutations on Uptake by Macrophages and Dendritic Cells

Since ManLAM capping and SapM were described to be implicated in uptake of mycobacteria (Briken et al., 2004; Torrelles et al., 2006) and/or blockade of phagosome-lysosome fusion (Vergne et al., 2005), we investigated if these pathways were indeed affected by the mutations under study, and could thus contribute to the observed improved protection. To study the effect of disruption of the SapM locus or deficiency in ManLAM capping on the efficiency of binding and phagocytosis of the mycobacteria, *M. bovis* BCG wild-type and mutants were FITC labeled and uptake by murine macrophages was analyzed by flow cytometry. The percentage of FITC-positive macrophages is an indication of how many macrophages have bound or taken up FITC-labeled mycobacteria. We could show that wild-type *M. bovis* BCG, SapM::T and capping mutants were taken up similarly by murine macrophages (~60-70% FITC-positive macrophages six hours post-infection; FIG. 7, Panel A). Confocal and electron microscopy analysis demonstrated that mycobacteria are taken up by the macrophages and not just cell surface attached (data not shown). By calculating mean FITC intensities, we also demonstrate that similar amounts of bacteria are taken up by the macrophages in all conditions tested (FIG. 7, Panel A). We conclude that neither disruption of the SapM locus nor ManLAM capping deficiency strongly affect the binding and uptake of the bacterium to macrophages.

Similarly, we analyzed the uptake of the parental *M. bovis* BCG and the SapM::T mutant by bone-marrow-derived dendritic cells (BM-DCs). We could show that wild-type *M. bovis* BCG and the SapM::T mutant were taken up similarly by murine DCs (~25% FITC-positive DCs 24 hours post-infection; FIG. 7, Panel B). Similar amounts of bacteria are taken up by the DCs in both conditions tested as shown by comparable mean FITC intensities, demonstrating that neither disruption of the SapM locus nor ManLAM capping deficiency strongly affect the uptake of the bacterium by dendritic cells.

Effect of the Mutations on Phagosome-Lysosome Fusion

Inhibition of phagosome-lysosome fusion in infected macrophages by ManLAM is considered a hallmark of mycobacterial virulence (Fratti et al., 2003; Hmama et al., 2004; Kang et al., 2005; Vergne et al., 2003). *M. tuberculosis* PI3P phosphatase was shown to be required for reduction of PI3P levels of phagosomes and inhibition of phagosome maturation containing live mycobacteria (Vergne et al., 2005). To find out if the *M. bovis* BCG mutants (SapM::T, Mb2203::T and Mb1661c::T) were affected in phagosome maturation in macrophages, we performed colocalization experiments. Therefore, macrophages were infected with FITC-labeled *M. bovis* BCG and subsequently labeled with Lysotracker Red. Colocalization of BCG-containing phagosomes and lysosomes was examined by confocal microscopy (FIG. 7, Panel C). No significant differences in colocalization of FITC-containing phagosomes with lysosomes could be seen between macrophages infected with the parental strain and mutants. These findings were confirmed by analyzing the survival of the Mb2203::T, Mb1661c::T and SapM::T mutants in macrophages. There was no significant difference in the survival and replication in Mf4/4 macrophages of *M. bovis* BCG mutants as compared to the wild-type over a time period of 48 hours post-infection (FIG. 7, Panel D). The improved protective efficacy of the mutant BCG strains does not correlate with altered uptake or survival within macrophages in vitro.

Oxidant Activity Following Infection with *M. bovis* BCG Wild-Type Versus Mutants The ability of mycobacteria to survive within the hostile environment of macrophages also depends upon their ability to scavenge reactive oxygen species (ROS). Recently, it was shown that immunogenicity of *M. bovis* BCG can be enhanced by reducing the activity and secretion of microbial antioxidants (Sadagopal et al., 2009). Therefore, we compared intracellular ROS production following infection of macrophages with *M. bovis* BCG wild-type versus mutants, by means of dihydro-dichloro-fluorescein diacetate (CM-H2DCFDA), a cell-permeant indicator for ROS that is non-fluorescent until removal of the acetate groups by intracellular esterases and oxidation occurs within the cell. We document an increase in ROS production over time post-infection (FIG. 8), but no significant differences are seen between *M. bovis* BCG wild-type and tested mutants.

Effect of the Mutations on the Induction of Autophagy in Macrophages and BM-DCs Following Infection with *M. bovis* BCG Recently, it was demonstrated that autophagy, a bulk protein and organelle degradation process essential for cell maintenance and viability, could enhance the efficacy of BCG as a vaccine by increasing antigen presentation in mouse dendritic cells (Jagannath et al., 2009). Microtubule-associated protein 1 light chain 3 (LC3), the mammalian homologue of yeast Atg8, is involved in autophagosome formation during autophagy. Tracking the conversion of LC3-I to LC3-II is indicative of autophagic activity. The amount of LC3-II correlates well with the number of autophagosomes. This characteristic conversion of LC3 was used to monitor autophagic activity following infection of macrophages and BM-DCs with *M. bovis* BCG wild-type versus mutants. We could not observe any difference in conversion to LC3-II in wild-type versus mutant BCG tested (data not shown), demonstrating that the improved vaccine efficacy cannot be attributed to a higher degree of autophagy induction in the antigen-presenting cells (APCs) tested.

Effect on Lymph Node DC Trafficking and Activation

Dendritic cells have the property to migrate from sites of antigen uptake to lymphoid organs, thereby initiating adaptive immune responses. A difference in trafficking to the lymph nodes and/or activation of DCs might have a major impact on the final immune outcome. In this context, we evaluated the effect of vaccination of mice with the parental *M. bovis* BCG versus the SapM locus mutant. Therefore, BALB/c mice were infected subcutaneously with $10^6$ CFU of the parental or the *M. bovis* BCG SapM mutant strain. Mice were sacrificed at day 1 and day 7 post-infection and the infiltration of DCs in the inguinal and brachial/axillary lymph nodes and their activation status was examined flow-cytometrically. At day 7 post-infection, a clear increase in the amount of CD11c+ DCs could be seen in the inguinal (FIG. 9, Panels A and B) and brachial/axillary lymph nodes (data not shown) from mice infected with the *M. bovis* BCG SapM mutant compared to the control and *M. bovis* BCG WT-infected mice. Already at day 1 post-infection, the amount of CD40+MHC-IIlo/med CD8α− DCs was raised in *M. bovis* BCG SapM-infected mice compared to the *M. bovis* BCG WT-infected mice, a difference that could also be observed seven days post-infection (FIG. 9, Panel C). The reduced MHC-II expression refers to the decreasing amount of resident DCs in the draining lymph nodes. Besides the increased recruitment of DCs to the draining lymph nodes upon vaccination with *M. bovis* BCG SapM, the DCs also demonstrate increased expression of CD80 and CD86, demonstrating improved activation (FIG. 9, Panel D). We can thus conclude that vaccination with the *M. bovis* SapM locus mutant augments recruitment of DCs to the lymph nodes and their activation, which can consequently lead to increased antigen presentation and T cell activation.

Effect of the Mutations on Bacterial Replication of *M. BOVIS* BCG in Infected Mice BALB/c mice were infected intravenously with *M. bovis* BCG and *M. bovis* BCG mutants (Mb2203::T, Mb1661c::T and SapM::T). The bacterial load in the lungs and spleen was determined at weeks 2, 4 and 12 post-infection. Two weeks after infection, slightly higher counts of the parental strain compared to the mutants could be measured in the lungs. Four weeks post-infection, the mutants reached similar numbers of CFU in the lungs and spleen as the wild-type *M. bovis* BCG cells (FIG. 10, Panels A and B). Overall, bacterial numbers in lung and spleen decreased over time, demonstrating clearance.

Effect of the Mutations on Cytokine Production and Granuloma Formation In Vivo

The uptake of *M. tb* by alveolar macrophages typically results in a local inflammatory response (van Crevel et al., 2002), mediated by the production of IL-12, IFNγ and TNF. This response finally leads to granuloma formation (Cooper et al., 1993; Dalton et al., 1993; Kamijo et al., 1993; Kindler et al., 1989). Progressive granuloma formation is a hallmark of chronic mycobacterial infection, which is associated by a partial shift to Th2-type immunity (Harris et al., 2008; Jiao et al., 2003; Orme et al., 1993; Rhodes et al., 2000). Therefore, we investigated the influence of an altered (Man)LAM structure or inactivation of the PI3P phosphatase SapM on the local inflammatory response in the lungs. C57BL/6 mice were intratracheally instilled with *M. bovis* BCG wild-type or mutants and IFNγ, TNF, IL-2, IL-4, IL-5, IL-6, IL-10 or ILS2 12p70 levels were quantified in the bronchioalveolar lavage (BAL) four weeks post-infection.

We could detect the production of IFN-γ and TNF, however, no or very low amounts of IL-2, IL-4, IL-5, IL-6, IL-10 or IL-12p70 could be measured. No significant differences could be observed in the elicited cytokine response in the lungs following infection with wild-type versus mutant BCG (FIG. 10, Panel C, Table 2).

Table 2: Cytokine measurements in BALF following infection of mice with *M. bovis* BCG wild-type versus mutants

TABLE 2

Cytokine measurements in BALF following infection of mice with *M. bovis* BCG wild type versus mutants

| Cytokine | PBS | wild type | 1661c | 2203 | SapM |
|---|---|---|---|---|---|
| | | | Average | | |
| IFNγ | 0.06 | 96.45 | 84.86 | 146.86 | 116.80 |
| TNF | 0.00 | 102.53 | 123.73 | 145.83 | 106.53 |
| IL-2 | 0.10 | 0.86 | 1.34 | 0.89 | 0.79 |
| IL-4 | 0.18 | 0.83 | 0.67 | 0.17 | 0.20 |
| IL-5 | 0.09 | 1.03 | 1.11 | 0.29 | 0.43 |
| IL-6 | 0.28 | 11.50 | 5.43 | 7.09 | 4.18 |
| IL-10 | 13.29 | 4.65 | 3.71 | 5.78 | 4.07 |
| IL-12p70 | 0.48 | 0.65 | 1.15 | 0.77 | 0.17 |
| | | | SEM | | |
| IFNγ | 0.03 | 22.10 | 21.00 | 47.34 | 28.17 |
| TNF | 0.00 | 33.43 | 32.97 | 46.01 | 26.34 |
| IL-2 | 0.05 | 0.38 | 0.45 | 0.30 | 0.29 |
| IL-4 | 0.13 | 0.48 | 0.37 | 0.08 | 0.14 |
| IL-5 | 0.09 | 0.55 | 0.43 | 0.15 | 0.31 |
| IL-6 | 0.19 | 2.85 | 1.78 | 2.35 | 0.83 |
| IL-10 | 2.34 | 2.18 | 1.21 | 1.33 | 1.26 |
| IL-12p70 | 0.25 | 0.28 | 0.63 | 0.35 | 0.17 |
| | | | Range | | |
| IFNγ | 0-0.29 | 32.35-180.58 | 8.79-194.68 | 2.44-454.73 | 58.40-291.09 |
| TNF | 0.00 | 0-270.97 | 31.33-306.61 | 11.04-434.85 | 33.59-246.74 |
| IL-2 | 0-0.38 | 0-2.93 | 0-4.01 | 0-2.51 | 0-2.38 |
| IL-4 | 0-1.08 | 0-3.76 | 0-3.12 | 0-0.66 | 0-1.16 |
| IL-5 | 0-0.73 | 0-4.17 | 0-3.49 | 0-1.34 | 0-2.5 |
| IL-6 | 0-1.51 | 0-21.98 | 1.62-17.27 | 0-21.26 | 1.12-7.49 |
| IL-10 | 5.76-27.03 | 0-19.32 | 0-8.72 | 0-13.43 | 0-8.84 |
| IL-12p70 | 0-1.69 | 0-1.72 | 0-5.03 | 0-2.79 | 0-1.36 |

We also examined the effect of the mutations on *M. bovis* BCG-induced protective granuloma formation. C57BL/6 mice were infected intravenously or were intratracheally instilled with *M. bovis* BCG wild-type versus mutants. Livers and lungs were removed three weeks and four weeks post-infection, respectively. Haematoxylin-Eosin stainings on paraffin sections of these organs allowed visualization and counting granulomas. Livers of mice that were infected with Mb1661c::T and Mb2203::T showed slightly lower numbers of granulomas compared to mice that were infected with *M. bovis* BCG wild-type and SapM::T (FIG. 10, Panel D). However, upon evaluation of the size of the granulomas, we observed that infection with these mutants appeared to induce the formation of slightly bigger granulomas compared to what happens in the livers of SapM::T or wild-type-infected mice (data not shown).

Cytokine Production Following Infection of BM-DCs with *M. bovis* BCG Wild-Type Versus SapM::T In view of the increased recruitment to, and activation of, DCs in the draining lymph nodes upon infection of mice with the SapM::T mutant, we analyzed cytokine production upon infection of BM-DCs in vitro. BM-DCs were infected with *M. bovis* BCG wild-type versus SapM::T for the indicated time points at which supernatant was taken to determine the levels of IL-1α, IL-1β, IL-2, IL-4, IL-6, IL-10, IL-12p40, IFNγ, TNFα. We could not detect significant levels of IL-2, IL-4, IL-10 nor IFNγ, however, we did see an increased production of IL-1β, IL-6, IL-12p40 and TNFα upon infection with *M. bovis* BCG SapM::T compared to wild-type (FIG. 11), demonstrating an augmented pro-inflammatory response.

Effect of the SapM::T Mutation on the Activation of iNKT Cells

The role of non-MHC-restricted T cells in TB is still not clearly delineated. γδ T cells are frequently activated by a variety of pathogens including *M. tb*. Mice lacking γδ T cells succumb more rapidly than control mice following intravenous challenge with virulent *M. tb*, whereas, this difference has not been observed when infection occurs via the aerosol route (D'Souza et al., 1997; Ladel et al., 1995). Although γδ T cells may not be required for optimum control of bacterial replication following pulmonary infection, γδ T cell-deficient mice form disorganized granulomas dominated by foamy macrophages and granulocytes instead of lymphocytes (D'Souza et al., 1997). Invariant (i) NKT cells recognize lipids presented by the antigen-presenting molecule CD1d. It has been shown that granuloma formation upon subcutaneous injection of deproteinized cell walls of *M. tb* in mice depends on iNKT cells (Apostolou et al., 1999). Specific activation of NKT cells by the CD1d ligand α-galactosylceramide (αGalCer) protects susceptible mice from *tuberculosis*. While it had been previously shown that CD1d−/− mice are not more susceptible to *tuberculosis*(Chackerian et al., 2002), Sada-Ovalle and colleagues demonstrated that CD1d-restricted iNKT cells play a physiological role in mediating protection against aerosol *M. tb* infection in vivo (Sada-Ovalle et al., 2008). The vast majority of diverse CD1d-restricted T cells do not recognize αGalCer, while, in contrast, both human and mouse iNKT cells recognize aGalCer presented by CD1d (Behar and Porcelli, 2007). Activation of NKT cells occurs before that of MHC-restricted T cells during infection with *M. bovis* BCG in mice.[10] We have investigated the role of iNKT cells upon infection with *M. bovis* BCG WT versus mutants by analyzing cytokine responses and cell surface marker expression following cocultures of *M. bovis* BCG-infected BM-derived DCs with iNKT hybridomas. Coculture with *M. bovis* BCG SapM::T infected DCs did induce similar expression levels of IL-2 and IL-12p40 compared to coculture with *M. bovis* BCG WT. In addition, we could not observe clear differences in cell surface marker expression (data not shown). This result is also in accordance with the findings that lipid and mycolic acid composition is similar for the parental *M. bovis* BCG and mutant strains (see Example 2) and that CD1d expression following infection of BM-DCs with the different strains is also comparable (data not shown).

Discussion

Proof is presented herein of the important concept that a single null mutation in *M. bovis* BCG can result in a vaccine with improved long-term survival during pulmonary *tuberculosis*. The use of such a mutant BCG strain is easy to implement and will face less safety and regulatory issues than either transgenic BCG or attenuated *M. tuberculosis*, for which similar, but not better, improvement in long-term survival of experimental animals has been reported and which are now in the first stages of clinical development (STOP-TB-Partnership, 2009). We hypothesized that mutation of mycobacterial components reportedly involved in phagosome maturation inhibition could yield better vaccines, since such mutations should result in better vaccine antigen processing and display. We, therefore, generated an ordered *M. bovis* BCG transposon insertion mutant library in which we identified and biochemically characterized mutants in two genes necessary for the alpha-1,2-oligomannosyl capping of cell wall ManLAM (Fratti et al., 2003; Hmama et al., 2004; Kang et al., 2005), a gene required for the addition of a linear α-1,6-mannose polymer of 21-34 residues to the PIM4 precursor in LM synthesis (ref 23) and the PI3P phosphatase SapM gene locus (Vergne et al., 2005), amongst others (see Example 2). ManLAM and SapM were both previously reported to have the potential of interfering with macrophage phagosome-lysosome fusion, a major *mycobacterium* clearance mechanism (Fratti et al., 2003; Hmama et al., 2004; Kang et al., 2005; Vergne et al., 2003; Vergne et al., 2005). We show that vaccination with both ManLAM capping mutants, the LM synthesis mutant and the SapM::T mutant resulted in significantly longer survival following *M. tb* infection as compared to non-vaccinated mice. In addition, the SapM::T mutant vaccinees survived significantly longer as compared to parental BCG vaccinees, comparable to other engineered live vaccines currently in clinical trials.

In vitro studies showed that the mutant BCG strains survived and replicated equally well as parental BCG in macrophages. In vivo bacterial replication analysis in infected immunocompetent mice did not show any difference between wild-type and mutants (FIG. 10, Panels A and B). Similarly, no significant differences could be observed in the elicited cytokine response in the lungs following infection with wild-type versus mutant BCG (FIG. 10, Panel C). (Note that although the results with the Mb2196::T mutant have not been duplicated yet, initial results are similar to those obtained with the other BCG mutants.)

However, there was a great variability in the levels of some cytokines, a problem that has been reported before (Appelmelk et al., 2008). We could also not detect huge differences in the amount of granulomas formed in livers and lungs post-infection. Livers of mice infected with Mb1661c::T and Mb2203::T showed slightly lower numbers of granulomas (FIG. 10, Panel D). However, upon evaluation of the size of the granulomas, we observed that infection with these mutants appeared to induce the formation of slightly bigger granulomas compared to what happens in the livers of SapM::T or wild-type-infected mice (data not shown). Importantly, all of these data show that these mutated BCG strains behave indistinguishably from parental wild-type BCG in immunocompetent mice, which confirms their expected safety. Moreover, these results demonstrate that neither SapM nor ManLAM capping play major roles in phagosome maturation arrest, in contrast to accepted dogmas, and probably do not explain the improved vaccine efficiency of the mutants. The reason for this discrepancy on the role of ManLAM and SapM in phagosome maturation is not clear. However, a serious problem with most of the studies previously described is that only purified ManLAM or ManLAM-coated beads were used to prove their point. The same is true for SapM, where its role in phagosome maturation was demonstrated by using purified SapM in a phagosome-late endosome in vitro fusion reaction (Vergne et al., 2005). By omitting the use of intact bacteria selectively deficient in ManLAM or SapM, it is by no means clear whether the potential activities of ManLAM and SapM identified in these studies have any relevance for the course of a mycobacterial infection. Appelmelk and colleagues began to address this important issue by studying the Rv1635c capping mutant of *M. bovis* BCG and *M. marinum* (Appelmelk et al., 2008). Indeed, they could show that these mutants were not affected in survival in phagocytes (Appelmelk et al., 2008), suggesting that ManLAM does not dominate the interaction between mycobacteria and the host, in contrast to what was long assumed. However, this mutation also inducesan approximately ten-fold lower LAM abundance in the cell wall (Dinadayala et al., 2006), which could lead to compensating alterations in the cell wall that mask the phenotype of LAM capping. To resolve this issue, we also made use of the Mb2203 mutant (or Rv2181 in *M. tb*), which is actually more selectively affecting the α-1,2-oligomannosyl cap structure synthesis than mutation of Rv1635c, and leaves LAM levels intact (Kaur et al., 2006; Kaur et al., 2008). Therefore, the Mb2203 mutant is more suitable to elucidate the role of α-1,2-oligomannosyl capping in mycobacterial uptake by macrophages and mycobacterial persistence following uptake.

We cannot fail to mention that the ability of *M. tb* to survive within the hostile environment of macrophages also depends on its property to scavenge reactive oxygen species. Oxidants have important signaling roles in the maturation of dendritic cells (Kantengwa et al., 2003), proliferation of T cells (van der Veen et al., 2004) and the activation and apoptosis of macrophages (Forman and Torres, 2001). The inactivation of host-generated oxidants by mycobacterial antioxidants may disrupt redox signaling during early infection and promote TB pathogenesis by weakening host immune responses and promoting tissue-damaging immunopathology. We analyzed if the improved protection against *M. tb* infection by the *M. bovis* SapM::T mutant could be due to a decreased production of oxidants. However, in all mutants tested, we could not detect any change in oxidant activity following infection of macrophages, also showing that this feature does not contribute to the higher efficacy of the *M. bovis* SapM::T vaccine. We can also exclude that the latter is due to an increased induction of autophagy upon infection of macrophages, since we did not observe differences in the conversion from LC3-I to LC3-II, indicative of autophagic activity, following infection with *M. bovis* BCG wild-type versus mutants.

However, we do clearly show that subcutaneous vaccination with *M. bovis* BCG SapM::T induces an increased recruitment of CD11c+ DCs to the draining lymph nodes compared to vaccination with the parental vaccine strain. Additionally, these DCs are also in an increased activation status, which can contribute to increased antigen presentation and immune responses, which seem to be pro-inflammatory (FIG. 11). A possible contribution of iNKT cells has been excluded in vitro (data not shown). Our observations are also of extreme importance in view of the recent model describing that the decrease in the effectiveness of the BCG vaccine against pulmonary *tuberculosis* is not a consequence of over-attenuation but could be because of increased immune suppression (Kernodle, 2010). If we look to the genome of the Tokyo 172 and Danish 1331 strain, we see that they contain the DU2 duplication unit, enclosing antioxidant genes and Mb3338 (SapM) (Brosch et al., 2007). This DU2 duplication does not, however, occur in the BCG Pasteur strain. The fact that the Tokyo 172 and Danish 1331 strain are less effective against pulmonary *tuberculosis* can thus be explained by the presence of multiple copies of antioxidant genes (Kernodle, 2010; Sadagopal et al., 2009) and SapM, which all seem to be immune evasion genes in BCG. It would thus be valuable to combine knockouts of antioxidant genes as described in Sadagopal et al. (2009) with a SapM knockout, as this is expected to further improve the vaccine potency. The implementation of these mutations through standard clean, resistance marker-free gene disruption for clinical trials is important and ongoing.

REFERENCES

Numeric References

1. Bardarov S., J. Kriakov, C. Carriere, S. Yu, C. Vaamonde, R. A. McAdam, B. R. Bloom, G. F. Hatfull, and W.R. Jacobs, Jr. (1997). Conditionally replicating mycobacteriophages: a system for transposon delivery to *Mycobacterium tuberculosis. Proc. Natl. Acad. Sci. U.S.A.* 94:10961-6.
2. Behr M. A., M. A. Wilson, W. P. Gill, H. Salamon, G. K. Schoolnik, S. Rane, and P. M. Small (1999). Comparative genomics of BCG vaccines by whole-genome DNA microarray. *Science* 284:1520-3 (New York, N.Y.).
3. Beresford N. J., D. Mulhearn, B. Szczepankiewicz, G. Liu, M. E. Johnson, A. Fordham-Skelton, C. Abad-Zapatero, J. S. Cavet, and L. Tabernero (2009). Inhibition of MptpB phosphatase from *Mycobacterium tuberculosis* impairs mycobacterial survival in macrophages. *J. Antimicrob. Chemother.* 63:928-36.
4. Berg S., J. Starbuck, J. B. Torrelles, V. D. Vissa, D. C. Crick, D. Chatterjee, and P. J. Brennan (2005). Roles of conserved proline and glycosyltransferase motifs of EmbC in biosynthesis of lipoarabinomannan. *J. Biol. Chem.* 280:5651-63.
5. Brennan P. J. (2003). Structure, function, and biogenesis of the cell wall of *Mycobacterium tuberculosis. Tuberculosis* 83:91-7 (Edinburgh, Scotland).
6. Briken V., S. A. Porcelli, G. S. Besra, and L. Kremer (2004). Mycobacterial lipoarabinomannan and related lipoglycans: from biogenesis to modulation of the immune response. *Mol. Microbiol.* 53:391-403.
7. Briken V., S. A. Porcelli, G. S. Besra, and L. Kremer (2004). Mycobacterial lipoarabinomannan and related lipoglycans: from biogenesis to modulation of the immune response. *Mol. Microbiol.* 53:391-403.
8. Brosch R., S. V. Gordon, T. Garnier, K. Eiglmeier, W. Frigui, P. Valenti, S. Dos Santos, S. Duthoy, C. Lacroix, C. Garcia-Pelayo, J. K. Inwald, P. Golby, J. N. Garcia, R. G. Hewinson, M. A. Behr, M. A. Quail, C. Churcher, B. G. Barrell, J. Parkhill, and S. T. Cole (2007). Genome plasticity of BCG and impact on vaccine efficacy. *Proc. Natl. Acad. Sci. U.S.A.* 104:5596-601.
9. Castandet J., J. F. Prost, P. Peyron, C. Astarie-Dequeker, E. Anes, A. J. Cozzone, G. Griffiths, and I. Maridonneau-Parini (2005). Tyrosine phosphatase MptpA of *Mycobacterium tuberculosis* inhibits phagocytosis and increases actin polymerization in macrophages. *Res. Microbiol.* 156:1005-13.
10. Cavaignac S. M., S. J. White, G. W. de Lisle, and D. M. Collins (2000). Construction and screening of *Mycobacterium paratuberculosis* insertional mutant libraries. *Archives of Microbiology* 173:229-31.
11. Dinadayala P., D. Kaur, S. Berg, A. G. Amin, V. D. Vissa, D. Chatterjee, P. J. Brennan, and D. C. Crick (2006). Genetic basis for the synthesis of the immunomodulatory mannose caps of lipoarabinomannan in *Mycobacterium tuberculosis. J. Biol. Chem.* 281:20027-35.
12. Dinadayala P., D. Kaur, S. Berg, A. G. Amin, V. D. Vissa, D. Chatterjee, P. J. Brennan, and D. C. Crick (2006). Genetic basis for the synthesis of the immunomodulatory mannose caps of lipoarabinomannan in *Mycobacterium tuberculosis. J. Biol. Chem.* 281:20027-35.

13. Ehrt S., and D. Schnappinger (2009). Mycobacterial survival strategies in the phagosome: defense against host stresses. *Cell Microbiol.* 11:1170-8.

14. Flannagan R. S., G. Cosio, and S. Grinstein (2009). Antimicrobial mechanisms of phagocytes and bacterial evasion strategies. *Nat. Rev. Microbiol.* 7:355-66.

15. Fratti R. A., J. Chua, I. Vergne, and V. Deretic (2003). *Mycobacterium tuberculosis* glycosylated phosphatidylinositol causes phagosome maturation arrest. *Proc. Natl. Acad. Sci. U.S.A.* 100:5437-42.

16. Garnier T., K. Eiglmeier, J. C. Camus, N. Medina, H. Mansoor, M. Pryor, S. Duthoy, S. Grondin, C. Lacroix, C. Monsempe, S. Simon, B. Harris, R. Atkin, J. Doggett, R. Mayes, L. Keating, P. R. Wheeler, J. Parkhill, B. G. Barrell, S. T. Cole, S. V. Gordon, and R. G. Hewinson (2003). The complete genome sequence of 100:7877-82.

17. Gordon S. V., D. Bottai, R. Simeone, T. P. Stinear, and R. Brosch (2009). Pathogenicity in the tubercle *bacillus*: molecular and evolutionary determinants. *Bioessays* 31:378-88.

18. Guenin-Mace L., R. Simeone, and C. Demangel (2009). Lipids of pathogenic Mycobacteria: contributions to virulence and host immune suppression. *Transboundary and Emerging Diseases* 56:255-68.

19. Gurcha S. S., A. R. Baulard, L. Kremer, C. Locht, D. B. Moody, W. Muhlecker, C. E. Costello, D. C. Crick, P. J. Brennan, and G. S. Besra (2002). Ppm1, a novel polyprenol monophosphomannose synthase from *Mycobacterium tuberculosis. The Biochemical Journal* 365:441-50.

20. Kaur D., S. Berg, P. Dinadayala, B. Gicquel, D. Chatterjee, M. R. McNeil, V. D. Vissa, D. C. Crick, M. Jackson, and P. J. Brennan (2006). Biosynthesis of mycobacterial lipoarabinomannan: role of a branching mannosyltransferase. Proc. Natl. Acad. Sci. U.S.A. 103:13664-9.

21. Kaur D., S. Berg, P. Dinadayala, B. Gicquel, D. Chatterjee, M. R. McNeil, V. D. Vissa, D. C. Crick, M. Jackson, and P. J. Brennan (2006). Biosynthesis of mycobacterial lipoarabinomannan: role of a branching mannosyltransferase. *Proc. Natl. Acad. Sci. U.S.A.* 103:13664-9.

22. Kaur D., T. L. Lowary, V. D. Vissa, D. C. Crick, and P. J. Brennan (2002). Characterization of the epitope of anti-lipoarabinomannan antibodies as the terminal hexaarabinofuranosyl motif of mycobacterial arabinans. *Microbiology* 148:3049-57 (Reading, England).

23. Kaur D., M. R. McNeil, K. H. Khoo, D. Chatterjee, D. C. Crick, M. Jackson, and P. J. Brennan (2007). New insights into the biosynthesis of mycobacterial lipomannan arising from deletion of a conserved gene. J. Biol. Chem. 282: 27133-40.

24. Kaur D., A. Obregon-Henao, H. Pham, D. Chatterjee, P. J. Brennan, and M. Jackson (2008). Lipoarabinomannan of *Mycobacterium*: mannose capping by a multifunctional terminal mannosyltransferase. *Proc. Natl. Acad. Sci.* 105: 17973-7.

25. Kordulakova J., M. Gilleron, K. Mikusova, G. Puzo, P. J. Brennan, B. Gicquel, and M. Jackson (2002). Definition of the first mannosylation step in phosphatidylinositol mannoside synthesis. PimA is essential for growth of mycobacteria. *J. Biol. Chem.* 277:31335-44.

26. Kremer L., S. S. Gurcha, P. Bifani, P. G. Hitchen, A. Baulard, H. R. Morris, A. Dell, P. J. Brennan, and G. S. Besra (2002). Characterization of a putative alphamannosyltransferase involved in phosphatidylinositol trimannoside biosynthesis in *Mycobacterium tuberculosis. Biochem. J.* 363:437-47.

27. Lamichhane G., M. Zignol, N. J. Blades, D. E. Geiman, A. Dougherty, J. Grosset, K. W. Broman, and W. R. Bishai (2003). A post-genomic method for predicting essential genes at subsaturation levels of mutagenesis: application to *Mycobacterium tuberculosis. Proc. Natl. Acad. Sci. U.S.A.* 100:7213-8.

28. Lampe D. J., M. E. Churchill, and H. M. Robertson (1996). A purified mariner transposase is sufficient to mediate transposition in vitro. *EMBO J.* 15:5470-9.

29. Lane J. M., and E. J. Rubin (2006). Scaling down: a PCR-based method to efficiently screen for desired knockouts in a high density *Mycobacterium tuberculosis*-picked mutant library. *Tuberculosis* 86:310-3 (Edinburg, Scotland).

30. Laroy W., R. Contreras, and N. Callewaert (2006). Glycome mapping on DNA sequencing equipment. *Nat. Protoc.* 1:397-405.

31. Laroy W., R. Contreras, and N. Callewaert (2006). Glycome mapping on DNA sequencing equipment. *Nat. Protoc.* 1:397-405.

32. Machowski E. E., R. A. McAdam, K. M. Derbyshire, and V. Mizrahi (2000). Construction and application of mycobacterial reporter transposons. *Gene* 253:67-75.

33. Mahairas G. G., P. J. Sabo, M. J. Hickey, D. C. Singh, and C. K. Stover (1996). Molecular analysis of genetic differences between *Mycobacterium bovis* BCG and virulent *M. bovis*. Journal of bacteriology 178:1274-82.

34. Maras M., N. Callewaert, K. Piens, M. Claeyssens, W. Martinet, S. Dewaele, H. Contreras, I. Dewerte, M. Penttila, and R. Contreras (2000). Molecular cloning and enzymatic characterization of a *Trichoderma reesei* 1,2-alpha-D-mannosidase. *J. Biotech.* 77:255-63.

35. Master S. S., S. K. Rampini, A. S. Davis, C. Keller, S. Ehlers, B. Springer, G. S. Timmins, P. Sander, and V. Deretic (2008). *Mycobacterium tuberculosis* prevents inflammasome activation. *Cell Host Microbe* 3:224-32.

36. Master S. S., S. K. Rampini, A. S. Davis, C. Keller, S. Ehlers, B. Springer, G. S. Timmins, P. Sander, and V. Deretic (2008). *Mycobacterium tuberculosis* prevents inflammasome activation. *Cell Host Microbe* 3:224-32.

37. McAdam R. A., S. Quan, D. A. Smith, S. Bardarov, J. C. Betts, F. C. Cook, E. U. Hooker, A. P. Lewis, P. Woollard, M. J. Everett, P. T. Lukey, G. J. Bancroft, W. R. Jacobs Jr., and K. Duncan (2002). Characterization of a *Mycobacterium tuberculosis* H37Rv transposon library reveals insertions in 351 ORFs and mutants with altered virulence. *Microbiology* 148:2975-86 (Reading, England).

38. McCarthy T. R., J. B. Torrelles, A. S. MacFarlane, M. Katawczik, B. Kutzbach, L. E. Desjardin, S. Clegg, J. B. Goldberg, and L. S. Schlesinger (2005). Overexpression of *Mycobacterium tuberculosis* manB, a phosphomannomutase that increases phosphatidylinositol mannoside biosynthesis in *Mycobacterium smegmatis* and mycobacterial association with human macrophages. *Molecular Microbiology* 58:774-90.

39. McFadden J. (1996). Recombination in mycobacteria. *Molecular Microbiology* 21:205-11.

40. Minnikin D. E., L. Kremer, L. G. Dover, and G. S. Besra (2002). The methylbranched fortifications of *Mycobacterium tuberculosis. Chem. Biol.* 9:545-53.

41. Monsarrat B., T. Brando, P. Condouret, J. Nigou, and G. Puzo (1999). Characterization of mannooligosaccharide caps in mycobacterial lipoarabinomannan by capillary electrophoresis/electrospray mass spectrometry. *Glycobiology* 9:335-42.

42. Mueller P., and J. Pieters (2006). Modulation of macrophage antimicrobial mechanisms by pathogenic mycobacteria. *Immunobiology* 211:549-56.

43. Murry J. P., C. M. Sassetti, J. M. Lane, Z. Xie, and E. J. Rubin (2008). Transposon site hybridization in *Mycobacterium tuberculosis. Methods in Molecular Biology* 416: 45-59 (Clifton, N.J.).

44. Ortalo-Magne A., M. A. Dupont, A. Lemassu, A. B. Andersen, P. Gounon, and M. Daffe (1995). Molecular composition of the outermost capsular material of the tubercle *bacillus. Microbiology* 141 (Pt 7):1609-20 (Reading, England).

45. Owens R. M., F. F. Hsu, B. C. VanderVen, G. E. Purdy, E. Hesteande, P. Giannakas, J. C. Sacchettini, J. D. McKinney, P. J. Hill, J. T. Belisle, B. A. Butcher, K. Pethe, and D. G. Russell (2006). *M. tuberculosis* Rv2252 encodes a diacylglycerol kinase involved in the biosynthesis of phosphatidylinositol mannosides (PIMs). *Mol. Microbiol.* 60:1152-63.

46. Packer N. H., M. A. Lawson, D. R. Jardine, and J. W. Redmond (1998). A general approach to desalting oligosaccharides released from glycoproteins. *Glycoconjugate Journal* 15:737-47.

47. Parish T., and N. G. Stoker (1999). *Mycobacteria*: bugs and bugbears (two steps forward and one step back). *Molecular Biotechnology* 13:191-200.

48. Prinzis S., D. Chatterjee, and P. J. Brennan (1993). Structure and antigenicity of lipoarabinomannan from *Mycobacterium bovus* BCG. *Journal of General Microbiology* 139:2649-58.

49. Rubin E. J., B. J. Akerley, V. N. Novik, D. J. Lampe, R. N. Husson, and J. J. Mekalanos (1999). In vivo transposition of mariner-based elements in enteric bacteria and mycobacteria. *Proc. Natl. Acad. Sci. U.S.A.* 96:1645-50.

50. Russell D. G. (2001). *Mycobacterium tuberculosis*: here today, and here tomorrow. *Nature Reviews* 2:569-77.

51. Rybniker J., M. Wolke, C. Haefs, and G. Plum (2003). Transposition of Tn5367 in *Mycobacterium marinum*, using a conditionally recombinant mycobacteriophage. *Journal of Bacteriology* 185:1745-8.

52. Saleh M. T., and J. T. Belisle (2000). Secretion of an acid phosphatase (SapM) by *Mycobacterium tuberculosis* that is similar to eukaryotic acid phosphatases. *J. Bacteriol.* 182:6850-3.

53. Sander P., M. Rezwan, B. Walker, S. K. Rampini, R. M. Kroppenstedt, S. Ehlers, C. Keller, J. R. Keeble, M. Hagemeier, M. J. Colston, B. Springer, and E. C. Bottger (2004). Lipoprotein processing is required for virulence of *Mycobacterium tuberculosis. Molecular Microbiology* 52:1543-52.

54. Sassetti C. M., D. H. Boyd, and E. J. Rubin (2001). Comprehensive identification of conditionally essential genes in mycobacteria. *Proc. Natl. Acad. Sci. U.S.A.* 98:12712-7.

55. Sassetti C. M., D. H. Boyd, and E. J. Rubin (2003). Genes required for mycobacterial growth defined by high density mutagenesis. *Mol. Microbiol.* 48:77-84.

56. Sassetti C. M., D. H. Boyd, and E. J. Rubin (2003). Genes required for mycobacterial growth defined by high density mutagenesis. *Molecular Microbiology* 48:77-84.

57. Schaeffer M. L., K. H. Khoo, G. S. Besra, D. Chatterjee, P. J. Brennan, J. T. Belisle, and J. M. Inamine (1999). The pimB gene of *Mycobacterium tuberculosis* encodes a mannosyltransferase involved in lipoarabinomannan biosynthesis. *J. Biol. Chem.* 274:31625-31.

58. Schlesinger L. S., T. M. Kaufman, S. Iyer, S. R. Hull, and L. K. Marchiando (1996). Differences in mannose receptor-mediated uptake of lipoarabinomannan from virulent and attenuated strains of *Mycobacterium tuberculosis* by human macrophages. *J. Immunol.* 157:4568-75 (Baltimore Md.).

59. Sharma K., M. Gupta, M. Pathak, N. Gupta, A. Koul, S. Sarangi, R. Baweja, and Y. Singh (2006). Transcriptional control of the mycobacterial embCAB operon by PknH through a regulatory protein, EmbR, in vivo. *J. Bacteria* 188:2936-44.

60. Shenoy S. R., L. G. Barrientos, D. M. Ratner, B. R. O'Keefe, P. H. Seeberger, A. M. Gronenborn, and M. R. Boyd (2002). Multisite and multivalent binding between cyanovirin-N and branched oligomannosides: calorimetric and NMR characterization. *Chem. & Biol.* 9:1109-18.

61. Tan T., W. L. Lee, D. C. Alexander, S. Grinstein, and J. Liu (2006). The ESAT-6/CFP-10 secretion system of *Mycobacterium marinum* modulates phagosome maturation. *Cellular Microbiology* 8:1417-29.

62. Venisse A., J. M. Berjeaud, P. Chaurand, M. Gilleron, and G. Puzo (1993). Structural features of lipoarabinomannan from *Mycobacterium bovis* BCG. Determination of molecular mass by laser desorption mass spectrometry. *J. Biol. Chem.* 268:12401-11.

63. Vergne I., J. Chua, and V. Deretic (2003). *Tuberculosis* toxin blocking phagosome maturation inhibits a novel Ca2+/calmodulin-PI3K hVPS34 cascade. *J. Exp. Med.* 198:653-9.

64. Vergne I., J. Chua, H. H. Lee, M. Lucas, J. Belisle, and V. Deretic (2005). Mechanism of phagolysosome biogenesis block by viable *Mycobacterium tuberculosis. Proc. Natl. Acad. Sci. U.S.A.* 102:4033-8.

65. Zhang N., J. B. Torrelles, M. R. McNeil, V. E. Escuyer, K. H. Khoo, P. J. Brennan, and D. Chatterjee (2003). The Emb proteins of mycobacteria direct arabinosylation of lipoarabinomannan and arabinogalactan via an N-terminal recognition region and a C-terminal synthetic region. *Mol. Microbiol.* 50:69-76.

Alphabetic References

Abramoff M. D., P. J. Magelhaes, and S. J. Ram (2004). Image processing with ImageJ. *Biophotonics International* 11(7):36-42.

Apostolou I., Y. Takahama, C. Belmant, T. Kawano, M. Huerre, G. Marchal, J. Cui, M. Taniguchi, H. Nakauchi, J. J. Fournie, P. Kourilsky, and G. Gachelin (1999). Murine natural killer T(NKT) cells (correction of natural killer cells) contribute to the granulomatous reaction caused by mycobacterial cell walls. *Proc. Natl. Acad. Sci. U.S.A.* 96(9):5141-5146.

Appelmelk B. J., J. den Dunnen, N,N. Driessen, R. Ummels, M. Pak, J. Nigou, G. Larrouy-Maumus, S. S. Gurcha, F. Movahedzadeh, J. Geurtsen, E. J. Brown, M. M. Eysink Smeets, G. S. Besra, P. T. Willemsen, T. L. Lowary, Y. van Kooyk, J. J. Maaskant, N. G. Stoker, P. van der Ley, G. Puzo, C. M. Vandenbroucke-Grauls, C. W. Wieland, T. van der Poll, T. B. Geijtenbeek, A. M. van der Sar, and W. Bitter (2008). The mannose cap of mycobacterial lipoarabinomannan does not dominate the *Mycobacterium*-host interaction. *Cell Microbiol.* 10(4):930-944.

Barker L. F., M. J. Brennan, P. K. Rosenstein, and J. C. Sadoff (2009). *Tuberculosis* vaccine research: the impact of immunology. *Curr. Opin. Immunol.* 21(3):331-338.

Bastos R. G., S. Borsuk, F. K. Seixas, and O. A. Dellagostin (2009). Recombinant *Mycobacterium bovis* BCG. *Vaccine* 27(47);6495-503.

Behar S. M., and S. A. Porcelli (2007). CD1-restricted T cells in host defense to infectious diseases. *Curr. Top. Microbiol. Immunol.* 314:215-250.

Bolte S., and F. P. Cordelières (2006). A guided tour into subcellular colocalization analysis in light microscopy. *J. Microsc.* 224(3):213-232.

Briken V., S. A. Porcelli, G. S. Besra, and L. Kremer (2004). Mycobacterial lipoarabinomannan and related lipoglycans: from biogenesis to modulation of the immune response. *Mol. Microbiol.* 53(2):391-403.

Brosch R., S. V. Gordon, T. Garnier, K. Eiglmeier, W. Frigui, P. Valenti, S. Dos Santos, S. Duthoy, C. Lacroix, C. Garcia-Pelayo, J. K. Inwald, P. Golby, J. N. Garcia, R. G. Hewinson, M. A. Behr, M. A. Quail, C. Churcher, B. G. Barrell, J. Parkhill, and S. T. Cole (2007). Genome plasticity of BCG and impact on vaccine efficacy. *Proc. Natl. Acad. Sci. U.S.A.* 104(13):5596-5601.

Brossay L., O, Naidenko, N. Burdin, J. Matsuda, T. Sakai, and M. Kronenberg (1998a). Structural requirements for galactosylceramide recognition by CD1-restricted NK T cells. *J. Immunol.* 161(10):5124-5128.

Brossay L., S. Tangri, M. Bix, S. Cardell, R. Locksley, and M. Kronenberg (1998b). Mouse CD1-autoreactive T cells have diverse patterns of reactivity to CD 1+ targets. *J. Immunol.* 160 (8):3681-3688.

Castanon-Arreola M., Y. Lopez-Vidal, C. Espitia-Pinzon, and R. Hernandez-Pando (2005). A new vaccine against *tuberculosis* shows greater protection in a mouse model with progressive pulmonary *tuberculosis. Tuberculosis* (*Edinb.*) 85(1-2):115-126.

Chackerian A., J. Alt, V. Perera, and S. M. Behar (2002). Activation of NKT cells protects mice from *tuberculosis. Infect. Immun.* 70(11):6302-6309.

Colditz G. A., T. F. Brewer, C. S. Berkey, M. E. Wilson, E. Burdick, H. V. Fineberg, and F. Mosteller (1994). Efficacy of BCG vaccine in the prevention of *tuberculosis*. Meta-analysis of the published literature. *Jama.* 271(9):698-702.

Cooper A. M., D. K. Dalton, T. A. Stewart, J. P. Griffin, D. G. Russell, I. M. Orme (1993). Disseminated *tuberculosis* in interferon gamma gene-disrupted mice. *J. Exp. Med.* 178 (6):2243-2247.

Copenhaver R. H., E. Sepulveda, L. Y. Armitige, J. K. Actor, A. Wanger, S. J. Norris, R. L. Hunter, and C. Jagannath (2004). A mutant of *Mycobacterium tuberculosis* H37Rv that lacks expression of antigen 85A is attenuated in mice but retains vaccinogenic potential. *Infect. Immun.* 72(12):7084-7095.

D'Souza C. D., A. M. Cooper, A. A. Frank, R. J. Mazzaccaro, B. R. Bloom, and I. M. Orme (1997). An anti-inflammatory role for gamma delta T lymphocytes in acquired immunity to *Mycobacterium tuberculosis. J. Immunol.* 158(3):1217-1221.

Dalton D. K., S. Pitts-Meek, S. Keshav, I. S. Figari, A. Bradley, and T. A. Stewart (1993). Multiple defects of immune cell function in mice with disrupted interferon-gamma genes. *Science* 259(5102):1739-1742.

Denis O., A. Tanghe, K. Palfliet, F. Jurion, T. P. van den Berg, A. Vanonckelen, J. Ooms, E. Saman, J. B. Ulmer, J. Content, and K. Huygen (1998). Vaccination with plasmid DNA encoding mycobacterial antigen 85A stimulates a CD4+ and CD8+ T-cell epitopic repertoire broader than that stimulated by *Mycobacterium tuberculosis* H37Rv infection. *Infect. Immun.* 66(4):1527-1533.

Dennehy M., and A. L. Williamson (2005). Factors influencing the immune response to foreign antigen expressed in recombinant BCG vaccines. *Vaccine* 23(10):1209-24.

Desmedt M., P. Rottiers, H. Dooms, W. Fiers, and J. Grooten (1998). Macrophages induce cellular immunity by activating Th1 cell responses and suppressing Th2 cell responses. *J. Immunol.* 160(11):5300-5308.

Dinadayala P., D. Kaur, S. Berg, A. G. Amin, V. D. Vissa, D. Chatterjee, P. J. Brennan, and D. C. Crick (2006). Genetic basis for the synthesis of the immunomodulatory mannose caps of lipoarabinomannan in *Mycobacterium tuberculosis. J. Biol. Chem.* 281(29):20027-20035.

Forman H. J., and M. Torres (2001). Signaling by the respiratory burst in macrophages. IUBMB Life 51(6):365-371.

Fratti R. A., J. Chua, I. Vergne, and V. Deretic (2003). *Mycobacterium tuberculosis* glycosylated phosphatidylinositol causes phagosome maturation arrest. *Proc. Natl. Acad. Sci. U.S.A.* 100(9):5437-5442.

Grode L., P. Seiler, S. Baumann, J. Hess, V. Brinkmann, A. Nasser Eddine, P. Mann, C. Goosmann, S. Bandermann, D. Smith, G. J. Bancroft, J. M. Reyrat, D. van Soolingen, B. Raupach, and S. H. Kaufmann (2005). Increased vaccine efficacy against *tuberculosis* of recombinant *Mycobacterium bovis* bacille Calmette-Guerin mutants that secrete listeriolysin. *J. Clin. Invest.* 115(9):2472-2479.

Gutierrez M. G., S. S. Master, S. B. Singh, G. A. Taylor, M. I. Colombo, V. Deretic (2004). Autophagy is a defense mechanism inhibiting BCG and *Mycobacterium tuberculosis* survival in infected macrophages. *Cell* 119(6):753-766.

Harris J., S. S. Master, S. A. De Haro, M. Delgado, E. A. Roberts, J.C. Hope, J. Keane, and V. Deretic (2008). Th1-Th2 polarization and autophagy in the control of intracellular mycobacteria by macrophages. *Vet. Immunol. Immunopathol.*

Hinchey J., S. Lee, B. Y. Jeon, R. J. Basaraba, M. M. Venkataswamy, B. Chen, J. Chan, M. Braunstein, I. M. Orme, S. C. Derrick, S. L. Morris, W. R. Jacobs, Jr., and S. A. Porcelli (2007). Enhanced priming of adaptive immunity by a proapoptotic mutant of *Mycobacterium tuberculosis. J. Clin. Invest.* 117(8):2279-2288.

Hmama Z., K. Sendide, A. Talal, R. Garcia, K. Dobos, and N. E. Reiner (2004). Quantitative analysis of phagolysosome fusion in intact cells: inhibition by mycobacterial lipoarabinomannan and rescue by an 1alpha,25-dihydroxyvitamin D3-phosphoinositide 3-kinase pathway. *J. Cell. Sci.* 117(Pt 10):2131-2140.

Horwitz M. A., and G. Harth (2003). A new vaccine against *tuberculosis* affords greater survival after challenge than the current vaccine in the guinea pig model of pulmonary *tuberculosis. Infect. Immun.* 71(4):1672-1679.

Horwitz M. A. (2005). Recombinant BCG expressing *Mycobacterium tuberculosis* major extracellular proteins. *Microbes Infect.* 7(5-6):947-54.

Jagannath C., D. R. Lindsey, S. Dhandayuthapani, Y. Xu, R. L. Hunter, Jr., and N. T. Eissa (2009). Autophagy enhances the efficacy of BCG vaccine by increasing peptide presentation in mouse dendritic cells. *Nat. Med.* 15(3):267-276.

Jiao X., R. Lo-Man, N. Winter, E. Deriaud, B. Gicquel, and C. Leclerc (2003). The shift of Th1 to Th2 immunodominance associated with the chronicity of *Mycobacterium bovis* bacille Calmette-Guerin infection does not affect the memory response. *J. Immunol.* 170(3):1392-1398.

Kamath A. T., U. Fruth, M. J. Brennan, R. Dobbelaer, P. Hubrechts, M. M. Ho, R. E. Mayner, J. Thole, K. B. Walker, M. Liu, and P. H. Lambert (2005). New live mycobacterial vaccines: the Geneva consensus on essential steps towards clinical development. *Vaccine* 23(29):3753-3761.

Kamijo R., J. Le, D. Shapiro, E. A. Havell, S. Huang, M. Aguet, M. Bosland, and J. Vilcek (1993). Mice that lack the interferon-gamma receptor have profoundly altered responses to infection with *Bacillus* Calmette-Guerin and subsequent challenge with lipopolysaccharide. *J. Exp. Med.* 178(4):1435-1440.

Kang P. B., A. K. Azad, J. B. Torrelles, T. M. Kaufman, A. Beharka, E. Tibesar, L. E. DesJardin, and L. S. Schlesinger (2005). The human macrophage mannose receptor directs *Mycobacterium tuberculosis* lipoarabinomannan-mediated phagosome biogenesis. *J. Exp. Med.* 202(7):987-999.

Kantengwa S., L. Jornot, C. Devenoges, and L. P. Nicod (2003). Superoxide anions induce the maturation of human dendritic cells. *Am. J. Respir. Crit. Care Med.* 167(3):31-437.

Kaur D., S. Berg, P. Dinadayala, B. Gicquel, D. Chatterjee, M. R. McNeil, V. D. Vissa, D. C. Crick, M. Jackson, and P. J. Brennan (2006). Biosynthesis of mycobacterial lipoarabinomannan: role of a branching mannosyltransferase. *Proc. Natl. Acad. Sci. U S. A.* 103(37):13664-13669.

Kaur D., A. Obregon-Henao, H. Pham, D. Chatterjee, P. J. Brennan, and M. Jackson (2008). Lipoarabinomannan of *Mycobacterium*: mannose capping by a multifunctional terminal mannosyltransferase. *Proc. Natl. Acad. Sci. U.S.A.* 105(46):17973-17977.

Kernodle D. S. (2010). Decrease in the effectiveness of Bacille Calmette-Guerin vaccine against pulmonary *tuberculosis*: a consequence of increased immune suppression by microbial antioxidants, not overattenuation. *Clin. Infect. Dis.* 51(2):177-184.

Kindler V., A. P. Sappino, G. E. Grau, P. F. Piguet, and P. Vassalli (1989). The inducing role of tumor necrosis factor in the development of bactericidal granulomas during BCG infection. *Cell* 56(5):731-740.

Krzywinska E., J. Krzywinski, and J. S. Schorey (2004). Naturally occurring horizontal gene transfer and homologous recombination in *Mycobacterium. Microbiology* 150 (Pt. 6):1707-1712.

Ladel C. H., C. Blum, A. Dreher, K. Reifenberg, and S. H. Kaufmann (1995). Protective role of gamma/delta T cells and alpha/beta T cells in *tuberculosis. Eur. J. Immunol.* 25(10):2877-2881.

Luo Y., H. Yamada, X. Chen, A. A. Ryan, D. P. Evanoff, J. A. Triccas, and M. A. O'Donnell (2004). Recombinant *Mycobacterium bovis* bacillus Calmette-Guérin (BCG) expressing mouse IL-18 augments Th1 immunity and macrophage cytotoxicity. *Clin. Exp. Immunol.* 137(1):24-34.

Martin C., A. Williams, R. Hernandez-Pando, P. J. Cardona, E. Gormley, Y. Bordat, C. Y. Soto, S. O. Clark, G. J. Hatch, D. Aguilar, V. Ausina, and B. Gicquel (2006). The live *Mycobacterium tuberculosis* phoP mutant strain is more attenuated than BCG and confers protective immunity against *tuberculosis* in mice and guinea pigs. *Vaccine* 24(17):3408-3419.

Master S. S., S. K. Rampini, A. S. Davis, C. Keller, S. Ehlers, B. Springer, G. S. Timmins, P. Sander, and V. Deretic (2008). *Mycobacterium tuberculosis* prevents inflammasome activation. *Cell Host Microbe* 3(4):224-232.

Orme I. M., A. D. Roberts, J. P. Griffin, and J. S. Abrams (1993). Cytokine secretion by CD4 T lymphocytes acquired in response to *Mycobacterium tuberculosis* infection. *J. Immunol.* 151(1):518-525.

Pym A. S., P. Brodin, L. Majlessi, R. Brosch, C. Demangel, A. Williams, K. E. Griffiths, G. Marchal, C. Leclerc, and S. T. Cole (2003). Recombinant BCG exporting ESAT-6 confers enhanced protection against *tuberculosis. Nat. Med.* 9(5): 533-539.

Rasband W. S., and J. Image (2008). Vol. t: U.S. National Institutes of Health, Bethesda, Md., USA.

Rhodes S. G., N. Palmer, S. P. Graham, A. E. Bianco, R. G. Hewinson, and H. M. Vordermeier (2000). Distinct response kinetics of gamma interferon and interleukin-4 in bovine *tuberculosis. Infect. Immun.* 68(9):5393-5400.

Rodrigues L. C., V. K. Diwan, and J. G. Wheeler (1993). Protective effect of BCG against tuberculous meningitis and miliary *tuberculosis*: a meta-analysis. *Int. J. Epidemiol.* 22(6):1154-1158.

Romano M., S. D'Souza, P. Y. Adnet, R. Laali, F. Jurion, K. Palfliet, and K. Huygen (2006). Priming but not boosting with plasmid DNA encoding mycolyl-transferase Ag85A from *Mycobacterium tuberculosis* increases the survival time of *Mycobacterium bovis* BCG vaccinated mice against low dose intravenous challenge with *M. tuberculosis* H37Rv. *Vaccine* 24(16):3353-3364.

Sada-Ovalle I., A. Chiba, A. Gonzales, M. B. Brenner, and S. M. Behar (2008). Innate invariant NKT cells recognize *Mycobacterium tuberculosis*-infected macrophages, produce interferongamma, and kill intracellular bacteria. *PLoS Pathog.* 4(12):e1000239.

Sadagopal S., M. Braunstein, C. C. Hager, J. Wei, A. K. Daniel, M. R. Bochan, I. Crozier, N. E. Smith, H. O. Gates, L. Barnett, L. Van Kaer, J. O. Price, T. S. Blackwell, S. A. Kalams, and D. S. Kernodle (2009). Reducing the activity and secretion of microbial antioxidants enhances the immunogenicity of BCG. *PLoS One* 4(5):e5531.

Sambandamurthy V. K., S.C. Derrick, K. V. Jalapathy, B. Chen, R. G. Russell, S. L. Morris, and W. R. Jacobs, Jr. (2005). Long-term protection against *tuberculosis* following vaccination with a severely attenuated double lysine and pantothenate auxotroph of *Mycobacterium tuberculosis. Infect. Immun.* 73(2):1196-1203.

Sambandamurthy V. K., X. Wang, B. Chen, R. G. Russell, S. Derrick, F. M. Collins, S. L. Morris, W. R. Jacobs, Jr. (2002). A pantothenate auxotroph of *Mycobacterium tuberculosis* is highly attenuated and protects mice against *tuberculosis. Nat. Med.* 8(10):1171-1174.

STOP-TB-Partnership (2009). TB vaccines pipeline.

Stover C. K., V. F. de la Cruz, T. R. Fuerst, J. E. Burlein, L. A. Benson, L. T. Bennett, G. P. Bansal, J. F. Young, M. H. Lee, G. F. Hatfull, et al. (1991). New use of BCG for recombinant vaccines. *Nature* 351(6326):456-60.

Sun R., Y. A. Skeiky, A. Izzo, V. Dheenadhayalan, Z. Imam, E. Penn E, K. Stagliano, S. Haddock, S. Mueller, J. Fulkerson, C. Scanga, A. Grover, S.C. Derrick, S. Morris, D. M. Hone, M. A. Horwitz, S. H. Kaufmann, and J. C. Sadoff (2009). Novel recombinant BCG expressing perfringolysin O and the over-expression of key immunodominant antigens; pre-clinical characterization, safety and protection against challenge with *Mycobacterium tuberculosis. Vaccine* 27(33):4412-4423.

Tanghe A., S. D'Souza, V. Rosseels, O. Denis, T. H. Ottenhoff, W. Dalemans, C. Wheeler, and K. Huygen (2001). Improved immunogenicity and protective efficacy of a *tuberculosis* DNA vaccine encoding Ag85 by protein boosting. *Infection and immunity* 69(5):3041-3047.

Tchilian E. Z., C. Desel, E. K. Forbes, S. Bandermann, C. R. Sander, A. V. Hill, H. McShane, and S. H. Kaufmann (2009). Immunogenicity and protective efficacy of prime-boost regimens with recombinant (delta)ureC hly+ *Mycobacterium Bovis* BCG and modified vaccinia virus Ankara expressing *M. tuberculosis* antigen 85A against murine *tuberculosis. Infect. Immun.* 77(2):622-631.

Torrelles J. B., A. K. Azad, and L. S. Schlesinger (2006). Fine discrimination in the recognition of individual species of phosphatidyl-myo-inositol mannosides from *Mycobacte-*

*rium tuberculosis* by C-type lectin pattern recognition receptors. *J. Immunol.* 177(3):1805-1816.

van der Veen R. C., T. A. Dietlin, A. Karapetian, S. M. Holland, and F. M. Hofman (2004). Extra-cellular superoxide promotes T cell expansion through inactivation of nitric oxide. *J. Neuroimmunol.* 153(1-2):183-189.

van Crevel R., T. H. Ottenhoff, and J. W. van der Meer (2002) Innate immunity to *Mycobacterium tuberculosis. Clin. Microbiol. Rev.* 15(2):294-309.

Velmurugan K., B. Chen, J. L. Miller, S. Azogue, S. Gurses, T. Hsu, M. Glickman, W. R. Jacobs, Jr., S. A. Porcelli, and V. Briken (2007). *Mycobacterium tuberculosis* nuoG is a virulence gene that inhibits apoptosis of infected host cells. *PLoS Pathog.* 3(7):e110.

Vergne I., J. Chua, and V. Deretic (2003). *Tuberculosis* toxin blocking phagosome maturation inhibits a novel Ca2+/calmodulin-PI3K hVPS34 cascade. *J. Exp. Med.* 198(4): 653-659.

Vergne I., J. Chua, H. H. Lee, M. Lucas, J. Belisle, V. Deretic (2005). Mechanism of phagolysosome biogenesis block by viable *Mycobacterium tuberculosis. Proc. Natl. Acad. Sci. U.S.A.* 102(11):4033-4038.

Verreck F. A., R. A. Vervenne, I. Kondova, K. W. van Kralingen, E. J. Remarque, G. Braskamp, N. M. van der Werff, A. Kersbergen, T. H. Ottenhoff, P. J. Heidt, S.C. Gilbert, B. Gicquel, A. V. Hill, C. Martin, H. McShane, and A. W. Thomas (2009). MVA.85A boosting of BCG and an attenuated, phoP deficient *M. tuberculosis* vaccine both show protective efficacy against *tuberculosis* in rhesus macaques. *PLoS One* 4(4):e5264.

Walker K. B., M. J. Brennan, M. M. Ho, J. Eskola, G. Thiry, J. Sadoff, R. Dobbelaer, L. Grode, M. A. Liu, U. Fruth, and P. H. Lambert (2010). The second Geneva Consensus: Recommendations for novel live TB vaccines. *Vaccine.*

WHO Report (2008). Global *tuberculosis* control—surveillance, planning, financing.

The invention claimed is:

1. A *mycobacterium* comprising a genetically engineered mutation in at least one endogenous gene selected from the group consisting of SapM, endogenous ManLAM α-1,2-mannosyltransferase corresponding to Mb1661c in *Mycobacterium bovis*, endogenous ManLAM α-1,2-mannosyltransferase corresponding to Mb2203 in *Mycobacterium bovis*, and endogenous LM α-1,6-mannosyltransferase corresponding to Mb2196 in *Mycobacterium bovis*, wherein, if the gene is SapM, the genetically engineered mutation is created by insertional mutagenesis.

2. The *mycobacterium* of claim 1, wherein the endogenous SapM gene, the ManLAM α-1,2-mannosyltransferase corresponding to the Mb1661c gene, the ManLAM α-1,2-mannosyltransferase corresponding to the Mb2203 gene, or the endogenous LM α-1,6-mannosyltransferase corresponding to the Mb2196 gene comprises SEQ ID NOs: 1, 3, 5, or 7, contiguous portions thereof having a length of at least 80% of the respective sequence, or sequences at least 95%, at least 98%, or at least 99% identical to SEQ ID NOs: 1, 3, 5, 7, or the contiguous portions thereof, respectively; or comprises a sequence encoding SEQ ID NOs: 2, 4, 6, or 8, contiguous portions thereof having a length of at least 80% of the respective sequence, or sequences at least 95%, at least 98%, or at least 99% identical to SEQ ID NOs: 2, 4, 6, 8, or the contiguous portions thereof, respectively.

3. The *mycobacterium* of claim 1, which is a member of the *Mycobacterium tuberculosis* complex.

4. The *mycobacterium* of claim 1, which is a *Mycobacterium tuberculosis, Mycobacterium bovis* or *M. bovis* Bacille Calmette-Guérin (BCG), wherein if the *mycobacterium* is *Mycobacterium bovis*, the endogenous ManLAM α-1,2-mannosyltransferase corresponding to Mb1661c in *Mycobacterium bovis* is Mb1661c, the endogenous ManLAM α-1,2-mannosyltransferase corresponding to Mb2203 in *Mycobacterium bovis* is Mb2203, and endogenous LM α-1,6-mannosyltransferase corresponding to Mb2196 in *Mycobacterium bovis* is Mb2196.

5. The *mycobacterium* of claim 1, wherein the genetically engineered mutation is created by insertion mutagenesis.

6. The *mycobacterium* of claim 1, which is selected from deposited strains LMG P-25310, LMG P-25309, LMG P-25308, and LMG P-25441.

7. The *mycobacterium* of claim 1, further comprising a genetically engineered mutation in at least one endogenous gene selected from secA2, sigH, and SodA.

8. A vaccine comprising:

the *mycobacterium* of claim 1, wherein the vaccine is a recombinant vaccine.

9. The vaccine of claim 8, wherein the vaccine is a vaccine against *tuberculosis*.

10. The vaccine of claim 9, wherein the vaccine is a *Mycobacterium bovis, M. bovis* Bacille Calmette-Guérin (BCG), or *M. tuberculosis*-based vaccine, wherein if the vaccine is a *Mycobacterium bovis*-based vaccine, the endogenous ManLAM α-1,2-mannosyltransferase corresponding to Mb1661c in *Mycobacterium bovis* is Mb1661c, the endogenous ManLAM α-1,2-mannosyltransferase corresponding to Mb2203 in *Mycobacterium bovis* is Mb2203, and endogenous LM α-1,6-mannosyltransferase corresponding to Mb2196 in *Mycobacterium bovis* is Mb2196.

11. The vaccine of claim 8, wherein the vaccine comprises a live attenuated vaccine.

12. A vaccine comprising a *mycobacterium* comprising a genetically engineered mutation in at least one endogenous gene selected from the group consisting of SapM, endogenous ManLAM α-1,2-mannosyltransferase corresponding to Mb1661c in *Mycobacterium bovis*, endogenous ManLAM α-1,2-mannosyltransferase corresponding to Mb2203 in *Mycobacterium bovis*, and endogenous LM α-1,6-mannosyltransferase corresponding to Mb2196 in *Mycobacterium bovis*, in a pharmaceutically acceptable carrier or excipient, wherein, if the gene is SapM, the genetically engineered mutation is created by insertional mutagenesis.

13. The vaccine of claim 12, wherein the vaccine is suitable to protect a mammal from challenge by a virulent *mycobacterium* selected from *M. bovis* or *M. tuberculosis*.

14. The vaccine of claim 13, wherein the vaccine comprises a live attenuated vaccine.

15. A method of treating *tuberculosis* in a subject, the method comprising:

administering the *mycobacterium* of claim 1 to the subject.

16. A method of inducing a immune response in a mammal, the method comprising:

inoculating the mammal with the *mycobacterium* of claim 1.

* * * * *